United States Patent
Dunn et al.

(10) Patent No.: US 10,124,098 B2
(45) Date of Patent: Nov. 13, 2018

(54) NEGATIVE PRESSURE WOUND CLOSURE DEVICE AND SYSTEMS AND METHODS OF USE IN TREATING WOUNDS WITH NEGATIVE PRESSURE

(71) Applicants: Smith & Nephew, Inc., Memphis, TN (US); University of Massachusetts, Boston, MA (US)

(72) Inventors: Raymond M. Dunn, Shrewsbury, MA (US); Edward Yerbury Hartwell, Hull (GB); John Kenneth Hicks, Pocklington (GB); Elizabeth Mary Huddleston, Copmanthorpe (GB); Carl Saxby, Brough (GB)

(73) Assignees: Smith & Nephew, Inc., Memphis, TN (US); University of Massachusetts, Boston, MA (US)

( * ) Notice: Subject to any disclaimer, the term of this patent is extended or adjusted under 35 U.S.C. 154(b) by 386 days.

(21) Appl. No.: 14/774,689

(22) PCT Filed: Mar. 12, 2014

(86) PCT No.: PCT/US2014/025059
§ 371 (c)(1),
(2) Date: Sep. 10, 2015

(87) PCT Pub. No.: WO2014/165275
PCT Pub. Date: Oct. 9, 2014

(65) Prior Publication Data
US 2016/0022885 A1 Jan. 28, 2016

Related U.S. Application Data

(60) Provisional application No. 61/891,857, filed on Oct. 16, 2013, provisional application No. 61/780,660, filed on Mar. 13, 2013.

(51) Int. Cl.
*A61M 1/00* (2006.01)
*A61F 13/00* (2006.01)
*A61F 13/02* (2006.01)

(52) U.S. Cl.
CPC ..... *A61M 1/0088* (2013.01); *A61F 13/00029* (2013.01); *A61F 13/00068* (2013.01);
(Continued)

(58) Field of Classification Search
CPC ........... A61M 1/0088; A61F 13/00029; A61F 13/00068; A61F 13/0216; A61F 13/022; A61F 2210/04
(Continued)

(56) References Cited

U.S. PATENT DOCUMENTS 3,194,239 A 7/1965 Sullivan
3,789,851 A 2/1974 LeVeen
(Continued)

FOREIGN PATENT DOCUMENTS

CN 101112326 A 1/2008
CN 203408163 1/2014
(Continued)

OTHER PUBLICATIONS

Hougaard, et al.: "The open abdomen: temporary closure with a modified negative pressure therapy technique," International Wound Journal, 2014 ISSN 1742-4801, pp. 13-16.
(Continued)

*Primary Examiner* — Philip R Wiest
(74) *Attorney, Agent, or Firm* — Knobbe, Martens, Olson & Bear, LLP

(57) ABSTRACT

Certain embodiments described herein are directed to an elongated layer of material and a lip to be placed in contact with a wound and the elongated layer of material to be wrapped around a wound filler, their methods of use and
(Continued)

systems incorporating the same, wherein the wound filler lip is configured to be positioned beneath the fascia. Additionally, some embodiments described herein are directed to the closure of the wound and the use of attachment mechanisms on the elongate layer and lip to attach to the wound surface.

30 Claims, 63 Drawing Sheets

(52) U.S. Cl.
CPC ........ *A61F 13/022* (2013.01); *A61F 13/0216* (2013.01); *A61M 2210/04* (2013.01)

(58) Field of Classification Search
USPC ........................................................ 604/319
See application file for complete search history.

(56) References Cited

U.S. PATENT DOCUMENTS

| | | | |
|---|---|---|---|
| 4,467,805 A | 8/1984 | Fukuda | |
| 4,699,134 A | 10/1987 | Samuelsen | |
| 4,815,468 A | 3/1989 | Annand | |
| 5,176,663 A | 1/1993 | Svedman et al. | |
| 5,264,218 A | 11/1993 | Rogozinski | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,562,107 A | 10/1996 | Lavendar et al. | |
| 5,584,859 A | 12/1996 | Brotz | |
| 5,636,643 A | 6/1997 | Argenta et al. | |
| 5,695,777 A | 12/1997 | Donovan et al. | |
| 5,960,497 A | 10/1999 | Castellino et al. | |
| 6,080,168 A | 6/2000 | Levin et al. | |
| 6,086,591 A | 7/2000 | Bojarski | |
| 6,142,982 A | 11/2000 | Hunt et al. | |
| 6,176,868 B1 | 1/2001 | Detour | |
| 6,503,208 B1 | 1/2003 | Skovlund | |
| 6,548,727 B1 | 4/2003 | Swenson | |
| 6,553,998 B2 | 4/2003 | Heaton et al. | |
| 6,566,575 B1 | 5/2003 | Stickels et al. | |
| 6,685,681 B2 | 2/2004 | Lockwood et al. | |
| 6,695,823 B1 | 2/2004 | Lina et al. | |
| 6,712,830 B2 | 3/2004 | Esplin | |
| 6,767,334 B1 | 7/2004 | Randolph | |
| 6,770,794 B2 | 8/2004 | Fleischmann | |
| 6,787,682 B2 | 9/2004 | Gilman | |
| 6,814,079 B2 | 11/2004 | Heaton et al. | |
| 6,893,452 B2 | 5/2005 | Jacobs | |
| 6,936,037 B2 | 8/2005 | Bubb | |
| 6,951,553 B2 | 10/2005 | Bubb et al. | |
| 6,977,323 B1 | 12/2005 | Swenson | |
| 6,994,702 B1 | 2/2006 | Johnson | |
| 7,004,915 B2 | 2/2006 | Boynton et al. | |
| 7,025,755 B2 | 4/2006 | Epstein | |
| 7,070,584 B2 | 7/2006 | Johnson et al. | |
| 7,117,869 B2 | 10/2006 | Heaton et al. | |
| 7,128,735 B2 | 10/2006 | Weston | |
| 7,144,390 B1 | 12/2006 | Hannigan et al. | |
| 7,153,312 B1 | 12/2006 | Torrie et al. | |
| 7,156,862 B2 | 1/2007 | Jacobs et al. | |
| 7,172,615 B2 | 2/2007 | Morriss et al. | |
| 7,189,238 B2 | 3/2007 | Lombardo et al. | |
| 7,196,054 B1 | 3/2007 | Drohan et al. | |
| 7,198,046 B1 | 4/2007 | Argenta et al. | |
| 7,216,651 B2 | 5/2007 | Argenta et al. | |
| D544,092 S | 6/2007 | Lewis | |
| 7,262,174 B2 | 8/2007 | Jiang et al. | |
| 7,279,612 B1 | 10/2007 | Heaton et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,367,342 B2 | 5/2008 | Butler | |
| 7,381,211 B2 | 6/2008 | Zamierowski | |
| 7,381,859 B2 | 6/2008 | Hunt et al. | |
| 7,413,571 B2 | 8/2008 | Zamierowski | |
| 7,438,705 B2 | 10/2008 | Karpowicz et al. | |
| 7,494,482 B2 | 2/2009 | Orgill et al. | |
| 7,524,315 B2 | 4/2009 | Blott et al. | |
| 7,534,240 B1 | 5/2009 | Johnson | |
| 7,540,848 B2 | 6/2009 | Hannigan et al. | |
| 7,553,306 B1 | 6/2009 | Hunt et al. | |
| 7,553,923 B2 | 6/2009 | Williams et al. | |
| 7,569,742 B2 | 8/2009 | Haggstrom et al. | |
| 7,578,532 B2 | 8/2009 | Schiebler | |
| D602,583 S | 10/2009 | Pidgeon et al. | |
| 7,611,500 B1 | 11/2009 | Lina et al. | |
| 7,615,036 B2 | 11/2009 | Joshi et al. | |
| 7,618,382 B2 | 11/2009 | Vogel et al. | |
| 7,622,629 B2 * | 11/2009 | Aali ...................... | A61F 15/002 128/888 |
| 7,625,362 B2 | 12/2009 | Boehringer et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,683,667 B2 | 3/2010 | Kim | |
| 7,699,823 B2 | 4/2010 | Haggstrom et al. | |
| 7,699,830 B2 | 4/2010 | Martin | |
| 7,699,831 B2 | 4/2010 | Bengtson et al. | |
| 7,700,819 B2 | 4/2010 | Ambrosio et al. | |
| 7,708,724 B2 | 5/2010 | Weston | |
| 7,713,743 B2 | 5/2010 | Villanueva et al. | |
| 7,722,528 B2 | 5/2010 | Arnal et al. | |
| 7,723,560 B2 | 5/2010 | Lockwood et al. | |
| 7,753,894 B2 | 7/2010 | Blott et al. | |
| 7,754,937 B2 | 7/2010 | Boehringer et al. | |
| 7,776,028 B2 | 8/2010 | Miller et al. | |
| 7,777,522 B2 | 8/2010 | Yang | |
| 7,779,625 B2 | 8/2010 | Joshi et al. | |
| D625,801 S | 10/2010 | Pidgeon et al. | |
| 7,815,616 B2 | 10/2010 | Boehringer et al. | |
| 7,820,453 B2 | 10/2010 | Heylen et al. | |
| 7,846,141 B2 | 12/2010 | Weston | |
| 7,857,806 B2 | 12/2010 | Karpowicz et al. | |
| 7,863,495 B2 * | 1/2011 | Aali ...................... | A61F 15/002 128/888 |
| 7,892,181 B2 | 2/2011 | Christensen et al. | |
| 7,896,856 B2 | 3/2011 | Petrosenko et al. | |
| 7,909,805 B2 | 3/2011 | Weston | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 7,981,098 B2 | 7/2011 | Boehringer et al. | |
| 8,030,534 B2 | 10/2011 | Radl et al. | |
| 8,057,447 B2 | 11/2011 | Olson et al. | |
| 8,062,272 B2 | 11/2011 | Weston | |
| 8,062,295 B2 | 11/2011 | McDevitt et al. | |
| 8,062,331 B2 | 11/2011 | Zamierowski | |
| 8,067,662 B2 | 11/2011 | Aali et al. | |
| 8,070,773 B2 | 12/2011 | Zamierowski | |
| 8,080,702 B2 | 12/2011 | Blott et al. | |
| 8,100,887 B2 | 1/2012 | Weston et al. | |
| 8,114,126 B2 | 2/2012 | Heaton et al. | |
| 8,123,781 B2 | 2/2012 | Zamierowski | |
| 8,128,615 B2 | 3/2012 | Blott et al. | |
| 8,129,580 B2 | 3/2012 | Wilkes et al. | |
| 8,142,419 B2 | 3/2012 | Heaton et al. | |
| 8,162,909 B2 | 4/2012 | Blott et al. | |
| 8,172,816 B2 | 5/2012 | Kazala, Jr. et al. | |
| 8,182,413 B2 | 5/2012 | Browning | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |

(56) References Cited

U.S. PATENT DOCUMENTS

| | | |
|---|---|---|
| 8,337,411 B2 | 12/2012 | Nishtala et al. |
| 8,353,931 B2 | 1/2013 | Stopek et al. |
| 8,357,131 B2 | 1/2013 | Olson |
| 8,362,315 B2 * | 1/2013 | Aali ............... A61F 15/002 602/41 |
| 8,399,730 B2 | 3/2013 | Kazala, Jr. et al. |
| 8,430,867 B2 | 4/2013 | Robinson et al. |
| 8,444,392 B2 | 5/2013 | Turner et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Dmitry |
| 8,936,618 B2 | 1/2015 | Sealy et al. |
| 8,945,030 B2 | 2/2015 | Weston |
| 8,951,235 B2 | 2/2015 | Hull et al. |
| 9,044,579 B2 | 6/2015 | Blott et al. |
| 9,061,095 B2 | 6/2015 | Adie et al. |
| 9,220,822 B2 | 12/2015 | Hartwell et al. |
| 9,408,755 B2 | 8/2016 | Larsson et al. |
| 9,655,807 B2 | 5/2017 | Locke et al. |
| 9,849,023 B2 | 12/2017 | Hall et al. |
| 9,895,270 B2 | 2/2018 | Coward et al. |
| 2001/0029956 A1 | 10/2001 | Argenta |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortanbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0267312 A1 | 12/2004 | Kanner et al. |
| 2005/0119694 A1 | 6/2005 | Jacobs et al. |
| 2005/0142331 A1 | 6/2005 | Anderson et al. |
| 2005/0182445 A1 | 8/2005 | Zamierowski |
| 2005/0222613 A1 | 10/2005 | Ryan |
| 2005/0258887 A1 | 11/2005 | Ito |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 * | 8/2007 | Mulligan ............ A61F 13/0203 604/305 |
| 2007/0213597 A1 | 9/2007 | Wooster |
| 2007/0219513 A1 | 9/2007 | Lina et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0167593 A1 | 7/2008 | Fleischmann |
| 2008/0275409 A1 | 11/2008 | Kane et al. |
| 2008/0287973 A1 | 11/2008 | Aster et al. |
| 2009/0005716 A1 | 1/2009 | Abuzaina Ferass et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | DeGheest et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299303 A1 | 12/2009 | Seegert |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 * | 6/2010 | Robinson ............ A61F 13/0203 604/319 |
| 2010/0160901 A1 | 6/2010 | Hu et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petier-Puchner et al. |
| 2010/0305490 A1 | 12/2010 | Coulthard et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0060204 A1 | 3/2011 | Weston |
| 2011/0066096 A1 | 3/2011 | Svedman |
| 2011/0077605 A1 | 3/2011 | Karpowicz et al. |

(56) References Cited

U.S. PATENT DOCUMENTS

| | | |
|---|---|---|
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Canada |
| 2011/0264138 A1 | 10/2011 | Avelar et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0313374 A1 | 12/2011 | Lockwood et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Goulthard |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | De Plessis et al. |
| 2012/0150133 A1 | 6/2012 | Heaton et al. |
| 2012/0157942 A1 | 6/2012 | Weston |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1* | 8/2012 | Dunn .................. A61B 17/08 604/319 |
| 2012/0220968 A1 | 8/2012 | Confalone et al. |
| 2012/0222687 A1 | 9/2012 | Czajka, Jr. et al. |
| 2012/0253302 A1 | 10/2012 | Corley |
| 2012/0277773 A1 | 11/2012 | Sargeant et al. |
| 2012/0302440 A1 | 11/2012 | Theliander et al. |
| 2013/0096518 A1 | 4/2013 | Hall et al. |
| 2013/0110058 A1 | 5/2013 | Adie et al. |
| 2013/0131564 A1 | 5/2013 | Locke et al. |
| 2013/0138054 A1 | 5/2013 | Fleischmann |
| 2013/0150814 A1 | 6/2013 | Buan |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0310781 A1 | 11/2013 | Phillips et al. |
| 2013/0331757 A1 | 12/2013 | Belson |
| 2014/0068914 A1 | 3/2014 | Coward et al. |
| 2014/0088455 A1 | 3/2014 | Christensen et al. |
| 2014/0094730 A1 | 4/2014 | Greener |
| 2014/0163415 A1 | 6/2014 | Zaiken et al. |
| 2014/0180225 A1 | 6/2014 | Dunn |
| 2014/0194836 A1 | 7/2014 | Kazala, Jr. et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2014/0249495 A1 | 9/2014 | Mumby |
| 2015/0005722 A1 | 1/2015 | Hu et al. |
| 2015/0025484 A1 | 1/2015 | Simmons et al. |
| 2015/0065968 A1 | 3/2015 | Sealy et al. |
| 2015/0080947 A1 | 3/2015 | Greener |
| 2015/0112290 A1 | 4/2015 | Dunn |
| 2015/0112311 A1 | 4/2015 | Hammond et al. |
| 2015/0119837 A1 | 4/2015 | Thompson, Jr. et al. |
| 2015/0148760 A1 | 5/2015 | Dodd et al. |
| 2015/0150729 A1 | 6/2015 | Dagger et al. |
| 2015/0157758 A1 | 6/2015 | Blucher et al. |
| 2015/0174304 A1 | 6/2015 | Askem et al. |
| 2015/0190288 A1 | 7/2015 | Dunn |
| 2015/0196431 A1 | 7/2015 | Dunn |

FOREIGN PATENT DOCUMENTS

| | | |
|---|---|---|
| DE | 2 949 920 | 3/1981 |
| DE | 10 2005 007016 | 8/2006 |
| EP | 1 320 342 | 6/2003 |
| EP | 2 279 016 | 2/2011 |
| EP | 2 366 721 | 9/2011 |
| EP | 2 368 523 | 9/2011 |
| EP | 2 404 626 | 1/2012 |
| EP | 2 341 955 | 12/2012 |
| EP | 2 529 767 | 12/2012 |
| EP | 2 563 421 | 3/2013 |
| EP | 2 567 682 | 3/2013 |
| EP | 2 567 717 | 3/2013 |
| EP | 2 594 299 | 5/2013 |
| EP | 2 601 984 A2 | 6/2013 |
| EP | 2 623 137 | 8/2013 |
| EP | 2 367 517 | 9/2013 |
| EP | 2 759 265 | 7/2014 |
| EP | 2 829 287 | 1/2015 |
| EP | 3 225 261 | 10/2017 |
| GB | 2389794 | 12/2003 |
| GB | 2423019 | 8/2006 |
| GB | 2489947 | 10/2012 |
| GB | 2496310 | 5/2013 |
| RU | 1818103 | 5/1993 |
| RU | 62504 | 4/2007 |
| WO | WO 2001/085248 | 11/2001 |
| WO | WO 2001/089392 | 11/2001 |
| WO | WO 2002/05737 | 1/2002 |
| WO | WO 2003/003948 | 1/2003 |
| WO | WO 2004/018020 | 3/2004 |
| WO | WO 2004/037334 | 5/2004 |
| WO | WO 2005/046761 | 5/2005 |
| WO | WO 2005/105174 | 11/2005 |
| WO | WO 2006/041496 | 4/2006 |
| WO | WO 2006/046060 | 5/2006 |
| WO | WO 2007/030601 | 3/2007 |
| WO | WO 2007/133618 | 11/2007 |
| WO | WO 2008/039223 | 4/2008 |
| WO | WO 2008/064502 | 6/2008 |
| WO | WO 2008/091521 | 7/2008 |
| WO | WO 2008/104609 | 9/2008 |
| WO | WO 2009/019495 | 2/2009 |
| WO | WO 2009/071926 | 6/2009 |
| WO | WO 2009/071933 | 6/2009 |
| WO | WO 2009/112062 | 9/2009 |
| WO | WO 2009/112848 | 9/2009 |
| WO | WO 2009/114624 | 9/2009 |
| WO | WO 2009/156709 | 12/2009 |
| WO | WO 2009/158132 | 12/2009 |
| WO | WO 2010/033725 | 3/2010 |
| WO | WO 2010/051073 | 5/2010 |
| WO | WO 2010/059612 | 5/2010 |
| WO | WO 2010/075180 | 7/2010 |
| WO | WO 2010/078349 | 7/2010 |
| WO | WO 2010/092334 | 8/2010 |

(56) References Cited

FOREIGN PATENT DOCUMENTS

| | | |
|---|---|---|
| WO | WO 2010/097570 | 9/2010 |
| WO | WO 2010/147535 | 12/2010 |
| WO | WO 2011/023384 | 3/2011 |
| WO | WO 2011/087871 | 7/2011 |
| WO | WO 2011/091169 | 7/2011 |
| WO | WO 2011/106722 | 9/2011 |
| WO | WO 2011/115908 | 9/2011 |
| WO | WO 2011/135284 | 11/2011 |
| WO | WO 2011/135286 | 11/2011 |
| WO | WO 2011/135287 | 11/2011 |
| WO | WO 2011/137230 | 11/2011 |
| WO | WO 2011/144888 | 11/2011 |
| WO | WO 2012/021553 | 2/2012 |
| WO | WO 2012/038727 | 3/2012 |
| WO | WO 2012/069793 | 5/2012 |
| WO | WO 2012/069794 | 5/2012 |
| WO | WO 2012/082716 | 6/2012 |
| WO | WO 2012/082876 | 6/2012 |
| WO | WO 2012/087376 | 6/2012 |
| WO | WO 2012/106590 | 8/2012 |
| WO | WO 2012/112204 | 8/2012 |
| WO | WO 2012/136707 | 10/2012 |
| WO | WO 2012/142473 | 10/2012 |
| WO | WO 2012/156655 | 11/2012 |
| WO | WO 2012/168678 | 12/2012 |
| WO | WO 2013/007973 | 1/2013 |
| WO | WO 2013/012381 | 1/2013 |
| WO | WO 2013/043258 | 3/2013 |
| WO | PCT/IB2013/002485 | 5/2013 |
| WO | WO 2013/071243 | 5/2013 |
| WO | WO 2013/076450 | 5/2013 |
| WO | WO 2013/079947 | 6/2013 |
| WO | WO 2013/175309 | 11/2013 |
| WO | WO 2013/175310 | 11/2013 |
| WO | WO 2013/014871 | 1/2014 |
| WO | WO 2013/014922 | 1/2014 |
| WO | WO 2014/013348 | 1/2014 |
| WO | WO 2014/014842 | 1/2014 |
| WO | WO 2014/024048 | 2/2014 |
| WO | WO 2014/158526 | 10/2014 |
| WO | WO 2014/165275 | 10/2014 |

OTHER PUBLICATIONS

International Search Report and Written Opinion re PCT Application No. PCT/US2014/025059, dated Aug. 6, 2014.
Kapischke, M. et al., "Self-fixating mesh for the Lichtenstein procedure—a prestudy", Langenbecks Arch Surg (2010), 395 p. 317-322.
International Preliminary Report on Patentability, re PCT Application No. PCT/US2014/025059, dated Sep. 24, 2015.
Definition of "3D Printer", American Heritage Dictionary of the English Language, Fifth Edition, 2016, accessed Feb. 22, 2018, in 1 page. URL: https://www.thefreedictionary.co.
Definition of "Oculiform", Webster's Revised Unabridged Dictionary, 1913, accessed from the Free Dictionary on May 30, 2018, in 1 page. URL: https://www.thefreedictionary.com/Oculiform.

\* cited by examiner

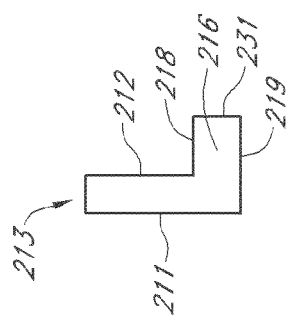
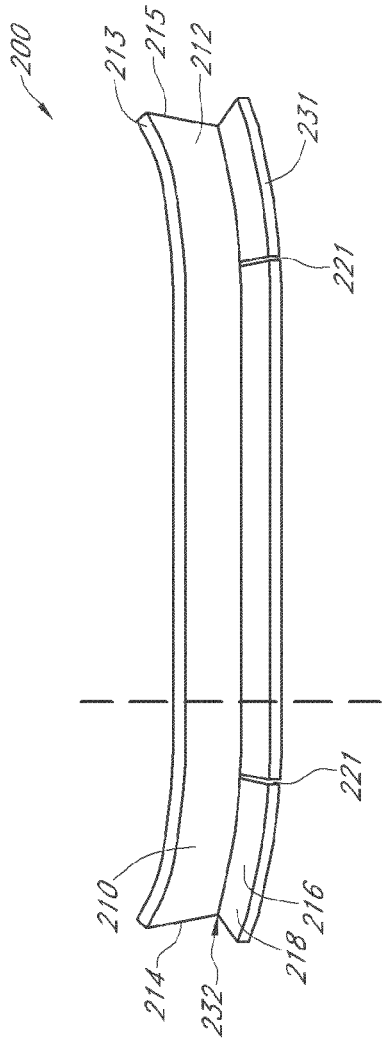

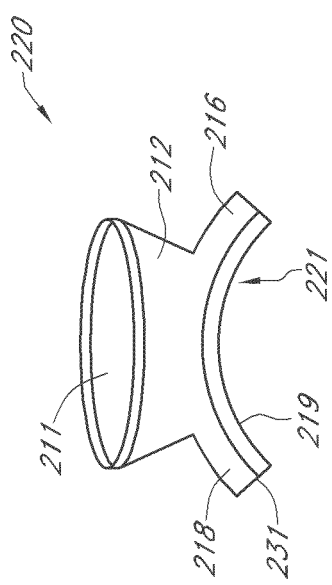

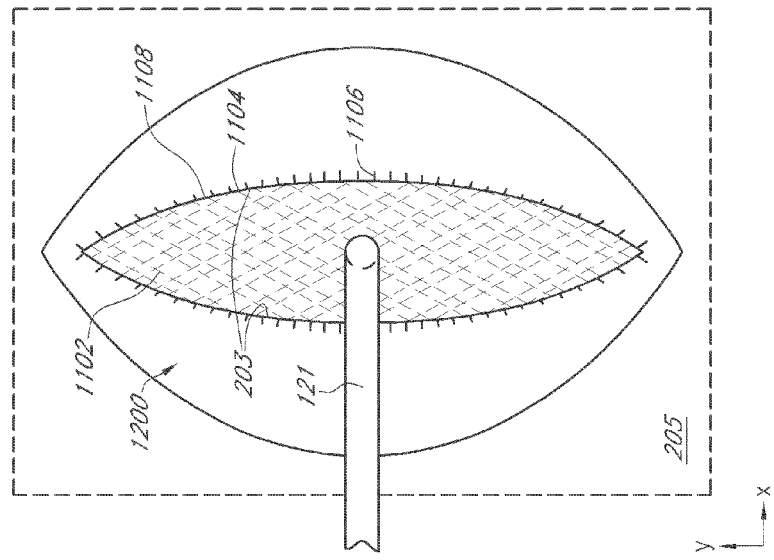
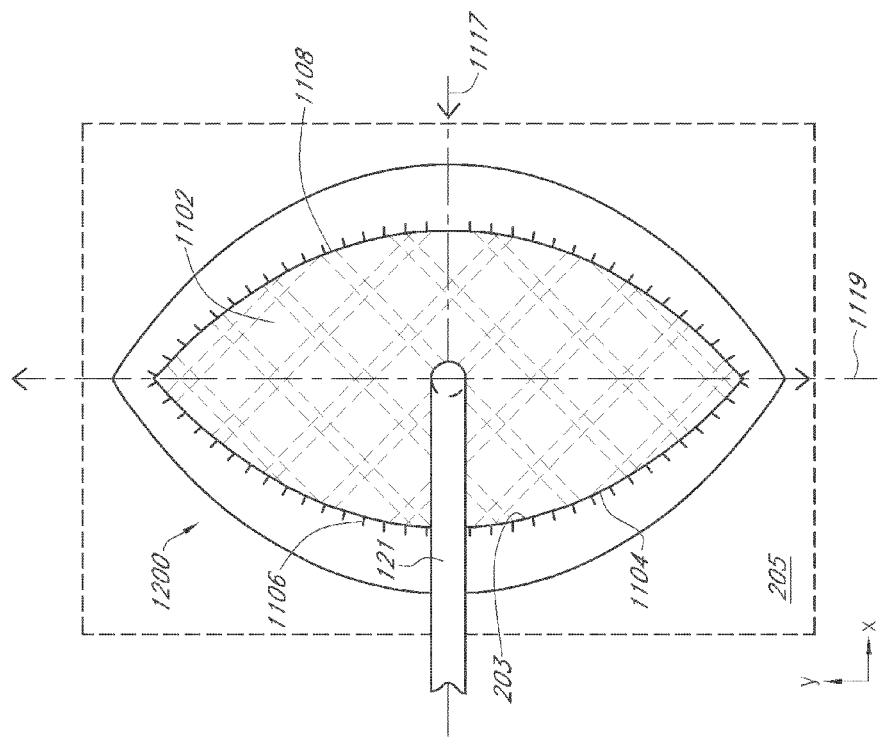
FIG. 13A
FIG. 13B

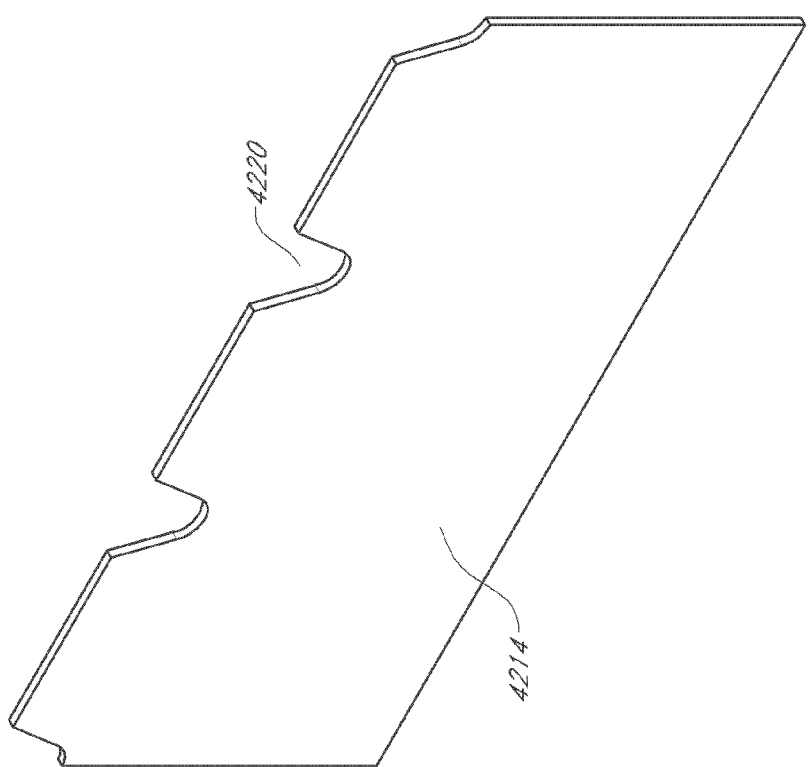

NEGATIVE PRESSURE WOUND CLOSURE DEVICE AND SYSTEMS AND METHODS OF USE IN TREATING WOUNDS WITH NEGATIVE PRESSURE

CROSS-REFERENCE TO RELATED APPLICATIONS

This application is a national stage application of International Patent Application No. PCT/US2014/025059, filed on Mar. 12, 2014, which claims the benefit of U.S. Provisional Application No. 61/780,660, filed Mar. 13, 2013, entitled NEGATIVE PRESSURE WOUND CLOSURE DEVICE AND SYSTEMS AND METHODS OF USE IN TREATING WOUNDS WITH NEGATIVE PRESSURE, and U.S. Provisional Application No. 61/891,857, filed Oct. 16, 2013, entitled NEGATIVE PRESSURE WOUND CLOSURE DEVICE AND SYSTEMS AND METHODS OF USE IN TREATING WOUNDS WITH NEGATIVE PRESSURE, the entireties of both of which are hereby incorporated by reference. The benefit of priority to the foregoing applications is claimed under the appropriate legal basis including, without limitation, under 35 U.S.C. § 119(e).

BACKGROUND OF THE INVENTION

Field of the Invention

Embodiments described herein relate to devices and methods that can be used to treat a wound with negative pressure. Particular embodiments can also be useful to aid in wound closure, for example in abdominal wounds or following fasciotomy procedures.

SUMMARY OF THE INVENTION

Generally, the embodiments described herein can be used to assist in the treatment of wounds with negative pressure. The embodiments can be particularly useful in treating large wounds, such as abdominal wounds and/or for fasciotomy procedures, where closure and approximation of the wound edges is challenging. Certain embodiments described herein are directed to an elongated layer of material and a lip to be placed in contact with a wound and the elongated layer of material to be wrapped around a wound filler, their methods of use and systems incorporating the same, wherein the wound filler lip is configured to be positioned beneath the fascia. Additionally, some embodiments described herein are directed to the closure of the wound and the use of attachment mechanisms on the elongate layer and lip to attach to the wound surface.

In one embodiment, an apparatus for wound treatment comprises an elongate layer of material configured to be placed in contact with a wound. The elongate layer is capable of being formed into an annular shape. A lip extends outwardly from the elongate layer when the layer is arranged in an annular shape, wherein the lip is capable of being positioned beneath the fascia of a patient.

In some embodiments, the elongate layer can be made of foam. The lip can be made of foam. The elongate layer may have an inner surface and an outer surface and a thickness therebetween, wherein the thickness of the layer is less than a height of the inner and outer surfaces. The inner surface of the elongate layer can be configured to be attached to a wound filler. The inner surface of the layer can have means for attaching the inner surface of the layer to the wound filler. The outer surface of the layer can be configured to attach to a wound surface. The outer surface can have means for attaching the outer surface of the layer to the wound surface. The lip can have means for attaching the lip to the fascia. The outer surface of the layer can have means for attaching the outer surface of the layer to the wound surface that is different from the means for attaching the lip to the fascia.

In some embodiments, a plurality of fingers can be extending outwardly from the lip. The fingers can be covered by a slitted organ protection layer. The fingers can comprise a foam material different from the material of the strip. The foam material for the fingers can comprise foam in some embodiments having a porosity between 200 ppi to 60 ppi.

In some embodiments, the layer and lip can form a generally L-shaped cross-section. The layer can have a first end and a second end and a means for attaching the first and second ends together.

The apparatus for wound treatment in some embodiments can further comprise a wound filler, wherein the elongate layer described above can surround the wound filler. The wound filler can comprise foam. An organ protection layer can be configured to be positioned over a wound beneath the wound filler. One or more foam layers can be configured to be positioned above and/or below the wound filler. A wound cover can be configured to be placed over a wound. The apparatus may also comprise a connection for connecting the wound cover to a source of negative pressure. A negative pressure source can be configured to be connected to the wound cover to provide negative pressure to a wound.

In one embodiment, a method of treating a wound using the apparatus can comprise applying negative pressure to the wound through a wound cover positioned over the wound. A wound filler can be positioned within the wound, wherein the wound filler is surrounded by the elongate layer of material and the lip is positioned beneath the fascia. In some embodiments, the wound can be an abdominal wound. In some embodiments, an organ protection layer is positioned over the wound and the wound filler is then positioned within the wound.

In one embodiment, an apparatus for wound treatment comprises a wound filler configured to collapse horizontally within a wound. A securing material can be configured to surround the wound filler, the securing material comprises an elongate layer configured to be placed in contact with the wound, and a lip extending outwardly from elongate layer. The lip is capable of being positioned beneath the fascia of a patient. The elongate layer and the lip are integrated as a single piece and form a generally L-shaped cross-section. The apparatus further comprises a wound cover configured to be placed over a wound.

In some embodiments, an inner surface of the layer can be configured to be attached to the wound filler. In some embodiments, the inner surface can have means for attaching the inner surface of the layer to the wound filler. In some embodiments, the means for attaching the inner surface of the layer to the wound filler comprise an attachment mechanism selected from the group consisting of a barb, an adhesive, Velcro, hooks of Velcro, mushroom shaped hooks of Velcro, a hooked shape, a staggered hook, a staggered barb, and any combination thereof.

In some embodiments, an outer surface of the layer can be configured to be attached to a wound surface. The outer surface can have means for attaching the outer surface of the layer to the wound surface. The means for attaching the outer surface of the layer to the wound surface is selected from the group consisting of a barb, an adhesive, Velcro, hooks of Velcro, mushroom shaped hooks of Velcro, a hooked shape, a staggered hook, a staggered barb, and any combination thereof.

In some embodiments, the lip can have means for attaching the lip to the fascia. The means for attaching the lip to the fascia comprise an attachment mechanism selected from the group consisting of a barb, an adhesive, Velcro, hooks of Velcro, mushroom shaped hooks of Velcro, a hooked shape, a staggered hook, a staggered barb, and any combination thereof. The means for attaching the lip to the fascia comprise a lateral attachment mechanism, the lateral attachment mechanism extending outwardly from a front surface of the lip.

In some embodiments, the apparatus for wound treatment further comprising a plurality of fingers extending outwardly from the lip. In some embodiments, the apparatus for wound treatment can further comprise an organ protection layer configured to be positioned over a wound beneath the wound filler. In some embodiments, the apparatus for wound treatment can further comprise one or more foam layers configured to be positioned above and/or below the wound filler. In some embodiments, the apparatus for wound treatment can further comprise a connection for connecting the wound cover to a source of negative pressure. In some embodiments, the apparatus for wound treatment further comprising a negative pressure source configured to be connected to the wound cover to provide negative pressure to the wound.

In another embodiment, a method of treating a wound using the apparatus of any one of the preceding claims, comprising applying negative pressure to the wound through the wound cover positioned over the wound with the wound filler positioned within the wound, wherein the wound filler is surrounded by the elongate layer and the lip is positioned beneath the fascia; and wherein the wound filler collapses horizontally under negative pressure.

BRIEF DESCRIPTION OF DRAWINGS

FIG. 2A illustrates an embodiment of a wound securing material comprising an elongate layer.

FIG. 2B illustrates a cross sectional view of the wound securing material of FIG. 2A, showing an elongate layer with a lip having an L-shaped cross-section.

FIGS. 2D-2E illustrate side views of the wound securing material of FIG. 2A arranged in an annular shape, with slits shown.

FIGS. 13A-B illustrate a wound closure device closing a wound.

FIGS. 15A-F illustrate multiple views of an embodiment of a stabilizing structure.

DETAILED DESCRIPTION OF THE PREFERRED EMBODIMENTS

Figure 1:
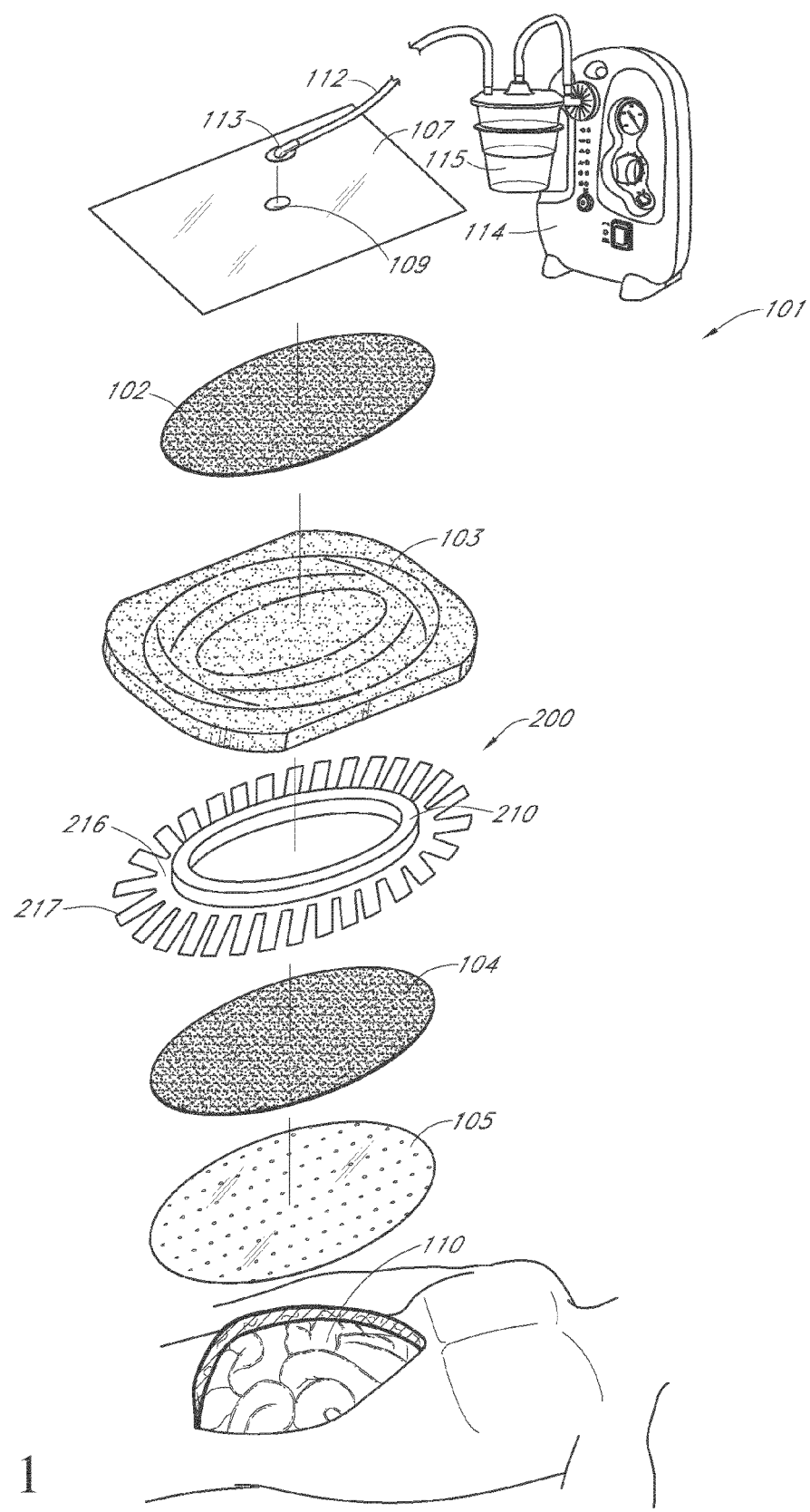
FIG. 1 illustrates an embodiment of a negative pressure treatment system.

Various embodiments that can be used for the treatment of wounds will now be described with references to the following figures and description which follow. It will be of course understood that various omissions, substitutions, and changes in the form and details of the embodiments illustrated can be made without departing from the spirit of the disclosure. Additionally, the various features and processes described above can be used independently of one another, or can be combined in various ways. All possible combinations and subcombinations are intended to fall within the scope of this disclosure. Many of the embodiments described above include similar components, and as such, these similar components can be interchanged in different embodiments.

Embodiments disclosed in this section or elsewhere in this specification relate to apparatuses and methods of treating a wound with reduced pressure, including pump and wound dressing components and apparatuses. Generally, the embodiments including the wound fillers described herein may be used in combination with a negative pressure system comprising a drape or wound cover placed over the filler. A vacuum source, such as a pump, may be connected to the cover, for example, through one or more tubes connected to an aperture or port made in or under the cover. The apparatuses and components comprising the wound overlay and packing materials, if any, are sometimes collectively referred to herein as dressings. Further details of methods and apparatuses that are usable with the embodiments described herein are found in FIGS. 14-25G and the accompanying text, and in the following applications, which are hereby incorporated by reference in their entireties: application Ser. No. 11/919,355, titled "Wound treatment apparatus and method," filed Oct. 26, 2007, published as US 2009/0306609; U.S. Pat. No. 7,753,894, titled "Wound cleansing apparatus with stress," issued Jul. 13, 2010; application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; application Ser. No. 13/365,615, titled "Negative Pressure Wound Closure Device," filed Feb. 3, 2012, published as US 2012/0209227, and International Application No. PCT/US2013/050698, titled "Negative Pressure Wound Closure Device," filed Jul. 16, 2013.

It will be appreciated that throughout this specification reference is made to a wound or wounds. It is to be understood that the term wound is to be broadly construed and encompasses open and closed wounds in which skin is torn, cut or punctured, or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the negative pressure treatment system described herein can be particularly suited for incisional wounds that exude a small amount of wound exudate.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for an organ protection layer 105 which may be cut to size to be placed over the wound site 110. Preferably, the organ protection layer 105 can be a material which will not adhere to the wound site or the exposed viscera in close proximity. In one embodiment, the organ protection layer is permeable. For example, the organ protection layer 105 can be provided with openings, such as holes, slits, or channels, to allow the removal of fluids from the wound site 110 or the transmittal of negative pressure to the wound site 110. Additional embodiments of the organ protection layer 105 are described in further detail below.

In some embodiments, a tissue protection layer can be used instead of or in addition to the organ protection layer to protect surrounding tissues near the wound site. For example, a tissue protection layer can be used in place of the organ protection layer if the wound closure device is used over non-abdominal wounds. Additionally, in some embodiments, the tissue protection layer can be used with the organ protection layer to protect the surrounding organs and tissues.

Certain embodiments of the negative pressure treatment system 101 may also use one or more foam layers 102 and 104 that may be cut to size (e.g., into an oval shape) to fit within the wound. As illustrated in FIG. 1, a foam layer 104 can be disposed over the organ protection layer 105. The foam layer 104 can be configured to be positioned below a wound filler 103 and above the organ protection layer. In some embodiments, one or more foam layers can be configured to be positioned above and/or below a wound filler 103. In such embodiments, as illustrated for example in FIGS. 6A and 6B, the wound filler 103 is positioned over the foam layer 104, and a foam layer 102 is positioned over the wound filler 103. In other embodiments, one or both of these foam layers are optional, and may not be used at all.

The foam layer(s) above and/or below the wound filler 103 can protect the wound cover and assist in fluid flow. In some embodiments, the foam can have a thickness of the range of 1 mm to 20 mm (or about 1 mm to about 20 mm), for example between 5 mm and 15 mm (or about 5 mm to about 15 mm).

Certain embodiments of the negative pressure treatment system 101 may also use wound filler 103, which can be disposed over the wound contact layer 105 and/or over the foam layer 104. The wound filler 103 can be cut into an appropriate shape to fit within a wound, e.g., an oval shape. The wound filler illustrated in FIG. 1 has portions that can be removed to provide an appropriate size for fitting within the wound. This wound filler 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. Preferably, this wound filler 103 can channel wound exudate and other fluids through itself when negative pressure is applied to the wound. Some wound fillers 103 may include preformed channels or openings for such purposes.

In some embodiments, the wound filler may include a material or materials that are more compressible in a horizontal plane than in a vertical dimension. Such materials may compress horizontally as negative pressure is applied to cause the wound edges to draw closer together, while maintaining relatively rigid to prevent vertical collapse of the wound cover 107 described below. Examples of wound fillers that may be used are described in application Ser. No. 13/365,615, titled "Negative Pressure Wound Closure Device," filed Feb. 3, 2012, published as US 2012/0209227, incorporated by reference herein. Additional wound filler materials and characteristics may be used as described in International Application No. PCT/US2013/050698, titled "Negative Pressure Wound Closure Device," filed Jul. 16, 2013, incorporated by reference herein. The wound closure devices and treatment methods of horizontally compressing material and/or stabilizing structures to be incorporated into wound closure devices will be described in further detail below with respect to FIGS. 14-25G.

Additionally, some embodiments of the negative pressure treatment system 101 may comprise an additional wound filler material 200 that facilitates securement of the wound filler 103 to the wound. This material 200 will be hereinafter referred to as wound securing material 200. As illustrated and as described in further detail below, the wound securing material 200 may comprise an elongate strip of material 210 that may be formed in an annular shape and sized to fit over the outer dimension of the wound filler 103. The wound securing material 200 may be placed in the wound before or with the wound filler 103. The wound securing material 200 can be configured to be placed in contact with the wound edges, such that the wound securing material is between the wound edge and the wound filler material 103. The wound securing material 200 can have a lip 216 extending outwardly when the wound securing material is in an annular shape. In certain embodiments, the wound securing material 200 can have a plurality of fingers 217 protruding outwardly from the lip. In certain embodiments, the lip and the fingers can be positioned beneath the fascia of the patient in order to secure the wound filler within the wound. Additional embodiments of the wound securing material 200 are described in further detail below.

Preferably, a wound cover 107 is used to seal the wound site 110. The wound cover 107 can be at least partially liquid impermeable, such that at least a partial negative pressure may be maintained at the wound site. Suitable materials for the wound cover 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the wound cover may be hydrophobic or hydrophilic. Examples of suitable materials include Transeal® available from DeRoyal and OpSite® available from Smith & Nephew. In order to aid patient comfort and avoid skin maceration, the wound cover in certain embodiments are at least partly breathable, such that water vapor is able to pass through without remaining trapped under the dressing. An adhesive layer may be provided on at least a portion the underside of the wound cover 107 to secure the wound cover to the skin of the patient, although certain embodiments may instead use a separate adhesive or adhesive strip. Optionally, a release layer may be disposed over the adhesive layer to protect it prior to use and to facilitate handling the wound cover 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The wound cover 107 may be connected to the source of negative pressure 114 via a conduit 112. The conduit 112 may be connected to a port 113 situated over an aperture 109 in the wound cover 107, or else the conduit 112 may be connected directly through the aperture 109 without the use of a port. In a further alternative, the conduit may pass underneath the wound cover and extend from a side of the wound cover. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 2C:
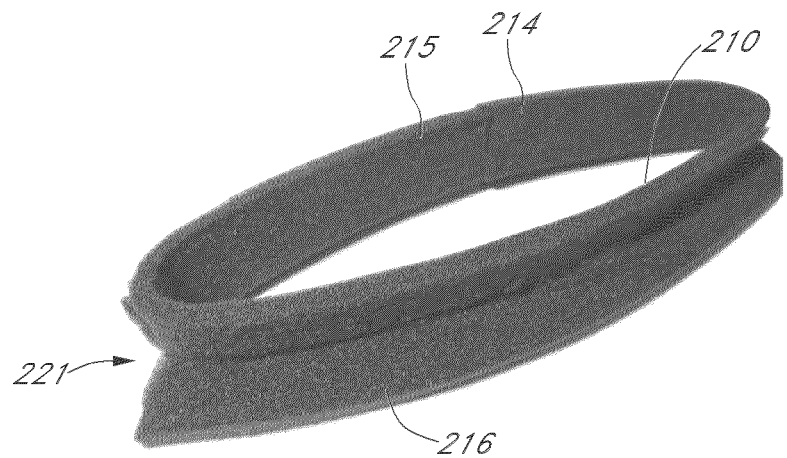
FIG. 2C is a perspective view the wound securing material of FIG. 2A arranged in an angular shape.

FIGS. 2A-2E illustrate embodiments of the wound securing material 200 with a lip that may be used in the negative pressure systems and methods as described herein. As compared to FIG. 1, the securing material 200 in FIGS. 2A-2E do not include fingers, which are shown in the embodiment of FIGS. 3A-3B. FIG. 2A illustrates an embodiment of the securing material 210 as an elongate layer or strip 210 that may have a straight or substantially straight length between ends 214 and 215 before use, and which may be cut to an appropriate length to be sized around wound filler 103. The ends 214, 215 can be joined to form an angular shape and can be attached through an attachment mechanism such as an adhesive, gripper or barbs, Velcro, hooks of Velcro, mushroom shaped hooks of Velcro, or other attachment mechanism known in the art. For example, after the elongate strip is cut to an appropriate length, its ends 214 and 215 may be brought together and attached to form an annular shape as shown in FIG. 2C. In other embodiments, the wound securing material may be pre-formed into an annular shape to fit different sizes of wound fillers.

As illustrated in FIGS. 2A-2E, the wound securing material 200 can have a lip 216, an inner surface 211, an outer surface 212, and a thickness 213 therebetween. In some embodiments, the elongate layer 210 can have a height of the inner and outer surface 211, 212 that is greater than its thickness 213. The inner surface 211 of the elongate layer can be configured to attach to the wound filler 103. The wound securing material 200 including the lip 216 and the elongate layer 210 can stabilize the wound filler and/or wound closure device in position within the wound.

In some embodiments, the elongate layer can have a lip forming an L-shaped cross-section as illustrated in FIG. 2A-E. FIG. 2B illustrates a cross sectional view of an embodiment of an elongate layer with a lip 216 having an L-shaped cross-section. In some embodiments, the elongate layer can be in the form of a strip without a lip. In such embodiments, the elongate layer can be used in the same way as described with reference to the elongate layer with a lip herein however a portion of the elongate layer is not disposed beneath the fascia.

Figure 2D:
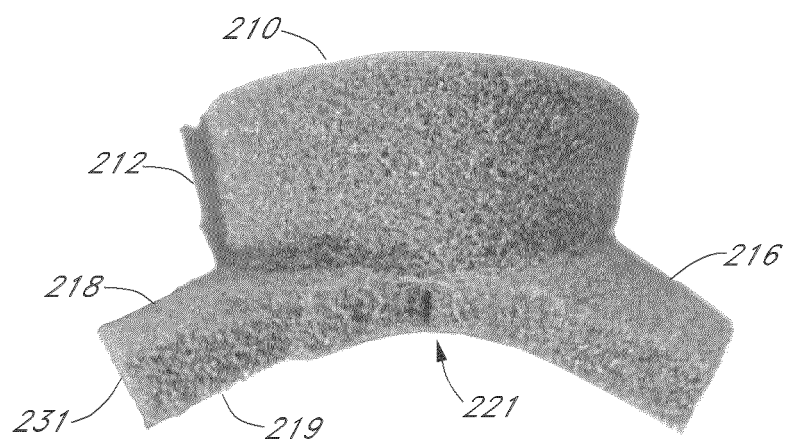
Figure 3A:
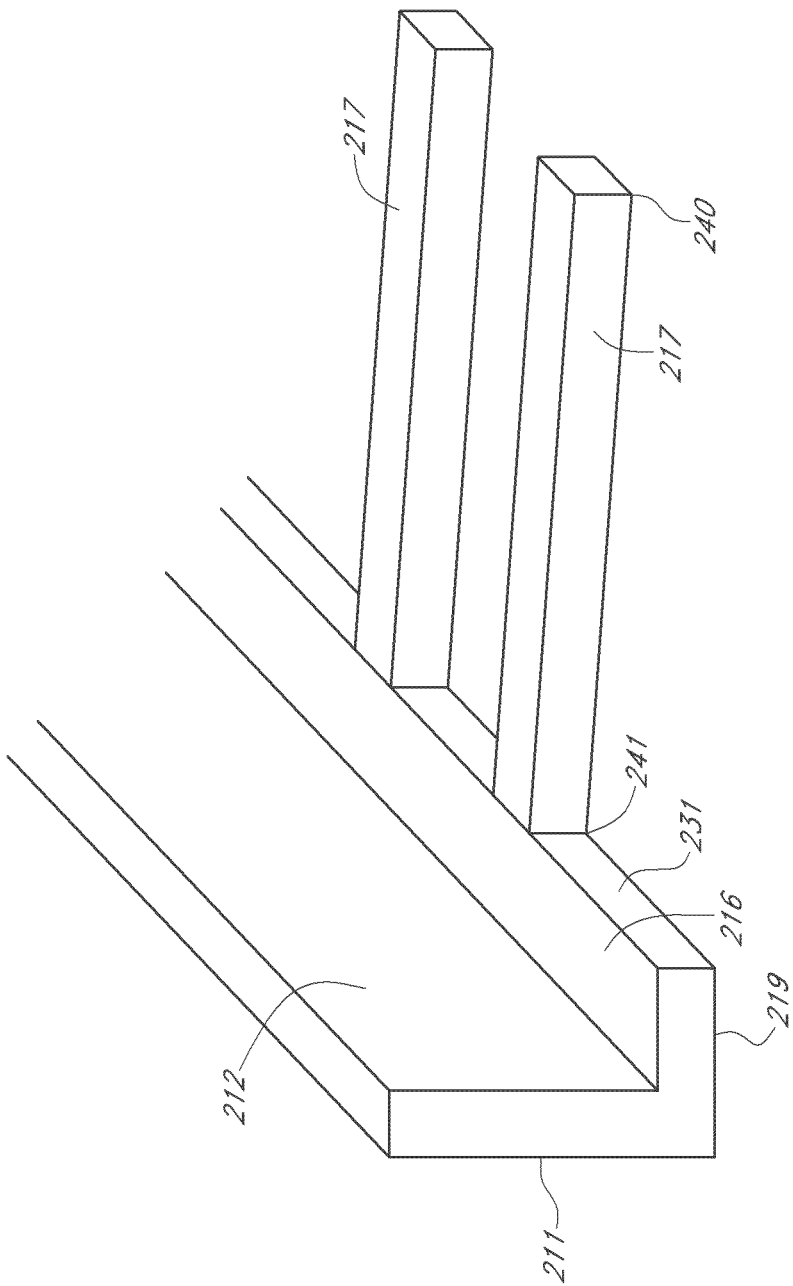
FIG. 3A illustrates an embodiment of a wound securing material with an elongate layer of material, a lip, and a plurality of fingers extending outwardly from the lip.
Figure 3B:
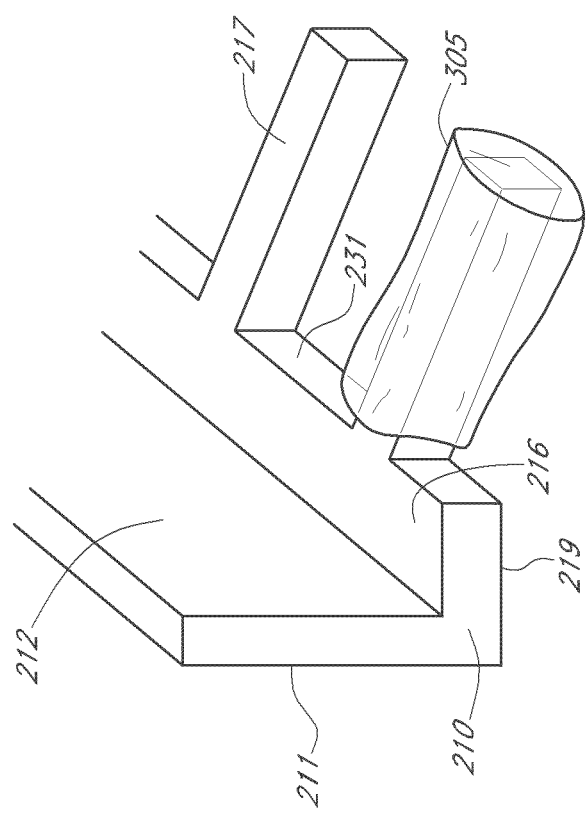
FIG. 3B illustrates an embodiment of a wound securing material with an elongate layer, a lip, and fingers surrounded by an organ protection layer.

FIG. 2D-2E illustrates an embodiment of an elongate layer 220 arranged in an annular shape with slits shown. The lip 216 can have slits or cut outs 221 that allow for the bending of the elongate layer into the angular shape formation as illustrated in FIG. 2A-2E.

In some embodiments, the wound securing material 200 of FIG. 2A can be made of foam. In other embodiments, the wound securing material 200 can be formed of any material that can transmit negative pressure and/or fluid. In some embodiments, the material can be a felted open reticulated foam having a porosity in the range of 60 ppi (or about 60 ppi) or less, 50 ppi (or about 50 ppi) or less, 40 ppi (or about 40 ppi) or less, 30 ppi (or about 30 ppi) or less, 20 ppi (or about 20 ppi) or less, or 10 ppi (or about 10 ppi) or less. The foam can be compressed with heat and/or pressure to form the more rigid felted foam. For example, in some embodiments, the material can be a felted, 10-60 ppi (or about 10 to about 60 ppi) open reticulated foam, such as one that has been compressed with heat and/or pressure to form the more rigid felted foam. Such a foam may supply little barbs that can help attach the material to the tissue better. In some embodiments, the felting can be important to increase the rigidity of the foam but can still leave a structure that can still act as a manifold for exudates and the vacuum. In some embodiments, the results of felting are a more dense structure, and therefore the resulting surface can be less open for tissue ingrowth. In some embodiments, the foam can have a finer pore size, e.g., 60 ppi to 200 ppi (or about 60 ppi to about 200 ppi), or greater than 60 ppi (or about 60 ppi), to minimize granulation tissue formation.

In some embodiments, the wound securing material 200 can be made of materials that do not adhere to the wound site. The non-adherent material can assist in wound closure without adhering to the tissue within the wound site. The non-adherent material can prevent injury to the wound tissue when the wound closure device is removed from the wound site. Additionally, the wound securing material 200 can be a porous or non-porous material.

In one embodiment, the wound securing material 200 can be a flexible covering, such as a mesh film, that is secured to the outer perimeter surface of the wound filler 103 and can expand and contract with the expansion and contraction of the wound filler 103. In one embodiment, the wound securing material 200 can be a mesh film or a composite polyester mesh film, such as the Parietex™ mesh from Covidien (Mansfield, Mass.).

In some embodiments, the inner surface 211 may be configured to attached to the wound filler through any suitable attachment mechanism such as an adhesive, gripper or barbs, Velcro, hooks of Velcro, mushroom shaped hooks of Velcro, or other attachment mechanism known in the art. In some embodiments, the elongate layer 210 is supplied with a means of attachment integrated within the inner surface 211. In some embodiments, the inner surface 211 can be prepared prior to insertion into the body cavity with the attachment means.

The elongate layer 210 may also have an outer surface 212 configured to attach to the wound surface. In some embodiments, the outer surface 212 can be configured to attach to the wound surface through any suitable tissue attachment mechanism such as an adhesive, gripper or barbs, tissue grabbers known in the art, glue, suturing, Parietex, or other tissue attachment mechanism known in the art. For example, in certain embodiments, the outer surface 212 can have barbs that may help attach to the tissue, such as backward facing barbs that can anchor into the tissue when the barbs are pulled in the direction that closes the wound cavity but can be released when pushed in the opposite direction, and can provide a closing force on the wound. In some embodiments, the barbs can be polymer, glass, metal, fine hair like structures, and/or other barbs known in the art. In some embodiments, the barbs may be smooth rod like projections. Alternatively, in some embodiments, the barbs may have a rough surface or spiked surface to increase adhesion. In some embodiments, the length of the barbs can be in the range of 0.1 mm to 5 mm (or about 0.1 mm to about 5 mm), for example 5 mm (or about 5 mm), 4 mm (or about 4 mm), 3 mm (or about 3 mm), 2 mm (or about 2 mm), or 1 mm (or about 1 mm) In some embodiments, the spacing of the barbs can be in the range of 0.1 mm to 10 mm (or about 0.1 mm to about 10 mm), for example 10 mm (or about 10 mm), 8 mm (or about 8 mm), 6 mm (or about 6 mm), 4 mm (or about 4 mm), 2 mm (or about 2 mm), or 1 mm (or about 1 mm) In some embodiments, the elongate layer 210 is supplied with a means of attachment integrated within the outer surface 212. In some embodiments, the elongate layer 210 outer surface 212 can be prepared prior to insertion into the body cavity with the attachment means.

In some embodiments, the lip 216 can attach to the base 232 of the outer surface 212 or be formed with the elongate layer 210 to form a generally L-shaped cross-section as illustrated in FIG. 2B. In some embodiments, the lip 216 can be made of the same or a different foam material as that described above. In other embodiments, the lip can be formed of other material known in the art appropriate for contacting the wound or fascia of a patient. In some embodiments, the lip 216 can be formed of material that can transmit negative pressure and/or fluid. In some embodiments, the lip 216 can be a non-porous material. In some embodiments, the lip 216 can be a porous material. In some embodiments, the lip can be made of materials that do not adhere to the wound site. The non-adherent material can assist in wound closure without adhering to the tissue within the wound site. The non-adherent material can prevent injury to the wound tissue when the wound closure device is removed from the wound site.

Additionally, in some embodiments, the lip 216 can be a flexible material, for example a flexible polymer material. As the lip extends outward from the wound filler the lip 216 can have varying rigidity, for example near the wound filler the lip 216 can be rigid and as the lip extends outward radially the lip material can increase in flexibility and/or decrease in strength. The lip 216 can have a top surface 218, a bottom surface 219, and a thickness therebetween as illustrated in FIG. 2B. Additionally, the lip 216 can have a front or outward surface 231.

The lip 216 can have an upper surface 218 that can be configured to attach to the wound site. In some embodiments, the lip can have a means for attaching the lip to the fascia. In some embodiments, the upper surface 218 can be attached to the wound site through a tissue attachment mechanism such as an adhesive, gripper or barbs, tissue grabbers known in the art, glue, suturing, Parietex, or other tissue attachment mechanism known in the art. In some embodiments, the barbs may be smooth rod like projections. Alternatively, in some embodiments, the barbs may have a rough surface or spiked surface to increase adhesion. For example, in certain embodiments, the lip 216 can have barbs, such as backward facing barbs, that may help attach to the tissue or anchor the lip into the fascia when the barbs are pulled in the direction that closes the wound cavity but can be released when pushed in the opposite direction, and can provide a closing force on the wound. In some embodiments, the barbs can be polymer, glass, metal, fine hair like structures, and/or other barbs known in the art. In some embodiments, the length of the barbs can be in the range of 0.1 mm to 5 mm (or about 0.1 mm to about 5 mm), for example 5 mm (or about 5 mm), 4 mm (or about 4 mm), 3 mm (or about 3 mm), 2 mm (or about 2 mm), or 1 mm (or about 1 mm). In some embodiments, the spacing of the barbs can be in the range of 0.1 mm to 10 mm (or about 0.1 mm to about 10 mm), for example 10 mm (or about 10 mm), 8 mm (or about 8 mm), 6 mm (or about 6 mm), 4 mm (or about 4 mm), 2 mm (or about 2 mm), or 1 mm (or about 1 mm).

In some embodiments, the lip 216 is supplied with a means of attachment integrated within the upper surface 218. In some embodiments, the lip 216 upper surface 218 can be prepared prior to insertion into the body cavity with the attachment means. The surface of the lip that the barbs protrude from may be smooth to limit the formation of granulation tissue on the fascia. The tissue attachment mechanism on the lip 216 can be the same tissue attachment mechanism as used on the other components of the device. In other embodiments, the tissue attachment mechanism on the lip 216 can be of a different type than is used on the other components of the device. For example, a different type of tissue attachment mechanism may be used for attachment of the lip surface 218 to the fascia than is used for attachment of the outer surface 212 of the elongate layer to fat or other tissue.

Alternatively, in some embodiments, the wound securing material can comprise an elongate layer such as a tape, with or without a lip. The tape can surround the wound filler when in use. In some embodiments, the tape can contain adhesive, barbs, Velcro, hooks of Velcro, mushroom shaped hooks of Velcro, or other attachment mechanism known in the art on both sides. In other embodiments, the tape can have adhesive, barbs, Velcro, hooks of Velcro, mushroom shaped hooks of Velcro, or other attachment mechanism known in the art on the tissue facing side and an adhesive or other attachment mechanism known in the art on the wound filler facing side. In some embodiments, the barbs may be smooth rod like projections. Alternatively, in some embodiments, the barbs may have a rough surface or spiked surface to increase adhesion. In some embodiments, the length of the barbs can be in the range of 0.1 mm to 5 mm (or about 0.1 mm to about 5 mm), for example 5 mm (or about 5 mm), 4 mm (or about 4 mm), 3 mm (or about 3 mm), 2 mm (or about 2 mm), or 1 mm (or about 1 mm). In some embodiments, the spacing of the barbs can be in the range of 0.1 mm to 10 mm (or about 0.1 mm to about 10 mm), for example 10 mm (or about 10 mm), 8 mm (or about 8 mm), 6 mm (or about 6 mm), 4 mm (or about 4 mm), 2 mm (or about 2 mm), or 1 mm (or about 1 mm). In some embodiments, the barbs on the tape can be different sizes and shapes. In some embodiments, the barbs on the tape can be of the same size and shape.

FIG. 3A illustrates an embodiment of a wound securing material 200 comprising an elongate layer of material 210 with a lip 216 and a plurality of fingers 217 extending outwardly from the lip. The lip can have one or more outwardly extending fingers 217 protruding from the end of the lip 216. In some embodiments, the plurality of outwardly extending fingers 217 can be protruding from the end of the front surface 231 of the lip 216 as illustrated in FIG. 3A. In some embodiments, the fingers 217 can each have a distal end 240 and a proximal end 241 and a length extending from the distal end 240 to the proximal end 241. In some embodiments, the proximal end 241 of each finger 217 can be attached to the front surface 231 of the lip 216. In some embodiments, the lip 216 is formed with fingers 217 protruding from the front surface 231 of the lip 216. In some embodiments, the finger 217 can be a foam material. In some embodiments, the fingers 217 can comprise a foam material different from the material used for the elongate layer, the lip, and/or other components of the device. In other embodiments, the fingers can comprise a foam material similar or the same as the material used for the elongate layer, the lip, and/or other components of the device, or any other foam described herein. In some embodiments, the foam used for the fingers can be compressed as described herein. In some embodiments, the foam material used for the fingers 217 can be a foam having a porosity in the range of 60 ppi to 200 ppi (or about 60 ppi to about 200 ppi), or greater than 60 ppi (or about 60 ppi) to minimize granulation tissue formation.

In some embodiments, the fingers or even portions of the wound securing material such as the lip 216 can be made of a 3D fabric instead of foam, for example a knitted or woven spacer fabric (such as a knitted polyester 3D fabric, Baltex 7970®, or Gehring 879®) or a nonwoven fabric. In some embodiments, the fingers or wound securing material can comprise other materials that can remain porous when compressed, including non-woven materials and/or other materials described herein or known in the art. In some embodiments, the fingers 217 can be formed from a non-porous material. Additionally, in some embodiments, the fingers 217 can be a flexible material, for example a flexible polymer material. In some embodiments, as the fingers 217 extends outward from the lip 216, the fingers 217 can have varying a rigidity, for example near the lip 216 at the proximal end 241 the fingers 217 can be rigid, but as the fingers 217 extends outward radially from the lip 216 the fingers 217 can increase in flexibility and/or decrease in strength and the distal end 240 can be flexible. In some embodiments, as the fingers 217 extends outward from the lip 216, the fingers 217 can have varying thickness, for example the thickness of the fingers can be reduced along the length of the fingers 217 and the proximal end 241 can be thicker than the distal end 240. Additionally, in some embodiments, the fingers can be branched and/or contain cross members, for example cross members can extend from one finger to another finger thereby connecting the fingers. Further, in some embodiments, the fingers 217 can vary in the width, for example the fingers 217 can widen as it extends outward radially from the lip 216 and the distal end 240 can be wider than the proximal end 241. The widening of the finger can allow for greater fluid removal.

In some embodiments, the fingers 217 can be helpful to drain the abdomen because they are in contact with the wound site and/or extend into the rear of the abdomen. In some embodiments, the fingers 217 can assist in securing the lip 216 during use as the fingers 217 can be inserted between the fascia and the internal organs as described further below. In some embodiments, the fingers 217 can extend into the rear of the abdomen thus draining fluid from the majority of the abdominal cavity. For example, the fluid may travel along the length of the fingers towards the point of application of negative pressure thereby draining fluid from the abdominal cavity.

Additionally, the surface of the fingers 217 can be in contact with the interior of the wound site and body cavity. Such interaction of the finger 217 surface with the interior of the body may cause the formation of granulation tissue. In some embodiments, the fingers 217 can be formed from a foam with a porosity in the range of 60 ppi to 200 ppi (or about 60 ppi to about 200 ppi) to prevent granulation of tissue. FIG. 3B illustrates an embodiment of a wound securing material with fingers as described with reference to FIG. 3A, but the fingers as illustrated in FIG. 3B can be surrounded by an organ protection layer 305. In some embodiments, the fingers 217 can be encapsulated by an organ protection layer 305 that has a plurality of fluid drainage openings or slits that prevents granulation tissue and other undesired interactions between the fingers and the body cavity interior. In some embodiments, the organ protection layer 305 surrounding the fingers 217 can be microporous or semipermeable, for example a dialysis membrane. In some embodiments, the organ protection layer 305 may serve to increase strength of the fingers 217 and thereby reduce the chance of parts being left in the body due to tearing during removal.

Figure 4:
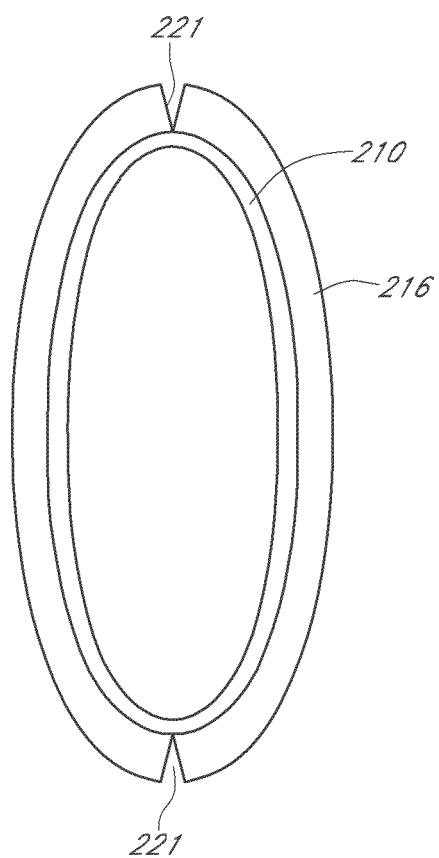
FIG. 4 illustrates a top view of an embodiment of a wound securing material.
Figure 5:
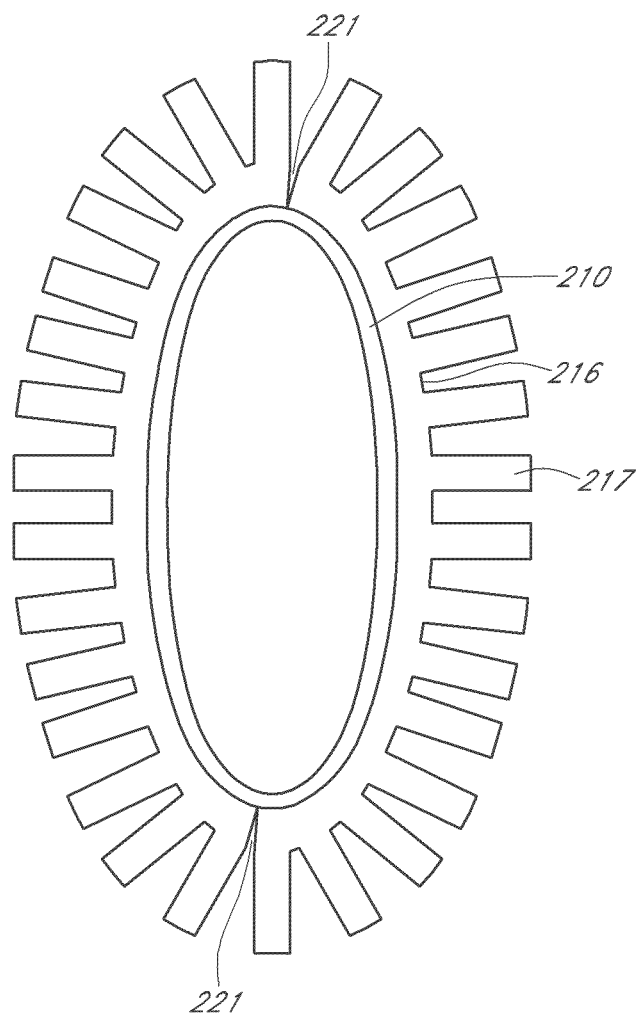
FIG. 5 illustrates a top view of an embodiment of a wound securing material with fingers.

FIG. 4 illustrates the top view of an embodiment of a wound securing material 200 similar to FIG. 2C comprising an elongate layer 210 formed into or having an annular shape with an outwardly extending lip 216 and slits 221. FIG. 5 illustrates the top view of an embodiment similar to FIGS. 3A-3B of a wound securing material 200 formed into or having an annular shape with fingers 217 extending outwardly from the lip 216. In some embodiments, when the elongate layer 210 of FIG. 2A including the lip 216 is bent into an angular shape and the first end 214 and end second end 215 are attached, the elongate layer can form an annular shape as illustrated in the top view shown in FIG. 4. Additionally, in some embodiments, when the elongate layer 210 including the lip 216 and outwardly protruding fingers 217 of FIG. 3A-3B is bent into an angular shape and the first end 214 and end second end 215 are attached, the elongate layer can form an annular shape as illustrated in the top view shown in FIG. 5.

Figure 6A:
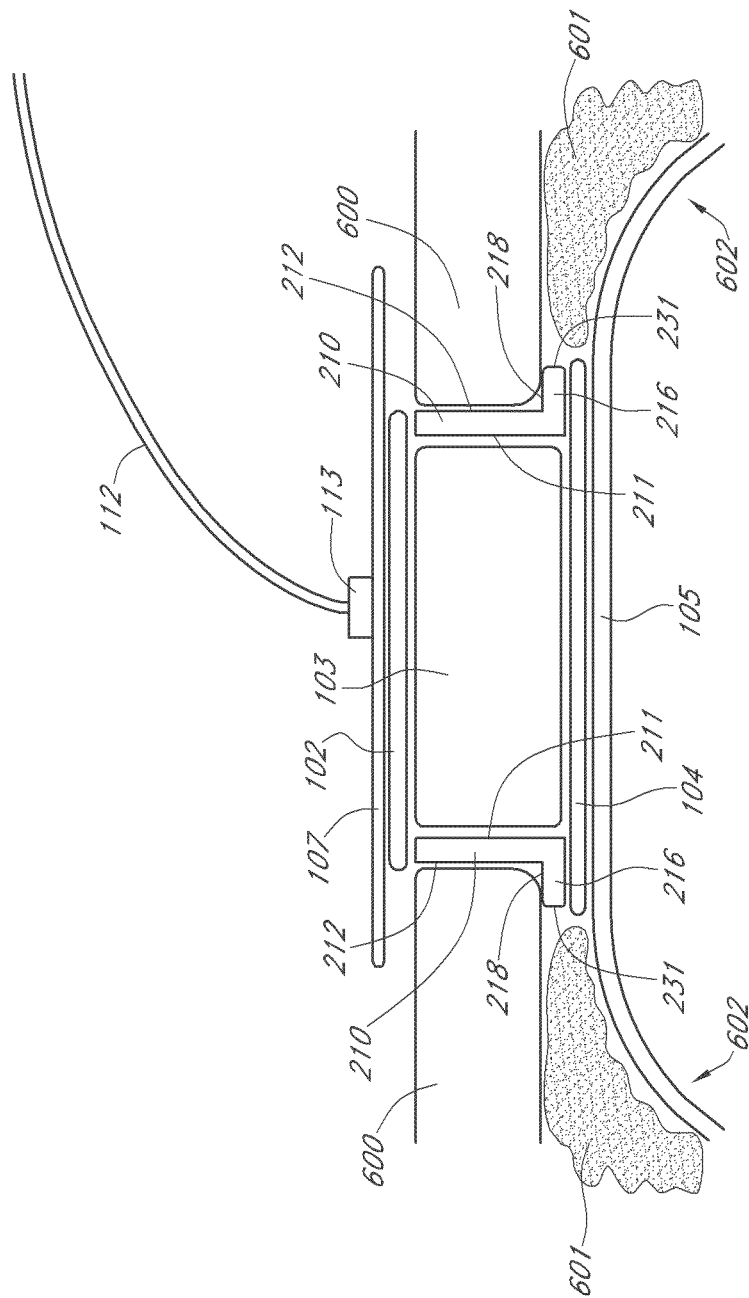
FIG. 6A illustrate a partial cross sectional view of an embodiment of a negative pressure wound therapy system comprising a wound securing material with an elongate layer and a lip.
Figure 6B:
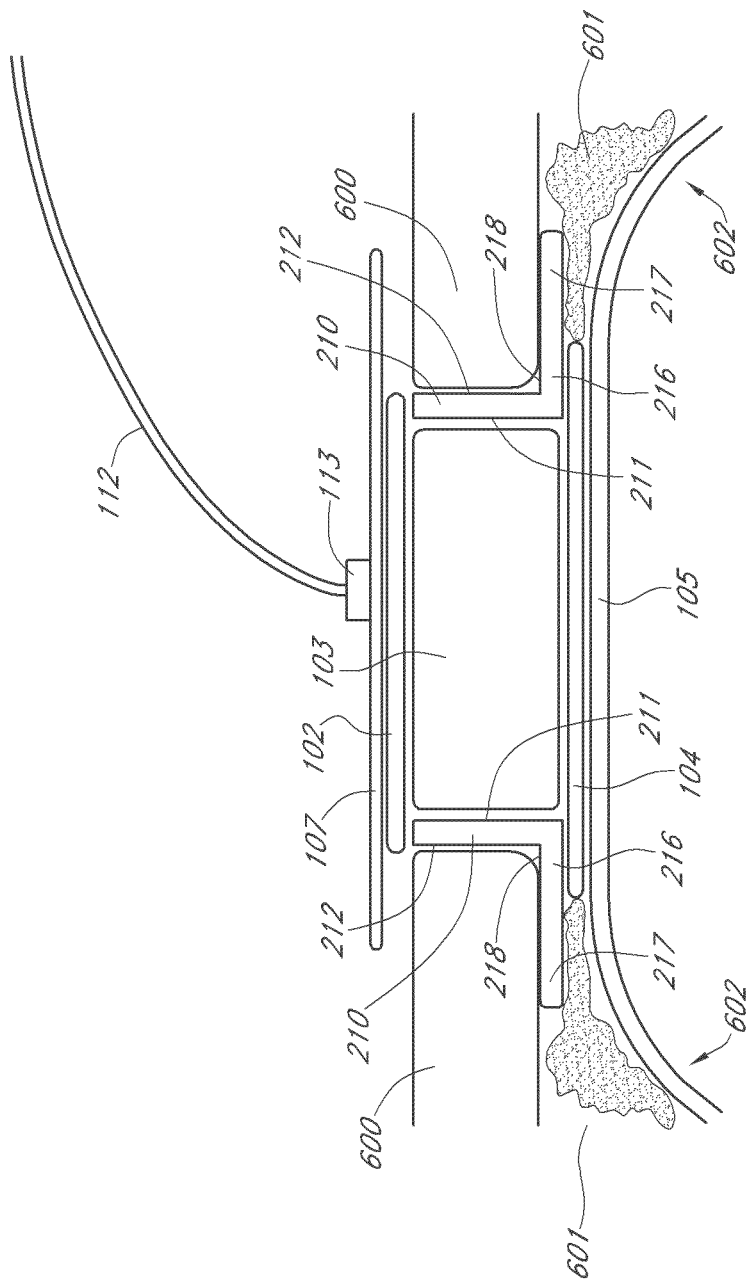
FIG. 6B illustrate a partial cross sectional view of an embodiment of a negative pressure wound therapy system comprising a wound securing material with an elongate layer, a lip, and fingers.
Figure 6C:
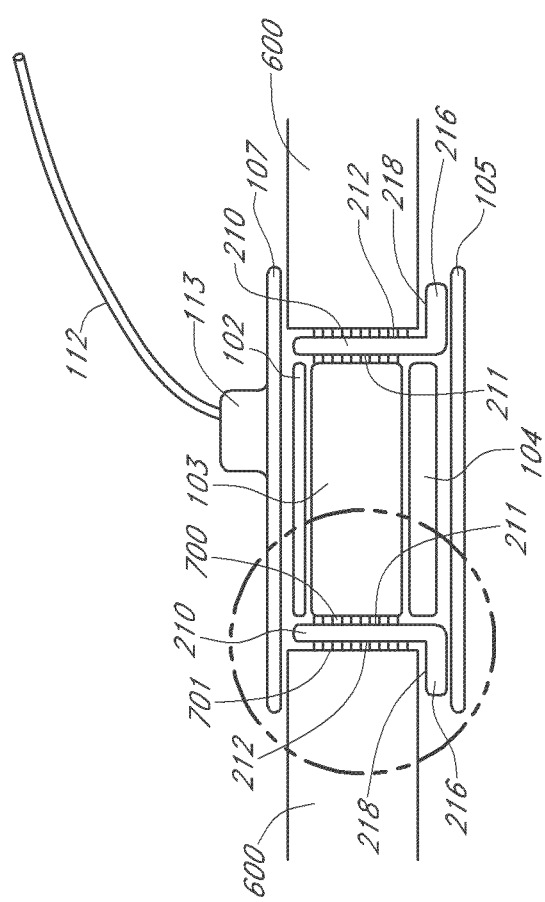
FIG. 6C illustrate a partial cross sectional view of another embodiment of a negative pressure wound therapy system, wherein a wound securing material comprises attachment mechanisms.

FIGS. 6A-6C illustrate a cross sectional view of the negative pressure system 101 with the components described with respect to FIG. 1 as applied to a wound. FIG. 6A illustrates a cross sectional view of the wound securing material 200 similar to the FIG. 2A-E embodiments within the wound area. In some embodiments, an organ protection layer 105 can be positioned in the wound site as shown in FIG. 6A. In some embodiments, the organ protection layer 105 can extend radially beyond the foam layer 104 and the outer ends 602 of the organ protection layer can be inserted beneath the abdominal wall 601. In some embodiments, the organ protection layer can have a length in the range of 900 mm (or about 900 mm) or less, 800 mm (or about 800 mm) or less, 700 mm (or about 700 mm) or less, and 600 mm (or about 600 mm) or less.

Figure 6D:
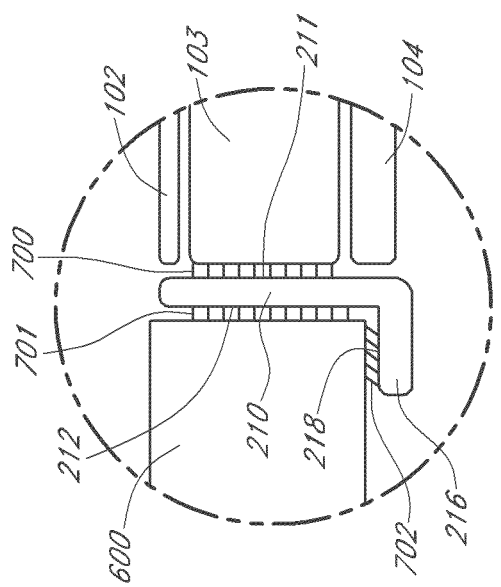
FIG. 6D is an enlarged view of an embodiment of a wound securing material positioned within a wound comprising attachment mechanisms.
Figure 8A:
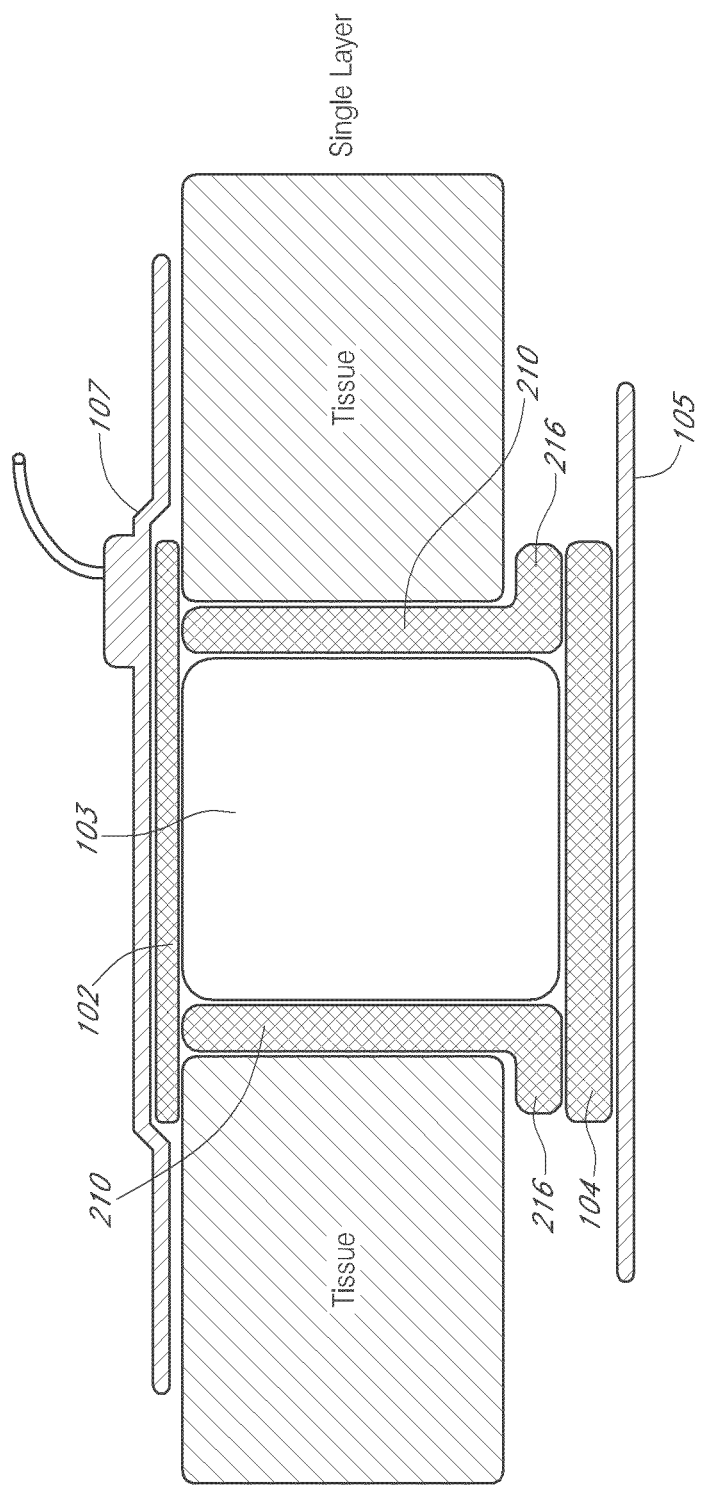
FIGS. 8A-H illustrate a partial cross sectional view of embodiments of a negative pressure wound therapy system comprising a wound securing material with an elongate layer and a lip.

In some embodiments, foam layer 104 can be provided above the organ protection layer 105. The foam layer 104 can be a foam as described herein or other foam known in the art. In some embodiments, the foam can have a thickness in the range of 1 mm to about 20 mm (or about 1 mm to about 20 mm), for example 15 mm (or about 15 mm) or less, 10 mm (or about 10 mm) or less, or 5 mm (or about 5 mm) or less. In some embodiments, the outer perimeter or boundary of the foam 104 will not extend beyond the front surface 231 of the lip 216 of the wound securing material 210. In some embodiments, the foam layer 104 will extend to the front surface 231 of the lip 216. In some embodiments, the foam 104 will not protrude out under the tissue 600 of the wound site. In some embodiments, the foam 104 can extend beyond the front surface 231 of the lip 216 as shown in FIG. 8A. In some embodiments, the foam layer 104 can be at least partially surrounded by the elongate layer 210 and/or lip 216 of the wound securing material 200 as illustrated in FIG. 6C-6D.

In some embodiments, the wound filler 103 can be placed above the foam layer 104 and below the foam layer 102. In some embodiments, the wound filler can be a wound filler as described herein or other foam known in the art. In some embodiments, the wound filler can have a thickness of the range of 5 mm to 40 mm (or about 5 mm to about 40 mm), for example 40 mm (or about 40 mm) or less, 30 mm (or about 30 mm) or less, or 10 mm (or about 10 mm) In some embodiments, the wound filler can have a thickness on the lower end of the range for use in neonatal applications. Additionally, the wound filler 104 can be used in combination with other wound filler stacked within the wound site for larger or deeper wounds. In such embodiments, such additional wound filler can also be surrounded by an additional wound securing material as described herein. In some embodiments the additional wound securing material surrounding the wound fillers stacked above the bottom wound filler can be an elongate layer without finger protrusions. In some embodiments the additional elongate layers surrounding the wound fillers stacked above the bottom wound filler can be an elongate layer without a lip.

In some embodiments, the wound filler can be surrounded by the elongate layer 210. The elongate layer 210 can have a lip 216. The elongate layer 210 and lip 216 can be any embodiment of an elongate layer and/or lip as described herein. The lip 216 of the elongate layer 210 can extend under the tissue 600. In some embodiments, the lip 216 can be inserted beneath the layer of tissue 600 in which a closing force is desired to close the wound cavity. In some embodiments, the lip can extend beneath the deep fascia, subserous fascia, serous membrane, peritoneum, or any other layer between the dermal layers and the viscera. For example, in one embodiment, for abdominal wounds, the lip can preferably be placed beneath the peritoneum. The use of the lip may therefore facilitate maintaining and retaining the wound filler at the correct vertical level within the wound. The lip can have a length in some embodiments between 5 mm and 60 mm (or about 5 mm and about 60 mm), for example 60 mm (or about 60 mm) or less, 50 mm (or about 50 mm) or less, 40 mm (or about 40 mm) or less, 30 mm (or about 30 mm) or less, or 10 mm (or about 10 mm) or less. The attachment mechanisms on the lip 216 can thus be used to facilitate movement of the fascia as the wound closes.

During use in the wound cavity, the elongate layer 210 with the lip 216 surrounds the wound filler 103. In some embodiments, the wound filler 103 can be wrapped with and attached to the elongate layer 210 with the lip 216 prior to insertion of the unit into the body cavity. Additionally, the elongate layer 210 with the lip 216 and the wound filler 103 can be one integral piece of material. Alternatively, in some embodiments, the elongate layer 210 with the lip 216 can be cut and shaped into the appropriate size for the wound site 110 and then placed within the wound site. Then the wound filler 103 can be placed within and attached to the inner surface 211 of the elongate layer 210 with the lip 216. The inner surface 211 of the elongate layer 210 can contact the wound filler 103 and the outer surface of the elongate layer 212 and the lip can contact the interior of the wound site. The inner surface 211 and the wound filler 103 can be attached through the attachment means described herein and other attachment means known in the art.

In some embodiments, a foam layer 102 can be provided above the wound filler 103. The foam layer 102 can comprise a foam as described herein or other foam known in the art. In some embodiments, the foam can have a thickness in the range of 1 mm to about 20 mm (or about 1 mm to about 20 mm), for example 15 mm (or about 15 mm) or less, 10 mm (or about 10 mm) or less, or 5 mm (or about 5 mm) or less. In some embodiments, the outer boundary of the foam 102 will not extend beyond the outer surface 212 of the elongate layer 210. In some embodiments, the foam 102 will extend to the outer surface 212. In some embodiments, the foam 102 can extend beyond the outer surface 212 as shown in FIG. 8A. In some embodiments, the foam 102 can be at least partially surrounded by the elongate layer 210 and/or lip 216 as illustrated in FIG. 6C-6D.

In some embodiments, the foam layer 102 is covered by a wound cover 107. The wound cover 107 can include all embodiments of a wound cover described herein and other wound covers known in the art. A port 113 and a conduit 112 may be used to connect the wound cover to a source of negative pressure as described above.

FIG. 6B illustrates a cross sectional view similar to that described in FIG. 6A, however, FIG. 6B illustrates the elongate layer 210 with fingers 217 as described with respect to FIG. 3 protruding outwardly from the lip. In some embodiments, the fingers 217 can have a length in the range of 100 mm to about 300 mm (or about 100 mm to about 300 mm), for example, 250 mm (or about 250 mm) or less, 200 mm (or about 200 mm) or less, or 150 mm (or about 150 mm) or less. In some embodiments, the lip 216 and fingers 217 can be inserted beneath the layer of tissue 600 in which a closing force is desired to close the wound cavity. In some embodiments, the lip and fingers 217 can extend beneath the deep fascia, subserous fascia, serous membrane, peritoneum, or any other layer between the dermal layers and the viscera. For example, in one embodiment, for abdominal wounds, the lip can preferably be placed beneath the peritoneum.

FIG. 6C illustrates an alternative embodiment of a cross sectional view of the elongate layer within the wound area similar to that described with reference to FIG. 6A. FIG. 6C further illustrates an elongate layer 210 and with an attachment mechanism 700 for attachment of the elongate layer to the wound filler material. The attachment mechanism 700 can be achieved through any of the means described herein and other attachment mechanisms known in the art. Additionally, FIG. 6C further illustrates an attachment mechanism 701 for attachment of the elongate layer outer surface 212 to the wound site. The attachment mechanism 701 can be achieved through any of the means described herein and other attachment mechanisms known in the art.

FIG. 6D illustrates an elongate layer 210 with an attachment mechanism 702. In some embodiments, the outer surface 212 of the elongate layer can be attached to the wound site through tissue attachment means described herein and other tissue attachment means known in the art. In some embodiments, the upper surface 218 of the lip 216 can be attached to the wound site through tissue attachment means described herein and other tissue attachment means known in the art. The attachment mechanism 702 can be achieved through any of the means described herein and other attachment mechanisms known in the art. In some embodiments, the attachment mechanisms 700, 701, and 702 can utilize the same attachment means. Alternatively, in some embodiments, the attachment mechanisms 700, 701, and 702 can utilize different attachment means.

In some embodiments, the lip 216 can extend outwardly into the wound cavity. The top surface of the lip 216 can be situated under the peritoneum or fascia of the patient. In some embodiments, the lip 216 can be inserted into the wound site 110 by the medical professional or user manipulating the lip 216 with their fingers to get the lip 216 under the peritoneum. The optional tissue attachment mechanism on the top surface of the lip can adhere the lip to the wound site and secure the lip 216 as shown in FIG. 6D. The secure connection of the elongate material 210 through the secure connection of the lip 216 to the wound site 110 can ensure the correct positioning of the wound filler 103 attached to the inner surface 211 of the elongate material 210. In some embodiments, the lip 216 can assist in providing structural stability to the device and prevent the wound filler or device from coming out of the wound site. Additionally, the barb or grippers on the lip 216 may also produce traction to pull the bottom of the wound together.

In some embodiments, the bottom surface of the lip 216 can be in contact with a bottom foam layer 104 and/or an organ protection layer 105, depending on the components used and the dimensions of those components. In some embodiments, it can be preferable that the lip 216 and/or fingers 217 are not in direct contact with the organs themselves and/or the lip 216 and/or finger 217 can be surrounded by an organ protection layer or have an organ protection layer placed between the lip 216 and/or the fingers 217 and the viscera.

Figure 7:
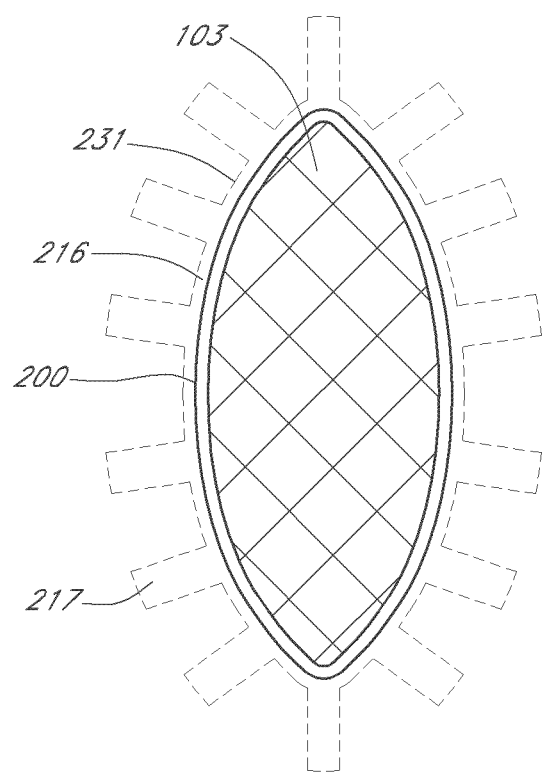
FIG. 7 illustrates a top view of an embodiment of a wound filler and wound securing material placed within a wound.

FIG. 7 illustrates a top view of a wound filler 103 inserted into a wound 110 with a wound securing material 200 such as described in FIGS. 3A-3B surrounding the wound filler. The front surface 231 of the lip 216 and the fingers 217 are illustrated in phantom lining to depict that the lip 216 and the fingers 217 are located radially outward from the wound edge and placed underneath the fascia.

Figure 8B:
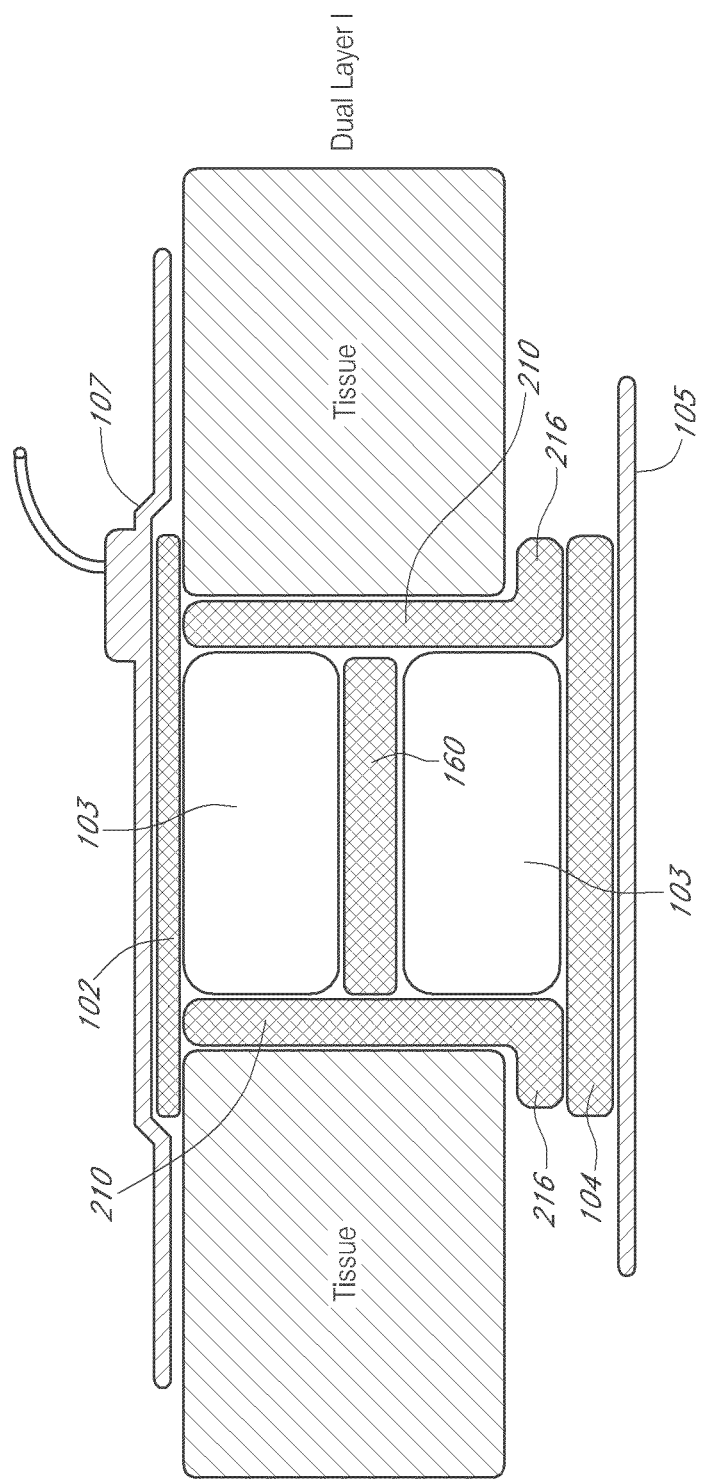

FIGS. 8A-H illustrate a partial cross sectional view of embodiments of a negative pressure wound therapy system comprising a wound securing material with an elongate layer and a lip. The negative pressure wound therapy systems comprising a wound securing material illustrated in FIGS. 8A-B are similar to the system described with reference to FIG. 6A. FIGS. 8A-B further illustrate the foam 102 extending beyond the elongate layer 210 and in contact with the top surface of the tissue. Additionally, FIG. 8B illustrates an embodiment comprising two wound filler materials 103 separated by an additional foam layer 160. In some embodiments, the two wound filler materials 103 and the additional foam 160 can be surrounded by the elongate layer 210 and lip 216.

Figure 8C:
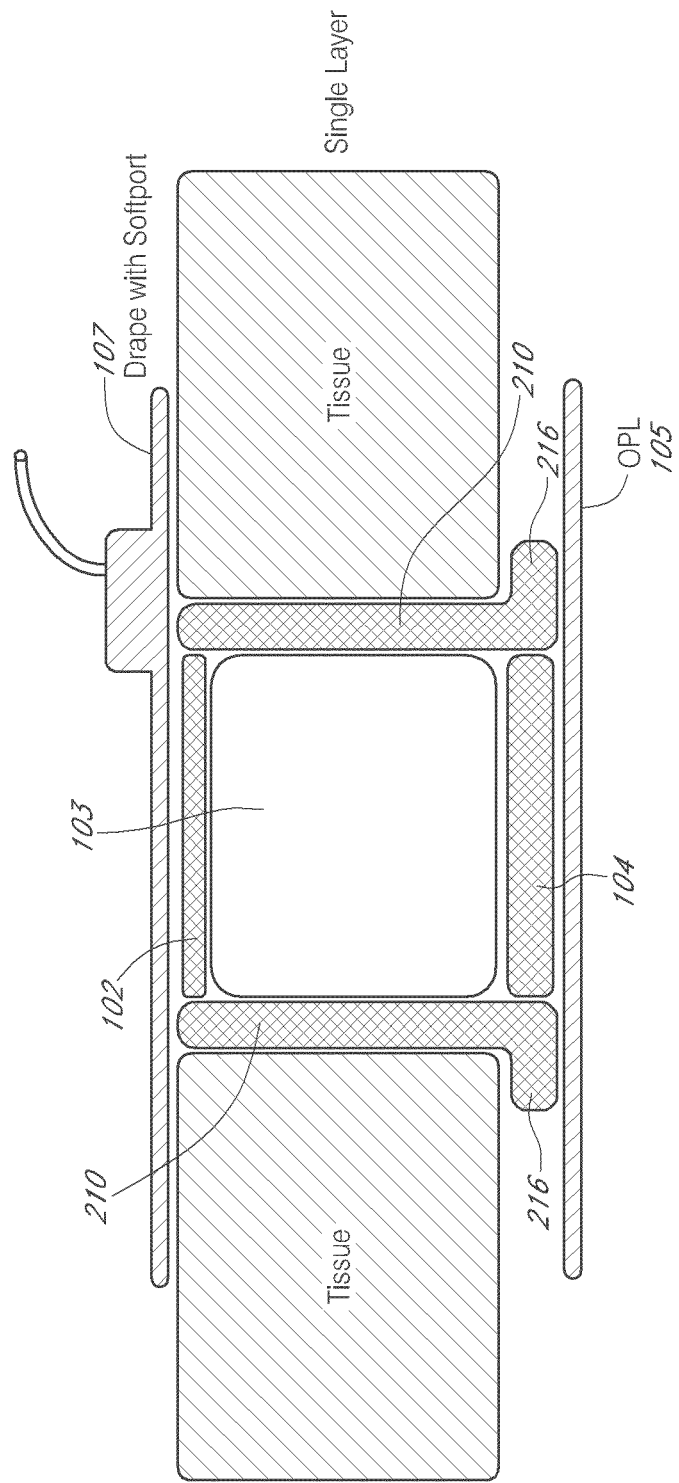
Figure 8D:
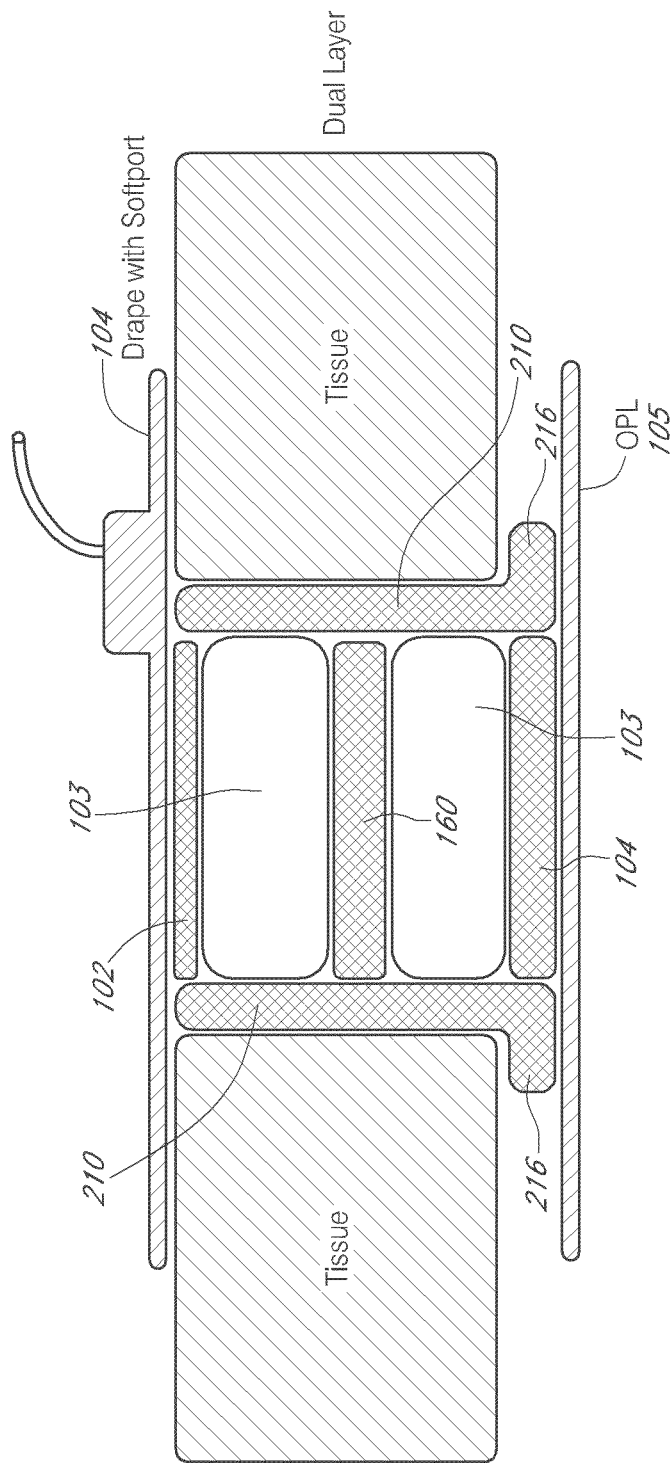

FIGS. 8C-D illustrate embodiments of negative pressure wound therapy systems comprising a wound securing material similar to that described with reference to FIG. 6A. FIGS. 8C-D further illustrate the foam layers 102, 104 at least partially surrounded by the elongate layer 210 and/or lip 216. Further, FIG. 8B illustrates an embodiment comprising two wound filler materials 103 separated by an additional foam layer 160. In some embodiments, the two wound filler materials 103 and the additional foam 160 can be surrounded by the elongate layer 210 and lip 216.

Figure 8E:
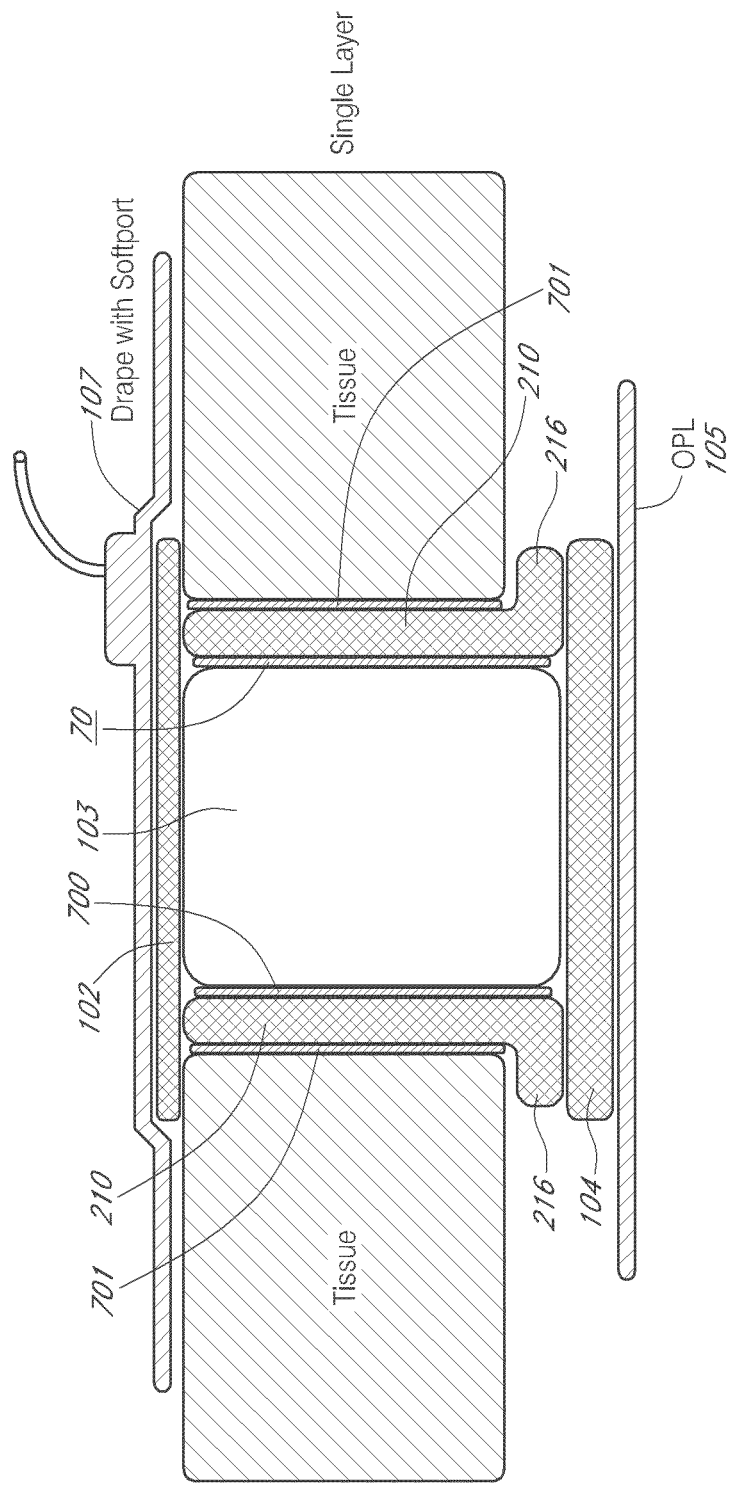
Figure 8F:
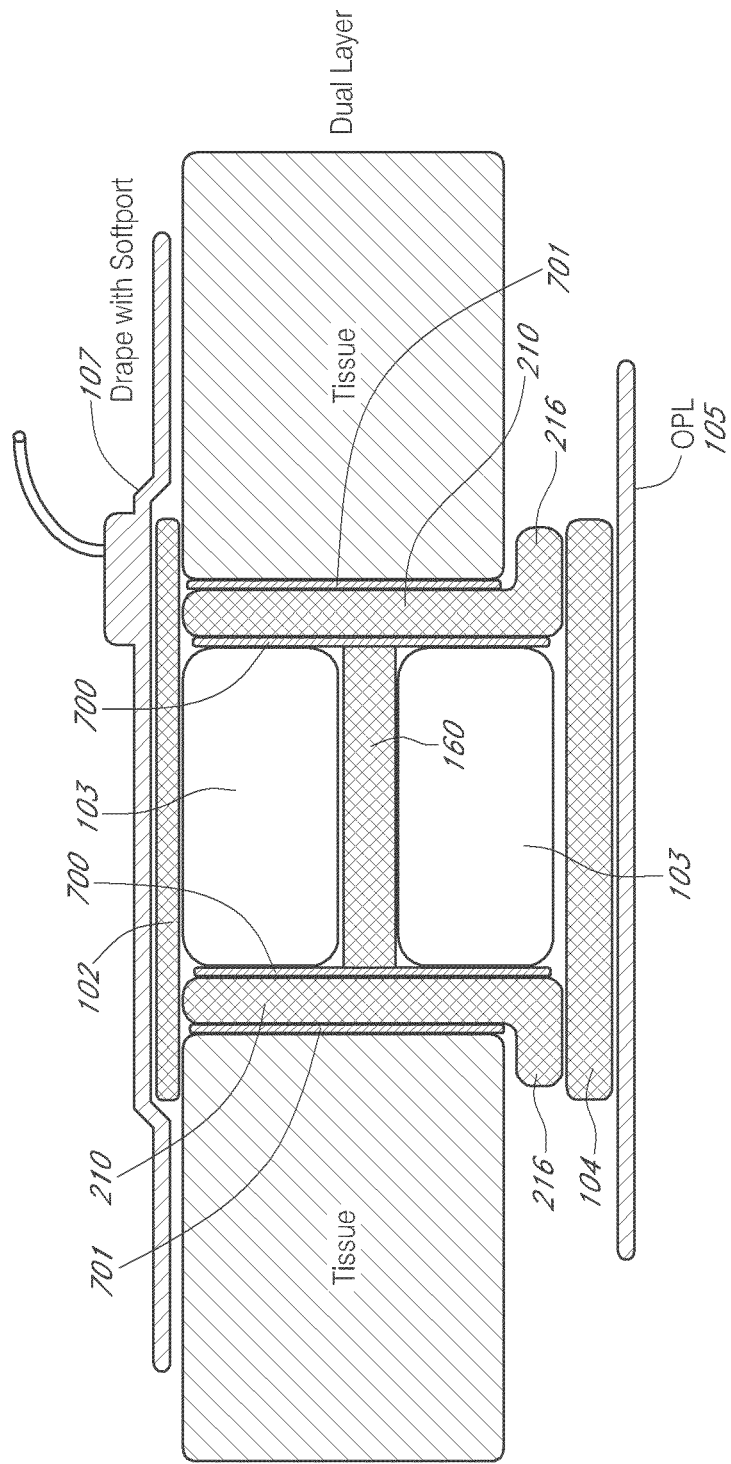

FIGS. 8E-F illustrate embodiments of negative pressure wound therapy systems comprising a wound securing material similar to that described with reference to FIGS. 8A-B. FIGS. 8E-F further illustrate the use of grippers and/or attachment mechanisms 700, 701 as described with reference to FIG. 6C.

Figure 8G:
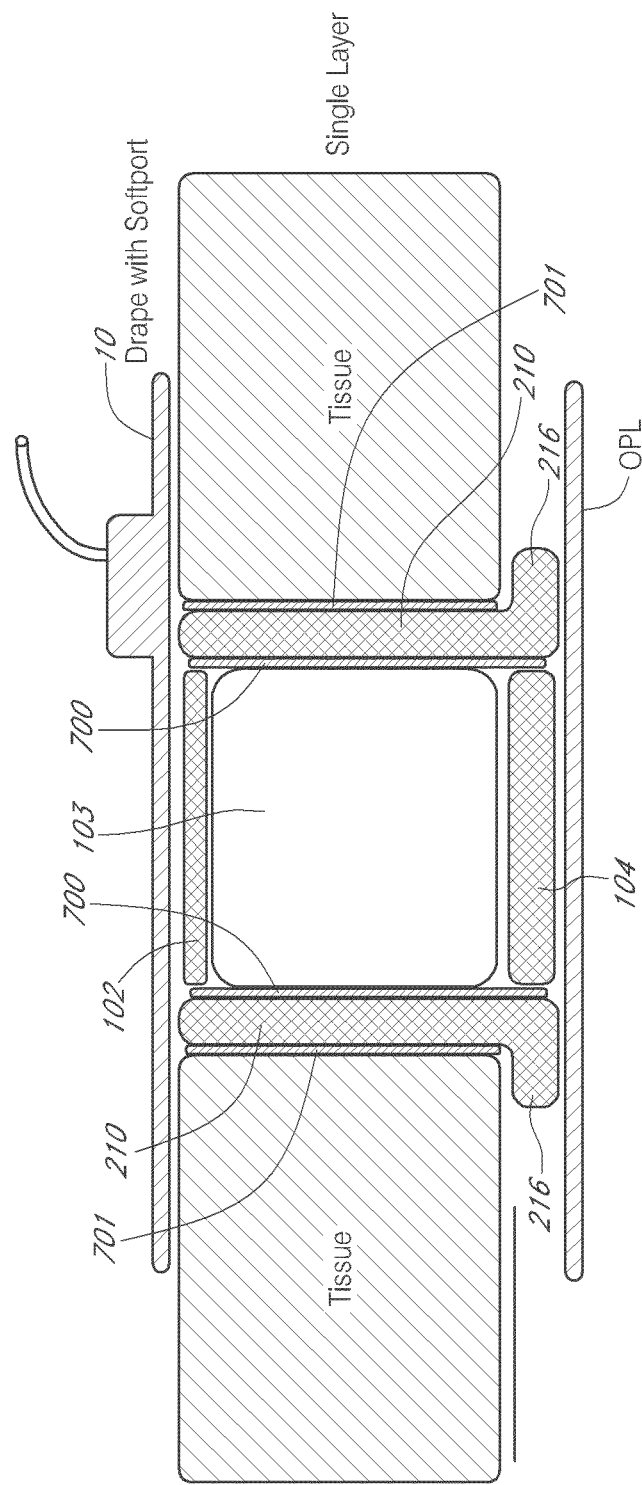
Figure 8H:
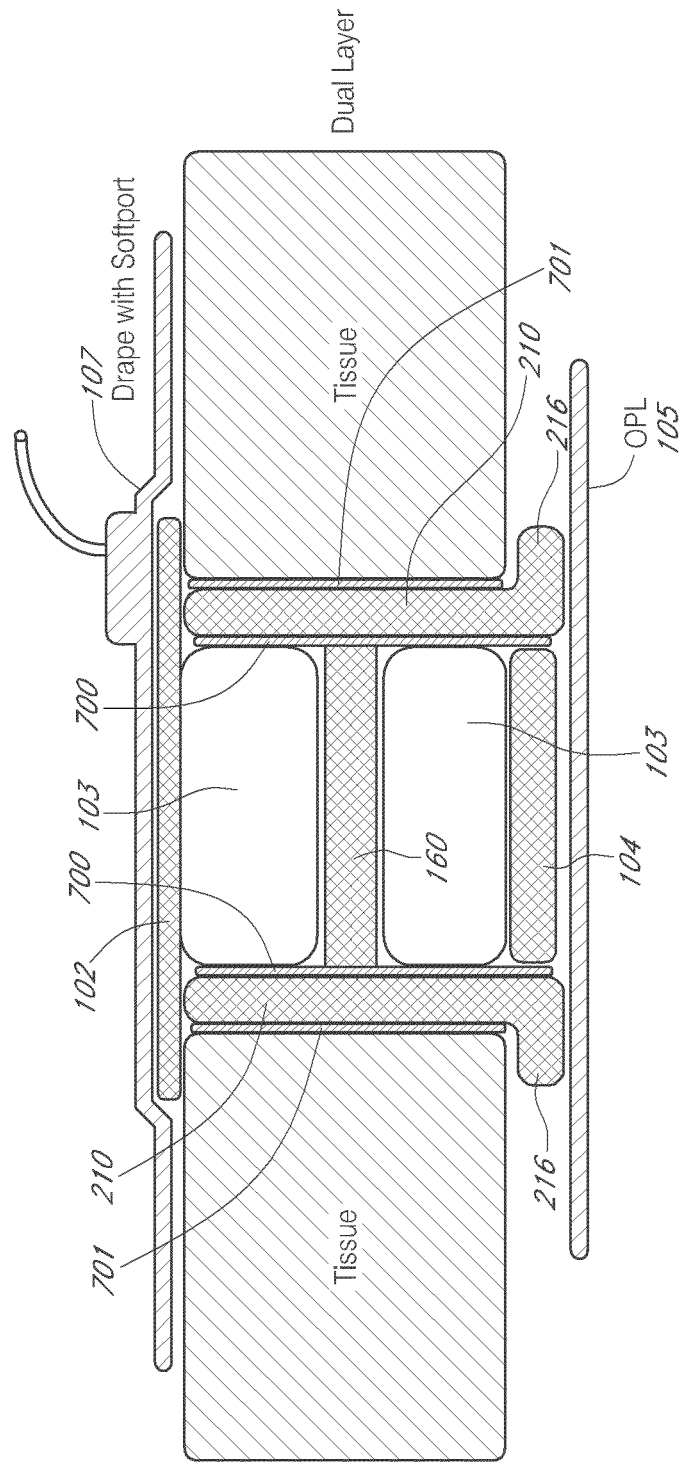

FIGS. 8G-H illustrate embodiments of negative pressure wound therapy systems comprising a wound securing material similar to that described with reference to FIGS. 8C-D. FIGS. 8G-H further illustrate further illustrate the use of grippers and/or attachment mechanisms 700, 701 as described with reference to FIG. 6C.

Figure 8I:
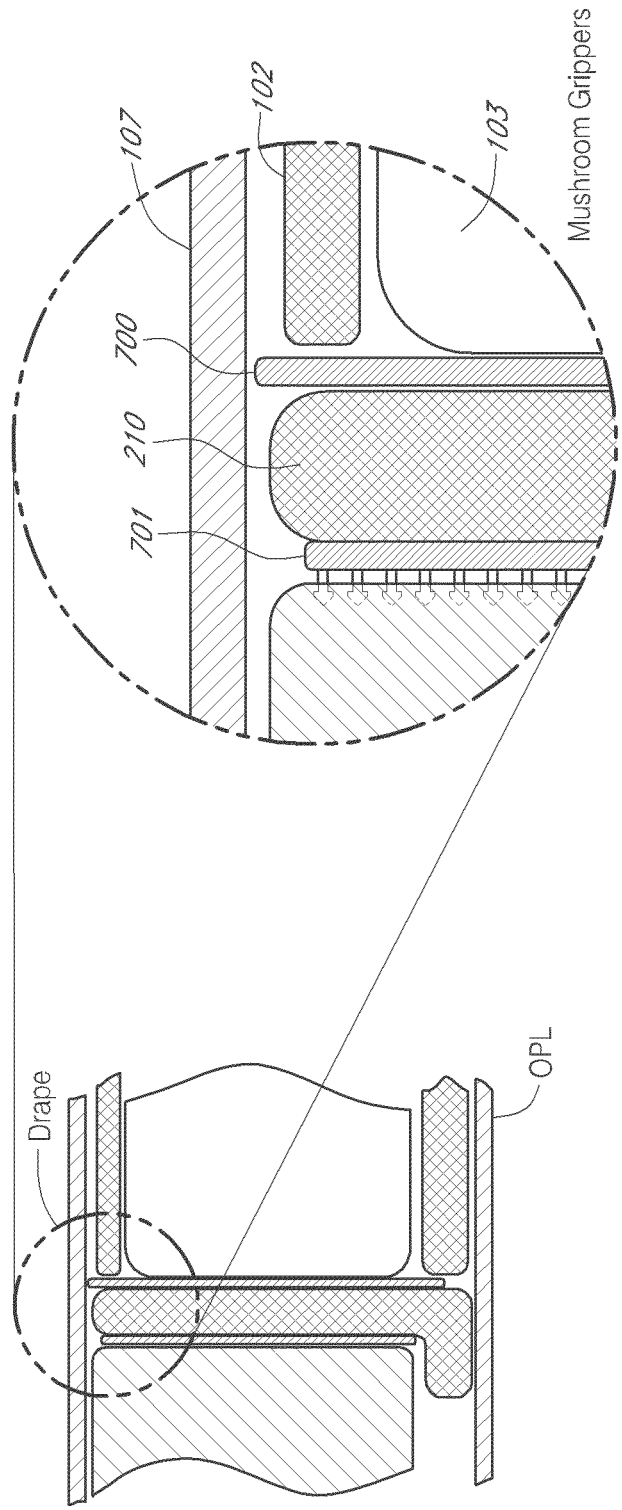
FIGS. 8I-K are an enlarged view of an embodiment of a wound securing material positioned within a wound comprising various attachment mechanisms.
Figure 8J:
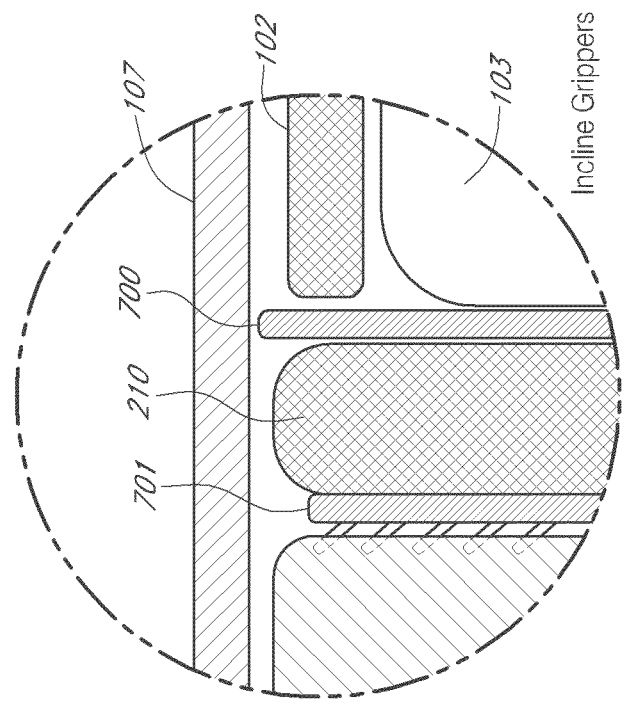
Figure 8K:
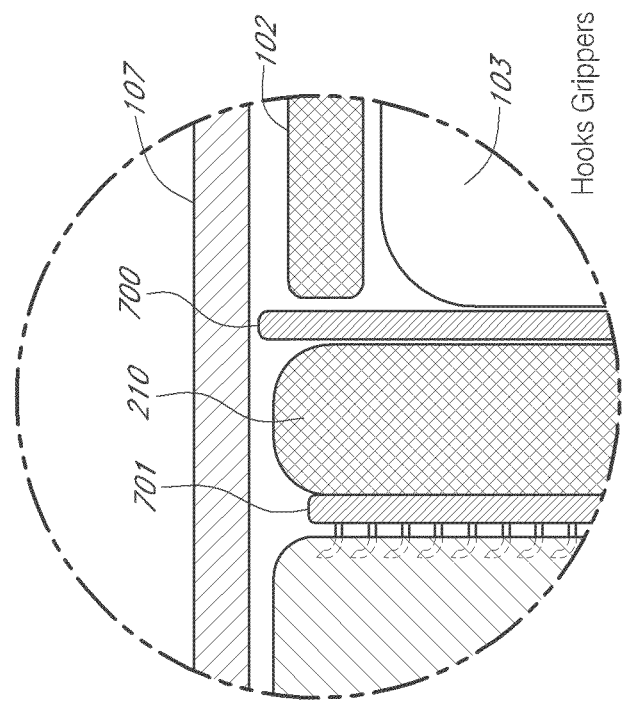

FIGS. 8I-K are enlarged views of embodiments of a wound securing material positioned within a wound comprising attachment mechanisms 701, 700. In some embodiments, the attachment mechanisms 701 can be mushroom grippers as illustrated in FIG. 8I. In some embodiments, the attachment mechanisms 701 can be incline grippers as illustrated in FIG. 8J. In some embodiments, the attachment mechanisms 701 can be hook grippers as illustrated in FIG. 8K.

In some embodiments, the elongate material 210 can be in the form of a strip without a lip. The elongate layer without a lip can have fingers that extend directly from the outer surface 212 of the elongate material 210. These fingers extending directly from the elongate layer can contact the tissue and be placed beneath the fascia and/or any other layer or configuration as described herein. In some embodiments, the fingers 217 extending directly from the elongate layer 210 without the lip can support and secure the wound securing material 200 and provide the functionality of the elongate layer with the lip as described herein.

In some embodiments, the elongate material 210 can have more than one lip 216 extending outwardly from the elongate material. In one embodiment, the elongate layer can have two separate lip regions extending outwardly from the outer surface of the elongate layer that can be positioned at different depths in the wound. For example, one lip can extend laterally from the elongate layer and can be placed between the abdominal cavity and the fascia while a second lip can be positioned between the fascia and overlying tissue.

Figure 9A:
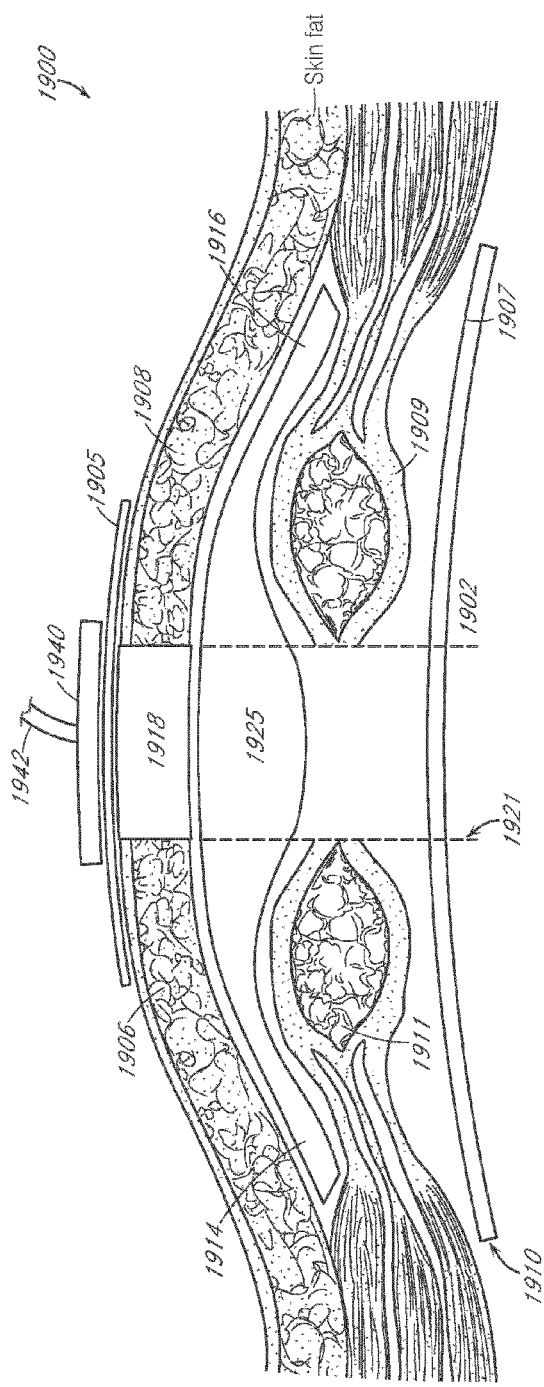
FIG. 9A illustrates a cross sectional view of a pad and wound filler at a surgical site in accordance with a preferred embodiment of the invention.
Figure 9B:
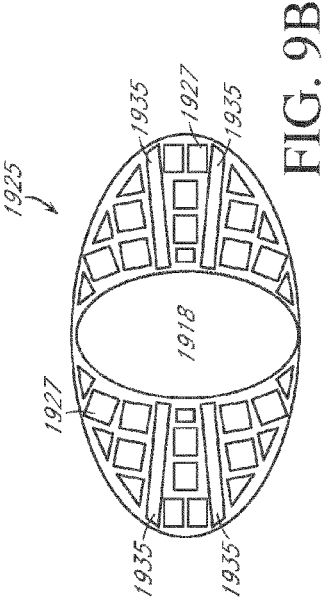
FIG. 9B illustrates a top view of a wound filler and a tissue adhesion device.
Figure 9C:
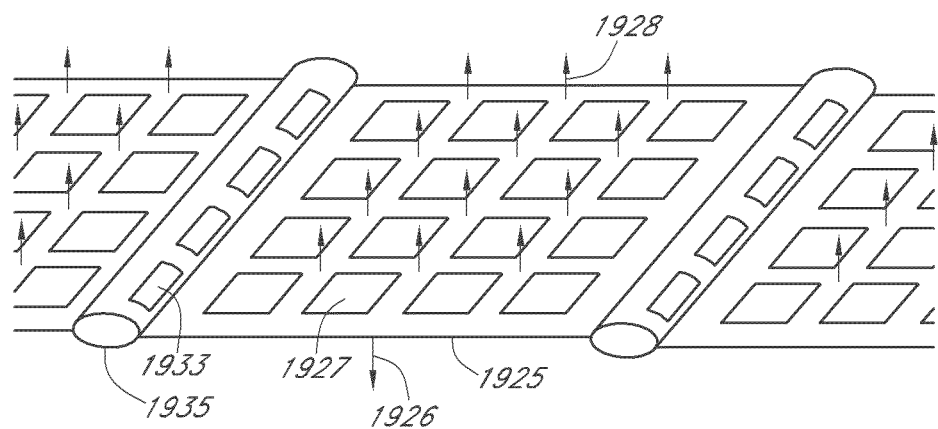
FIG. 9C shows a detailed perspective of a surgical drainage system in accordance with a preferred embodiment of the invention.

In the embodiments described above, the elongate material 210 and lip 216 are preferably integrally formed or attached to one another such that the elongate material and lip are integrated into a single piece to be placed in the wound simultaneously. The elongate material may also be pre-attached to any of the wound fillers described herein, such that the wound filler, elongate material and lip are placed in the wound simultaneously. FIG. 9A-9C illustrate another embodiment where a wound 1900 is treated using a wound filler in a negative pressure region 1918 that is a separate element from an underlying pad 1925 that extends laterally beyond the edges of the wound filler 1918. The pad 1925 in FIG. 9A is illustrated as being positioned between the fascia and overlying tissue, but in other embodiments, the pad 1925 may be positioned underneath the fascia. The pad 1925 also need not be a separate element from the filler 1918, and may be attached to the filler or be formed integral with the filler. It will further be appreciated that features of the pad 1925, such as the drain tubes, apertures and tissue anchors described further below, can also be incorporated into the lip 216 that may be integral with the elongate material 210 described above.

Illustrated in FIG. 9A is a wound incision 1900 in which tissue regions 1906, 1908 have been separated to access an underlying tissue region 1902 for treatment. The lateral displacement of regions 1906, 1908 from their respective positions overlying region 1902 has caused further separation between the displaced regions 1906, 1908 and the underlying structure. In the case of an open abdominal wound, the underlying structure can be the large and small intestines, which can be subject to infection and/or elevated fluid pressure.

Additionally, there can be separation between the fascia 1909, 1911 and abdominal muscle and the overlying subcutaneous tissue 1906, 1908. Consequently in FIG. 9A, the system can optionally include three components, the pad 1907 positioned between the abdominal cavity 1902 and the fascia that can be used to permit sliding movement and utilize negative pressure, secondly, a pad 1925, described in greater detail hereinafter, positioned between the fascia and overlying tissue and, thirdly, the wound filler 1918. The negative pressure region of the wound filler 1918 can be in fluid communication with the underlying layer of the pad 1925, which extends laterally to sections 1914 and 1916 which are situated between overlying tissue 1906, 1908, respectively, and the underlying abdominal muscle and fascia structure 1911, 1909. One or both sides of the sections 1914, 1916 can have tissue anchors as described herein. Dotted line 1921 indicates a region through which negative pressure is applied to all three layers.

After insertion of pad 1925, the compressible wound filler 1918 is inserted followed by the wound cover 1905 and the port 1940 and conduit 1942. The pad 1907 operates to drain fluid 1910 from the abdominal cavity by negative pressure through pad 1925 and wound filler 1918.

In some embodiments, the wound filler 1918 can be integral to or attached to the underlying layers. For example, the wound filler 1918 can be integral to the pad 1925. In some embodiments, the wound filler 1918 can be integral to or attached to both pad 1925 and pad 1907. In some embodiments, the system does not include the pad 1925. In such embodiments, the wound filler 1918 can be integral to or attached to pad 1907 which can be positioned between the abdominal cavity 1902 and the fascia. For example, in some embodiments, the pad 1907 can be positioned on top of the visceral peritoneal layer.

In one embodiment, as the wound filler 1918 collapses horizontally under the force of negative pressure as described herein, the attached pad 1907 and/or pad 1925 will also collapse horizontally. The horizontal collapse can cause pad 1907 and/or pad 1925 to slide relative to the tissue layer over which pad 1907 and/or pad 1925 is positioned. For example, in some embodiment, the wound filler 1918 is attached to the pad 1907 positioned over the visceral peritoneal layer. As the wound filler 1918 collapses horizontally under the application of negative pressure, the horizontal collapse can thereby cause the attached pad 1907 to slide over the visceral peritoneal layer.

In some embodiments, the wound filler 1918 can be attached to the underlying pad at substantially all points of contact between the wound filler 1918 and the underlying pad. In other embodiments, the wound filler 1918 can attach to the underlying pad 1925 and/or pad 1907 at one or more attachment points. In one embodiment, the wound filler 1918 can be attached to the underlying pad 1925 and/or pad 1907 only at a center attachment point. As the wound filler 1918 collapses horizontally, the wound filler 1918 would slide horizontally relative to the underlying pad 1925 and/or pad 1907 due to the center attachment point. In some embodiments, the wound filler 1918 can be attached to the underlying pad 1925 and/or pad 1907 by one or more ribs extending down the center of the wound filler 1918. The one or more ribs can extend downward from the center of wound filler 1918 and connect to pad 1925 and/or pad 1907. Additionally, in some embodiments, the wound filler 1918 can be attached to pad 1925 and/or pad 1907 by an adhesive.

In the case where adjoining tissues need treatment utilizing negative pressure or require stabilization such as by pad 1925, a wound treatment system can be used in combination with the systems and methods described herein. Shown in FIG. 9B is a top view of a system utilizing a wound filler 1918 as described generally herein and a pad 1925. The shape of pad 1925 can also be circular and be without apertures or tissue anchors, for example. The number of drains can be in a range of 6-10 that extend in a radial direction with uniform angular spacing between the drain elements.

Thus a preferred embodiment provides a pad or surgical drain device 1925 for promoting drainage of surgical wounds and wound closure. The drain device can include a plurality of drain tubes 1935 disposed on a substrate termed an "adhesion matrix," which is designed to promote tissue adhesion within the wound space. The adhesion matrix has a conformable configuration and is made of a compliant material having planar surfaces that can bend to adapt to the shape of the wound space.

In a preferred embodiment, the adhesion matrix contains a plurality of apertures 1927, or gaps in the matrix material, which allow tissue contact across the matrix, so as to promote adhesion and wound closure. Thus, a tissue surface on a first side of the matrix can directly contact a tissue surface on a second, or opposite, side of the matrix to promote rapid healing and stabilization of the wound. The number, size and distribution of the apertures 1927 extending through the matrix can be selected based on the geometry of the wound. For abdominal wounds, for example, the drain tubes can be positioned in a fan shaped array with a plurality of three or more tubes extending from a manifold. The matrix and/or the tubing can be cut or shaped by the user to conform to the shape of the wound. The matrix can also be used as a medication carrier to assist in the administration of a drug to a patient. The matrix can optionally include a layer of adhesive on at least a portion of any of its surfaces. The drain tubes can be removed from the device once drainage flow is sufficiently reduced, and the adhesion matrix can remain within the body, where it is degraded and absorbed over time, remaining in place to optimize tissue healing. The matrix can comprise a porous biodegradable polymer material. As the plurality of tubes extend from a single exit site into the wound with spaced apart distal ends, a user can readily remove all the tubes simultaneously from the wound.

As shown in more detail in FIG. 9C, the pad 1925 can include a tissue anchoring system, whereby the device is mechanically attached to surrounding tissues by an array of surface barbs or hooks 1926, 1928 or other attachment mechanism as described herein. These surface structures can be located on any exposed surface of the adhesion matrix. When the device is implanted, the surrounding tissues can be pressed against the barbs or hooks to embed them within the tissue and anchor the device. The use of surface barbs or hooks can be used in combination with a surgical adhesive, providing a much stronger bond between tissue layers than the adhesive alone, and providing temporary adhesion while the adhesive sets. The structure of the hooks can have various forms depending on the tissue they are intended to bind. Longer hooks can be used for loosely bound tissues such as fat or connective tissue, while shorter hooks can be used for denser tissues such as muscle. Anchors with more rigid stems can be utilized to penetrate denser tissues.

Another aspect of the invention is a system for negative pressure wound therapy. The system includes the drain device or pad coupled to a wound filler 1918 as described generally herein together with a vacuum source, such as a pump, and a tube connecting the vacuum source to the drain tubes of the drain device or pad. The system optionally also can include a fluid trap to collect drained fluid and a control unit to monitor and control the application of vacuum and the collection of fluid. Further components of the system can include a vacuum or pressure gauge, a flow meter, and a computer to monitor vacuum and flow and to regulate vacuum or flow. The pressure measurement can be used to control the level of applied pressure using a feedback control circuit. The wound filler 1918 can include the endoskeleton structure as described in International Application No. PCT/US2013/050698, and may include, for example the stabilizing structures described with reference to FIGS. 14-25G, having external ribs extending from the outer surface and flexure arms or beams that have an intrinsic restoring force that varies as a function of position of each flexure element. The different flexure elements can have different restoring forces depending upon their position within the structure. The endoskeleton accommodates expansion to fill the wound cavity and will collapse in a well-defined manner in response to the collapse of the wound under negative pressure. As described herein, foam or other filler material can be used within the flexure system. The endoskeleton can have a multilayered structure with the different layers collapsing along individual planes of the three dimensional structure within the wound without tilting of the structure. Any of the other embodiments of collapsible wound fillers described in International Application No. PCT/US2013/050698, titled "Negative Pressure Wound Closure Device," filed Jul. 16, 2013 or elsewhere in this specification, may also be utilized.

Figure 10:
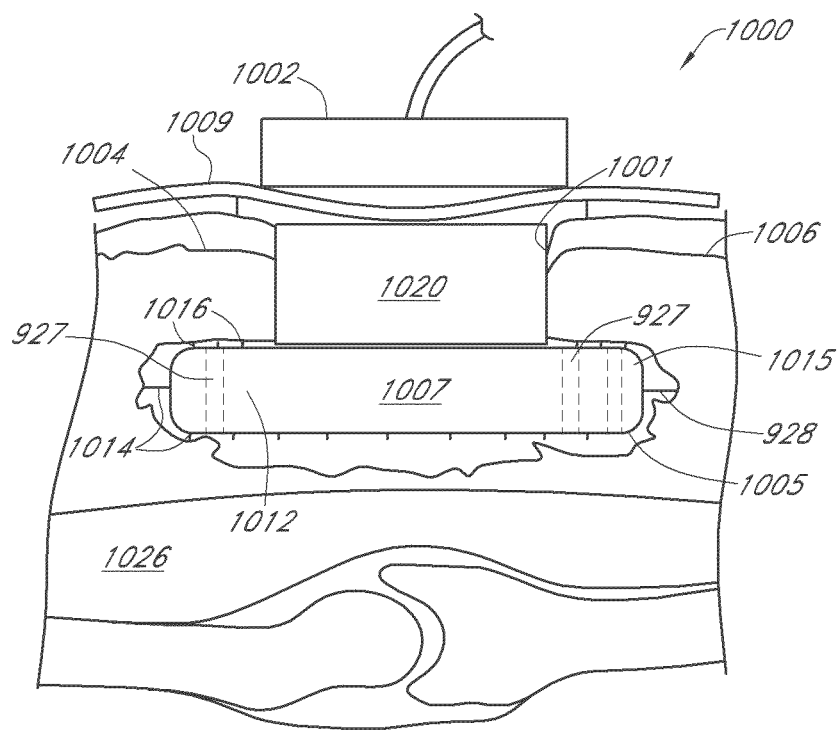
FIG. 10 illustrates a cross-sectional view of a wound drain and closure system used for a surgically treated pressure ulcer in accordance with a preferred embodiment of the invention.

FIG. 10 illustrates another embodiment where a wound closure element 1007 is positioned below a wound filler 1020, the wound closure element extending laterally beyond the wound filler 1020 such that the wound filler 1020 extends above or below the fascia. The wound closure element 1007 may be integral, attached to, or a separate element from the wound filler 1020. Furthermore, the features of the wound closure element may be incorporated into the lip 216 described above. The wound illustrated in FIG. 10 has a wound opening 1001 that can have a generally circular or oval shape. The surgeon can use this opening to access tissue that must be removed to form a cavity 1005 that extends laterally. The wound closure element 1007 extends laterally to regions 1012, 1015 which can include tissue anchors 1014, 1016 that serve to attach regions 1012, 1015 to tissue flaps 1004, 1006 above the regions 1012, 1015, respectively, as well as the underlying tissue 1026. The anchors 928 can also extend in a lateral direction. The wound filler 1020 is in fluid communication with wound closure element 1007, and enables the application of negative pressure to the channels of regions 1012, 1015 that can be employed in the embodiment of FIG. 10. The closure element can include apertures 927 that allow for tissue contact through regions 1012 and 1015 as these elements compress under negative pressure.

The tissue anchors or attachment mechanisms 1014, 1016 can be provided on the top surface 218 and the bottom surface 219 of the lip, respectively, to secure the wound securing material 200 to the tissue. The bottom surface 218 of the lip faces into the wound cavity and/or viscera, while the top surface 218 of the lip is opposite the bottom surface 219 and closest to the dermal layers. In some embodiments, the lip can extend under the fascia and be inserted between the fascia and the underlying peritoneal layer. The peritoneal layer is typically associated with abdominal fascia and lies below the abdominal fascia. When the lip is placed between the fascia and the peritoneal layer, the tissue anchors 1014 on the bottom surface 218 of the lip can extend into the peritoneal layer as the tissue anchors 1016 on the top surface 218 of the lip can extend into the fascia. In some embodiments, the lip can be placed below both the fascia and peritoneal layer. The tissue anchors 1016 on the top surface 218 of the lip can pass through the peritoneal layer into the fascia to grip the fascia and the peritoneal layer and secure the lip to the wound cavity. In some embodiments, the tissue anchors 1016 on the top surface 218 of the lip can attach to the peritoneal layer and secure the lip to the peritoneal layer. In some embodiments, the lip, elongate layer, and/or fingers can extend beneath the deep fascia, subserous fascia, serous membrane, peritoneum, or any other layer between the dermal layers and the viscera as described herein.

The attachment mechanisms (such as 701, 702 described above) can be provided over an entire outer perimeter surface of the wound securing material 200, or on surfaces of the lip 216, the wound fillers, the pad 925 or wound closure element 1007, or other surfaces as described above. For example, with respect to the embodiments of FIGS. 1-8J, when the filler material 103 is placed within a wound, the attachment mechanisms 701, 702 become buried within the tissue at the wound margins and secure the device 101 within the wound opening. The attachment mechanisms 701, 702 can be spread out over the entire surface of the wound margins to provide sufficient strength in the grasping force.

The wound securing material 200 can be designed to allow the wound closure device 101 to be easily placed but also easily removed and replaced with a new device 101 or other wound dressing as needed (e.g., 2-7 days later). The wound securing material 200 can be configured to have high grasping strength over at least a portion of its surface, but can be easily removed by, for example, pulling away at an edge. The wound securing material 200 can be designed to be removed from a wound without damaging the surrounding tissue. The attachment mechanisms 701, 702 can be designed to accommodate various tissue applications, such as muscle, fat, skin and collagen, and various combinations of these. The attachment mechanisms 701, 702 can also be designed to remain securely attached to particular tissues for a selected time period in certain embodiments. The attachment mechanisms 701, 702 can also be formed using a resorbable material.

Figure 11B:
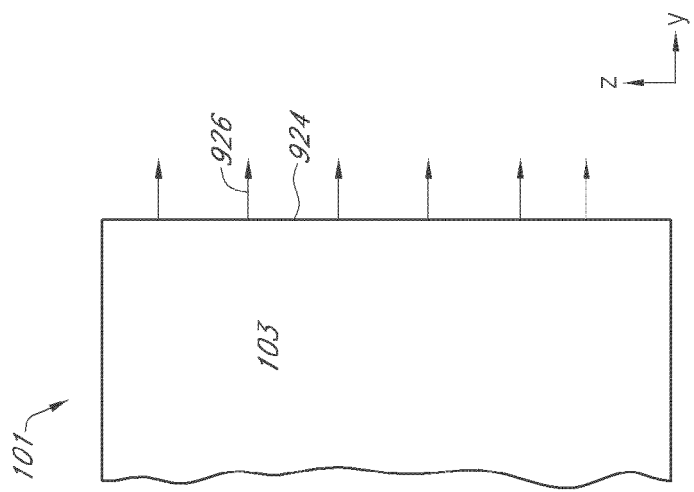
FIG. 11B is a cross sectional view of the tissue grasping surface of the wound closure device.
Figure 11A:
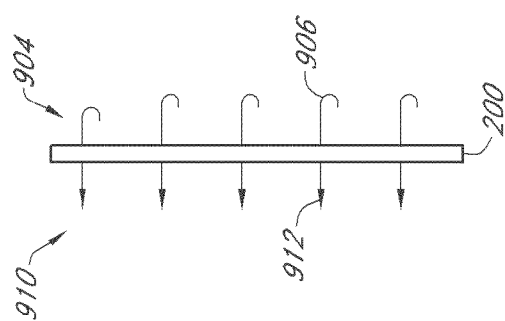
FIG. 11A illustrates an enlarged view of an embodiment of the tissue anchor system.

As shown in the cross-section view of FIG. 11A, for example, a wound securing material 200 may comprise an elongate member as described herein having two sets of attachment mechanisms. The wound securing material 200 can have a first set 910 of outwardly-facing tissue-grasping elements or attachment mechanisms 912 that are designed to project into tissue. These tissue-grasping elements are on a tissue grasping surface of the wound securing material 200. A second set 904 of elements 906 project into the filler material to secure the wound securing material 200 to the filler material. The second anchor elements or attachment mechanisms 904 can be shaped to grasp the filler material such as with a distal hooked shape 906. As material 200 must attach to the filler with a certain grasping strength in order to apply a sufficient pulling force on the tissue, a specified force level F, must be applied to remove the hooks from the filler material that exceeds the pulling force being applied to the tissue. Similarly, as the tissue to be grasped by the material 200 has different structural characteristics than the filler material, the first group of anchor elements 910 adapted to grasp tissue can have a different shape and grasping force than the second anchor elements. In this embodiment, barbs 912 can have bilateral prongs that tend to collapse upon insertion in tissue and yet expand when pulled in an opposite direction such that a certain pulling force can be applied to tissue. However, the prongs or cone shape anchor elements have a release force such that the barbs can be manually pulled from the tissue without causing injury.

FIG. 11B is an edge view of the device 101 showing the attachment mechanisms 926 projecting from the tissue grasping surface 924 on the periphery of the wound filler material 103. In some embodiments, the wound filler material 103 can be integrally formed with the wound securing material 200 including a tissue grasping surface 924 with anchor elements or attachment mechanisms 926. In other embodiments, the wound filler material does not contain a wound securing material 200 and the tissue grasping surface 924 with anchor elements or attachment mechanisms 926 is formed from the wound filler surface. The attachment mechanisms 926 can be provided over an entire outer perimeter surface of the filler material 103 spread out over the entire surface of the wound margins to provide sufficient strength in the grasping force. The tissue grasping surface and/or attachment mechanisms can also be formed using a resorbable material. The filler material 103 with the incorporated attachment mechanisms 926 can include all the features and descriptions of the attachment mechanism as described herein with reference to attachment mechanisms on the wound securing material 200.

Figure 11D:
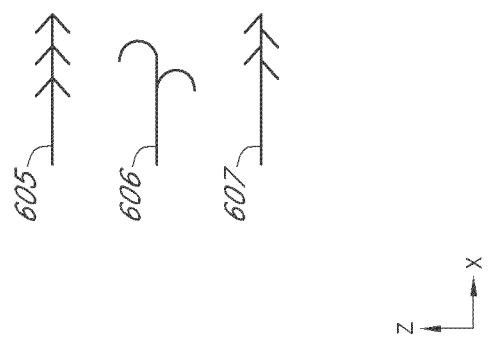
FIG. 11D illustrates different designs for a tissue anchor of the invention.
Figure 11C:
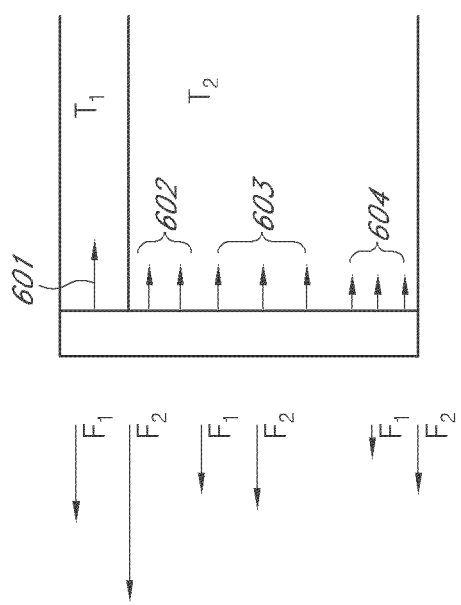
FIG. 11C is a side view of a tissue grasping surface, illustrating different tissue anchors for different types of tissue ($T_1$, $T_2$) and the respective force profiles for the anchors, including the maximum force applied during vacuum closure ($F_1$) and the force required to remove the anchors from the tissue ($F_2$) without damaging the tissue.

FIG. 11C is a side view of a tissue grasping surface of the wound securing material 200, illustrating different tissue anchors or attachment mechanisms 601, 602, 603, 604 for different types of tissue ($T_1$, $T_2$). Also illustrated is an example of the respective force profiles for the anchors or attachment mechanisms, including the maximum force applied to the tissue during vacuum closure ($F_1$) and the force required to remove the anchors from the tissue ($F_2$) without damaging the tissue. In one embodiment, the characteristics of the tissue anchors or attachment mechanisms vary to provide different force profiles across the interface between the wound closure device and the surrounding tissue. For example, for the upper tissue layer(s), $T_1$, the anchor 601 is designed to attach to collagen material, such as in the dermis. The anchor 601 has a different force profile ($F_1$ and $F_2$) on the upper tissue layer(s), $T_1$, as shown in FIG. 11C. At the lower tissue layers $T_2$, the anchors 602, 603, 604 are designed to attach to fatty tissue of subcutaneous layer. Generally, a smaller force profile is needed to secure the anchors to this tissue.

Figure 11E:
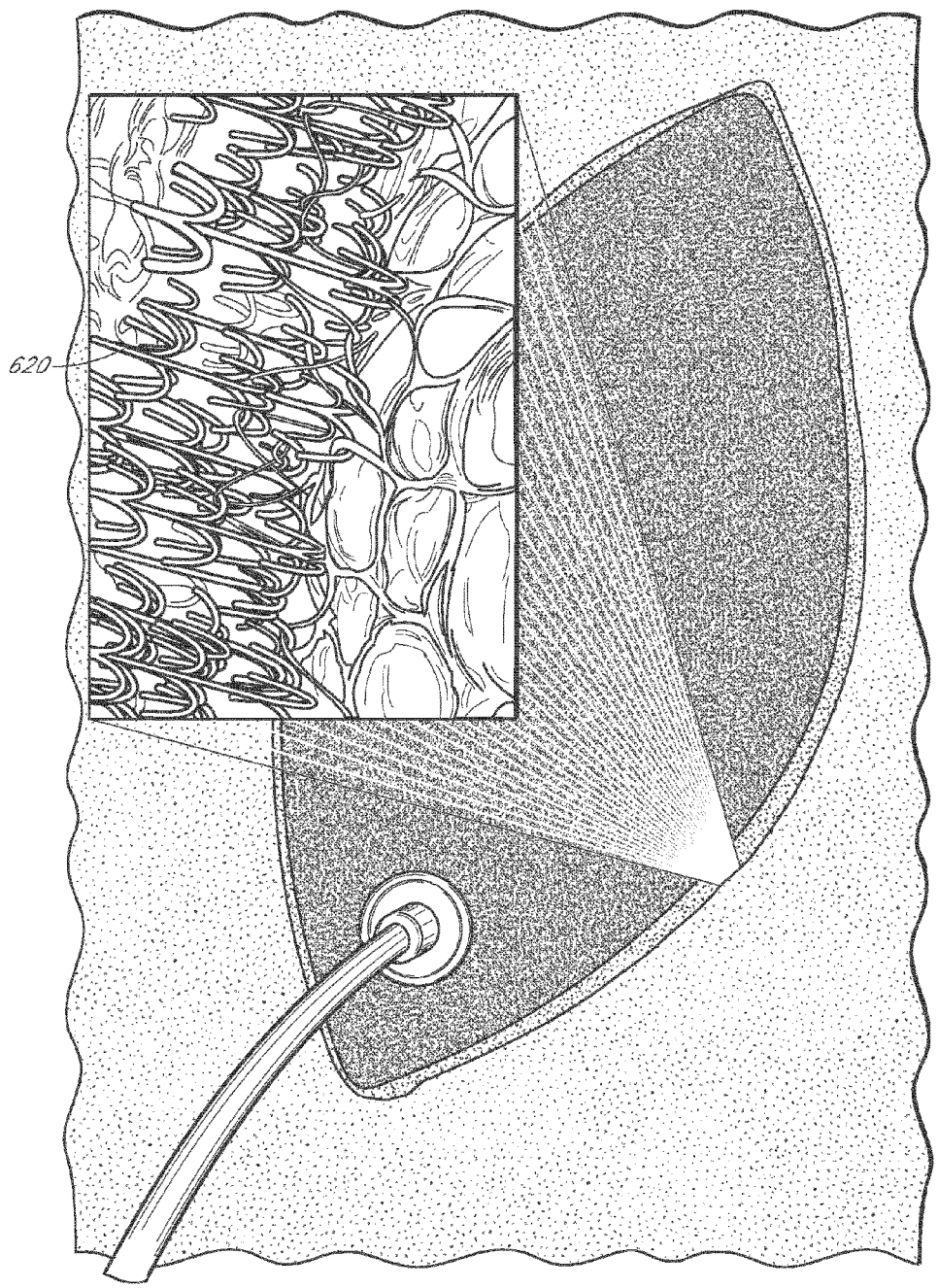
FIG. 11E illustrates an enlarged view of tissue anchor elements on the peripheral surface of an oval shaped wound closure device.

The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms. In FIG. 11C, for example, anchor 601 is significantly longer than anchors 602, 603, which in turn are longer than anchors 604. FIG. 11C also illustrates varying the density of anchors, such as shown in 602, 603 and 604. FIG. 11D illustrates three examples of different types of grasping features, including a barbed configuration 605, a staggered hook configuration 606, and a staggered barbed configuration 607. Other suitable grasping features can be utilized such as the anchor elements 620 shown in the enlarged perspective view of FIG. 11E. The anchoring or attachment process can be augmented by suturing the filler material or supporting endoskeleton to the tissue. The force profile can also be varied by controlling the vacuum force distribution in the filler material, such as by varying the pore size and/or pore density of the filler.

The wound closure device of the invention can be provided in kits for closing different types of wounds (e.g., abdominal, fasciotomy, etc.). The tissue grasping surface can be optimized for different types of tissue such as collagen, fatty tissue, and muscle, depending on the structure of the tissue at the wound site.

As the filler material contracts, the tissue grasping surface grabs and pulls on the adjacent tissue, which is preferably the tissue around the wound margins, resulting in the displacement of the tissue thereby facilitating the closure of the wound.

Figure 12B:
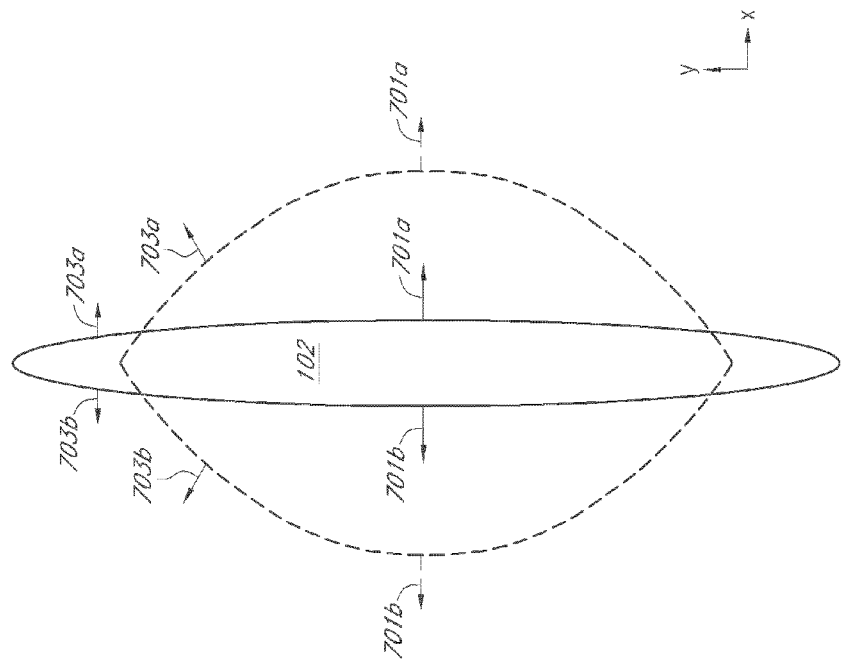
FIG. 12B illustrates the wound closure device of FIG. 12A after a period of wound closure and healing, with the original configuration of the wound and wound closure device indicated in phantom.
Figure 12A:
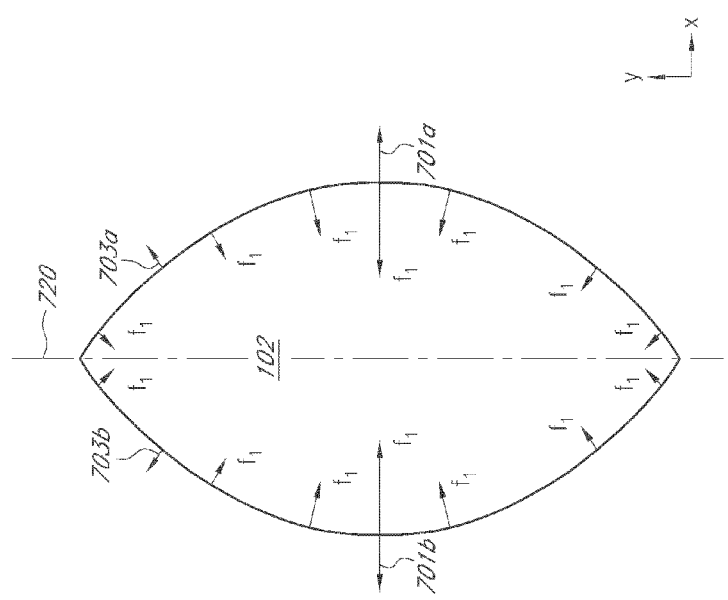
FIG. 12A is a schematic illustration of a wound closure device positioned within a wound showing the different force profile around the margin of the wound according to one embodiment.

In certain embodiments, the force profile of the wound closure device is variable around the periphery of the wound. An exemplary embodiment is illustrated in FIG. 12A, which shows the force profile ($f_1$) exerted on the wound margins at a plurality of locations on the periphery of the wound. In this embodiment, the largest $f_1$ is at the central region of the wound filler 102, where the wound opening is widest and the wound closure force is entirely or nearly entirely in the x-direction. Moving towards the top and bottom regions of the wound, the closure force ($f_1$) is much smaller. One reason for this is because the wound opening is much smaller in these regions, and a much smaller force is needed to reapproximate the tissue. Also, the inward force exerted in these regions includes components in both the x- and y-directions. Thus, a smaller force profile can be used to avoid the inward collapse of the tissue in the y-direction. As illustrated in FIG. 12B, as the wound closes and heals from an initial state (indicated by dotted lines) to a later state (indicated by solid lines), it can become elongated in the y-direction. Thus, the displacement of tissue anchors or attachment mechanisms 701a and 701b is exclusively in the x-direction and in the direction of the closure force ($f_1$), while the displacement of tissue anchors or attachment mechanisms 703a, 703b is both inwards in the x-direction (in the direction of the closure force) and outwards in the y-direction (opposite the direction of the closure force). Thus, a smaller $f_1$ is preferable in these regions to provide more "play" between the attachment mechanisms and the surrounding tissue. In other embodiments, the wound closure device can be configured so that it does not elongate, but rather does not change its length along the long axis 720.

The variation in the force profile around the periphery of the wound closure device can be achieved in a variety of ways, such as varying the spacing/density of the tissue attachment mechanisms, the types of attachment mechanisms, length of attachment mechanisms, or configuration thereof, etc. For example, in FIGS. 10A and 10B, attachment mechanisms or anchors 701a, 701b are longer and penetrate deeper into the tissue compared to attachment mechanisms or anchors 703a, 703b. The force profile can also be varied by controlling the vacuum force distribution in the filler material, such as by varying the pore size and/or pore density of the filler.

FIG. 13A, a wound closure device 101 is placed within the wound opening so that the tissue grasping surface 1104 with attachment mechanisms 1106 are contacting the wound margin 203.

FIG. 13B illustrates the wound 1200 following the application of a negative pressure to the wound closure device 101. The tissue anchor elements 1106 grab the tissue margins 203 and cause displacement of the tissue margins 203 as the filler material 1102 collapses. As seen in the FIG. 13B, the filler material 1102 collapses in the x- and y-directions in such a manner as to reapproximate the tissue at the wound margin 203. In some embodiments, as illustrated in FIGS. 13A and 13B, stabilizer elements 1108 can be included in the wound filler material 1102 in a crosshatched configuration of the help control the direction of tissue displacement during collapse. The largest amount of tissue displacement in this embodiment is in the central region of the wound 1200, where the opening is widest, and this displacement is primarily inward along the x-direction. Away from the central region (e.g., at the top and bottom of the wound as shown in FIGS. 13A and 13B), where the wound margins are closer together, less displacement in the x-direction is needed to reapproximate the tissue.

In one embodiment, the internal stabilizer elements 1108 promote the collapse of the filler material in a manner that provides wound reapproximation. In an embodiment as illustrated in FIG. 13B, for example, during filler collapse the crosshatched stabilizer elements 1108 straighten out relative to one another, similar to an accordion gate. The largest displacement is in the central region of the filler 1102, along the x-direction. The stabilizers 1108 can inhibit inward collapse along the y-direction. As the stabilizers 1108 straighten out, they can also facilitate elongation of the wound in the y-direction to allow proper tissue reapproximation.

In some embodiments, the inward collapse of the filler material along the y-direction is undesirable. For example, during tissue reapproximately, the wound 1200 will tend to elongate in y-direction as the wound margins close in the x-direction.

In some embodiments, the wound filler can include a peripheral stabilizer element on the wound filler. The peripheral stabilizer element can be configured to expand and contract as necessary with the expansion and contraction of the wound filler material. Thus, in an embodiment, the stabilizer element has sufficient flexibility to contract and expand in the x- and y-directions (i.e., along the periphery of the filler material 103), but has adequate rigidity along the z-direction (i.e. along the height of the filler) to inhibit collapse or tilting in this direction. The tissue grasping anchor elements or attachment mechanisms can be included on the peripheral stabilizer element, and project out from the periphery of the filler material. This can be as an alternative to, or in addition to, providing the anchor elements or attachment mechanisms on a separate wound securing material 200.

In any of the embodiments described herein, the wound securing material can be formed of a material that is sufficiently stiff to hold the wound securing material and the wound filler that the wound securing material surrounds in place when placed in the wound. In some embodiments, the wound filler and the surrounding wound securing material do not contain attachment mechanisms. For example, the wound securing material can be formed of a sufficiently stiff that allows the wound securing material to be secured under the fascia or other tissue without the need for attachment mechanisms.

In any of the embodiments described herein, the edges of the wound securing material may be rounded edges to avoid tissue trauma when inserted within the wound site. For example, the elongate layer and lip described above may have edges that are not sharp, but instead are rounded. The wound securing material with rounded edges can contact and act on the surrounding tissue in contact with the material similar to embodiments described herein without rounded edges. In some embodiments, the wound securing material with rounded edges can assist in the closure of the wound as effectively as wound closure devices with material that contains edges that are not rounded.

Further Embodiments of Wound Treatment Devices and Methods

FIGS. 14-25G illustrate further embodiments of wound treatment devices and methods that may incorporate any of the apparatuses and methods hereinbefore described. For example, the wound securing materials described above may be applied to the wound fillers, wound packers, and/or stabilizing structures described above to assist in positioning such devices in a wound. In some of the embodiments described below, where the wound closure devices are surrounded by a porous layer such as foam and/or an anchoring layer, such layers may be replaced with or incorporate features of the wound securing materials described above.

Figure 14:
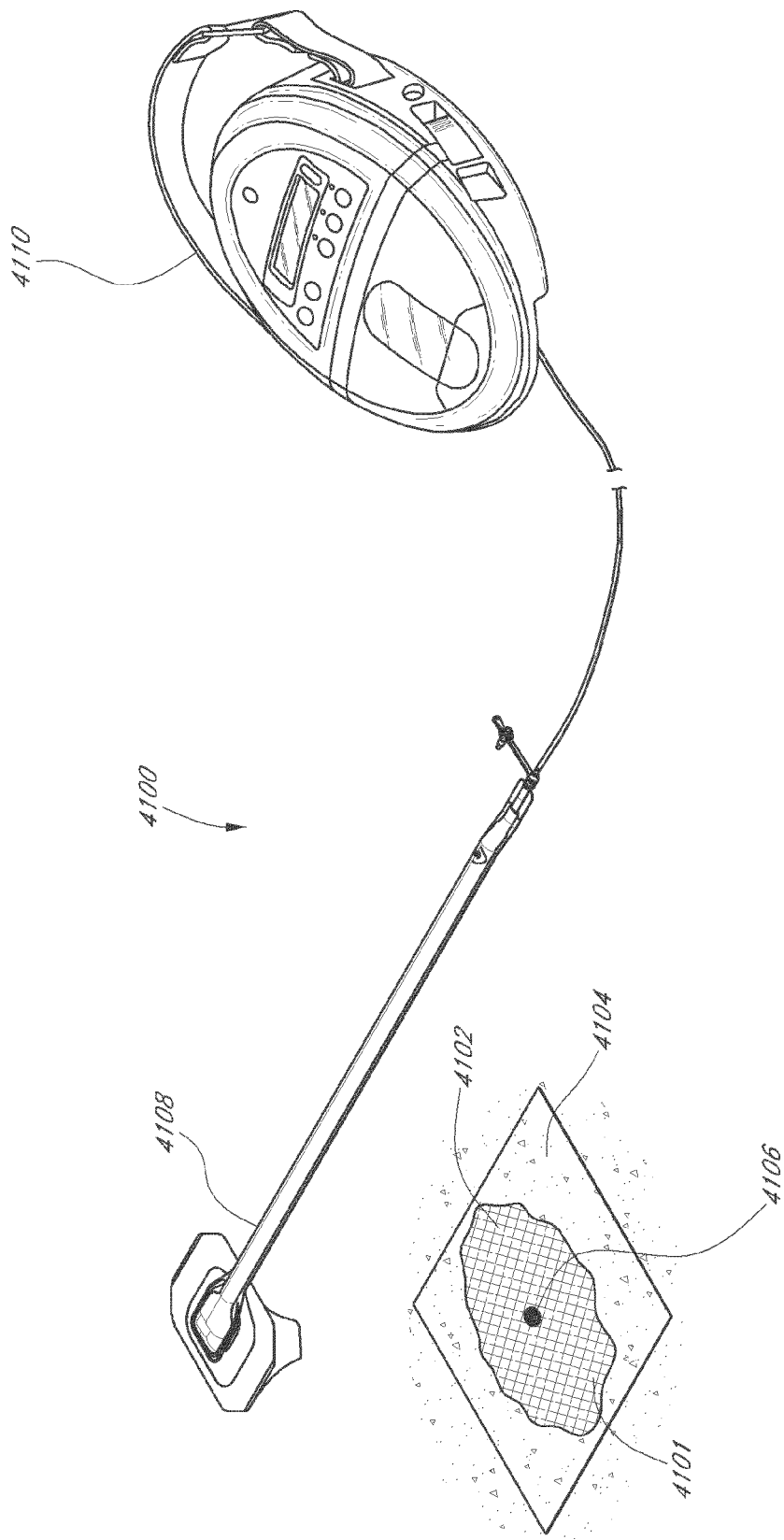
FIG. 14 illustrates an embodiment of a negative pressure treatment system.

FIG. 14 illustrates an embodiment of a negative pressure treatment system 4100 that comprises a wound packer 4102 inserted into a wound 4101. The wound packer 4102 may comprise porous materials such as foam, and in some embodiments may comprise one or more embodiments of wound closure devices described in further detail in this section or elsewhere in this specification. In some embodiments, the perimeter or top of any wound closure device inserted into the wound 4101 may also be covered with foam or other porous materials. A single drape 4104 or multiple drapes may be placed over the wound 4101, and is preferably adhered or sealed to the skin on the periphery of the wound 4101 so as to create a fluid-tight seal. An aperture 4106 may be made through the drape 4104 which can be manually made or preformed into the drape 4104 so as to provide a fluidic connection from the wound 4101 to a source of negative pressure such as a pump 4110. Preferably, the fluidic connection between the aperture 4106 and the pump 4110 is made via a conduit 4108. In some embodiments, the conduit 4108 may comprise a RENASYS® Soft Port™, manufactured by Smith & Nephew. Of course, in some embodiments, the drape 4104 may not necessarily comprise an aperture 4106, and the fluidic connection to the pump 4110 may be made by placing the conduit 4108 below the drape. In some wounds, particularly larger wounds, multiple conduits 4108 may be used, fluidically connected via one or more apertures 4106.

In some embodiments, the drape 4104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 4101 is prepared and cleaned. In some cases, such as abdominal wounds, a non- or minimally-adherent organ protection layer (not illustrated) may be applied over any exposed viscera. The wound packer 4102 is then inserted into the wound, and is covered with the drape 4104 so as to form a fluid-tight seal. A first end of the conduit 4108 is then placed in fluidic communication with the wound, for example via the aperture 4106. The second end of the conduit 4108 is connected to the pump 4110. The pump 4110 may then be activated so as to supply negative pressure to the wound 4101 and evacuate wound exudate from the wound 4101. As will be described in additional detail below and in relation to the embodiments of the foregoing wound closure devices, negative pressure may also aid in promoting closure of the wound 4101, for example by approximating opposing wound margins.

With respect to certain wound fillers and stabilizing structures as described herein, it will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times or 10 times greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

Stabilizing Structures and Wound Closure Devices of FIGS. 15A-18D

FIGS. 15A-F illustrate embodiments of a stabilizing structure 4200. The stabilizing structure may comprise a plurality of elongate strips 4202 arranged in parallel, whose longitudinal length can be aligned with the longitudinal axis when placed in a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can be placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue.

In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate.

In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 15A:
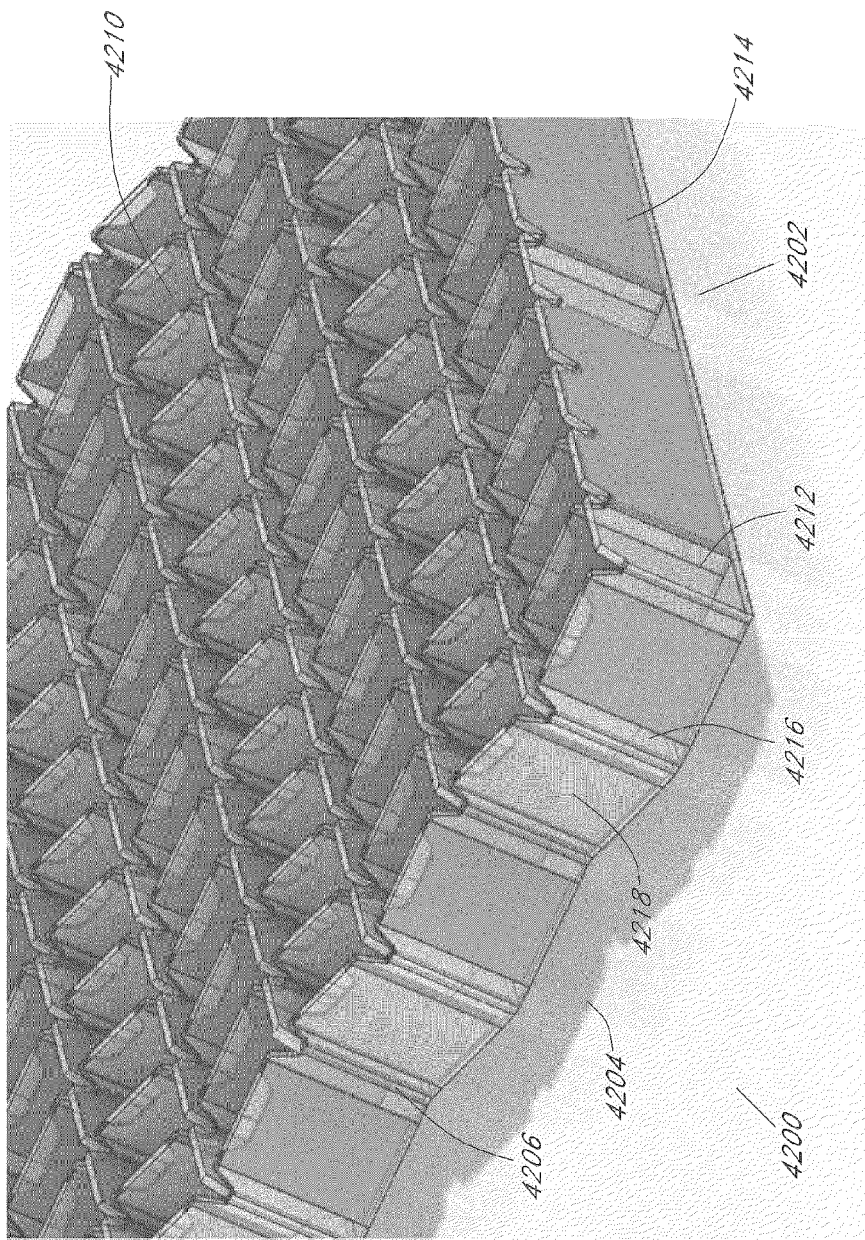
Figure 15B:
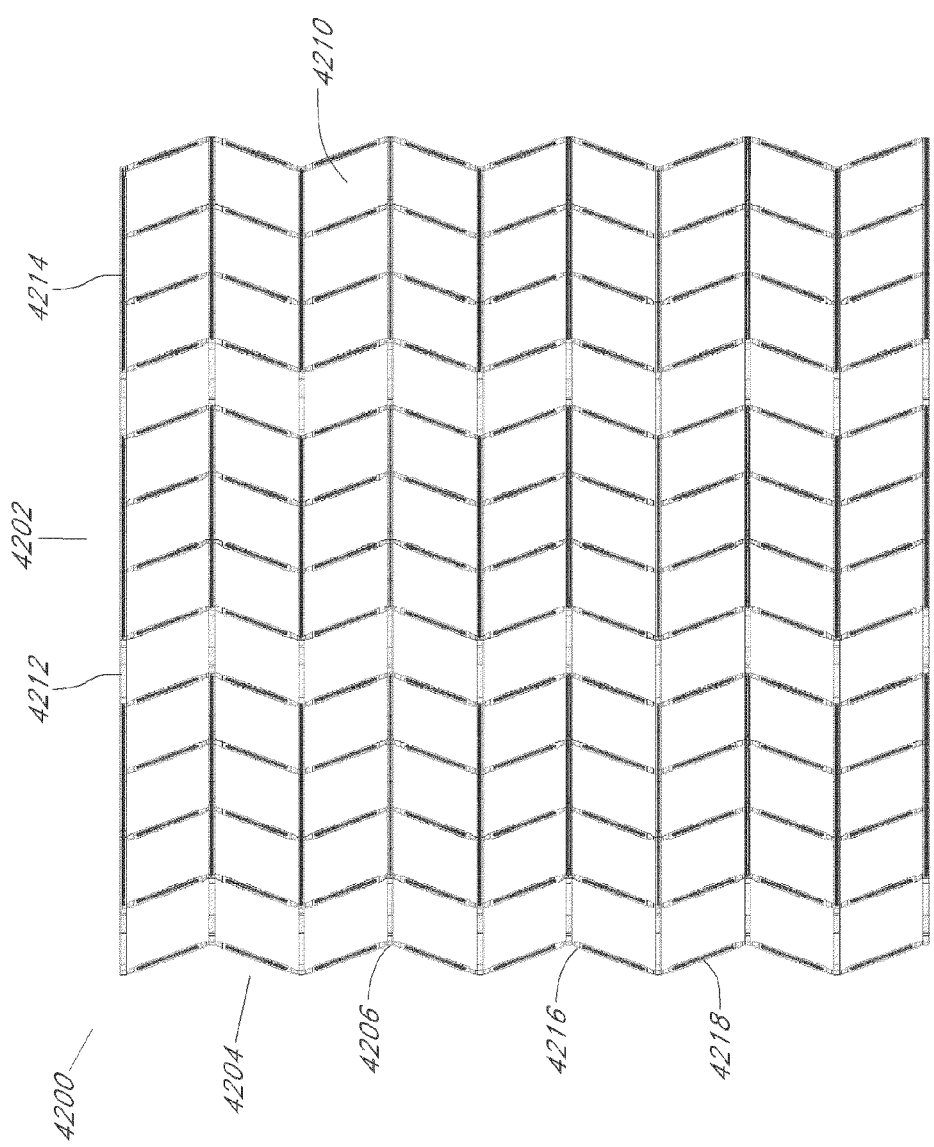

As illustrated in the perspective view of FIG. 15A and the top view of FIG. 15B, the intersection of the intervening members 4204 and the elongate strips 4202 may define a plurality of cells 4210. In certain embodiments, the cells 4210 may be of any of the shapes and sizes described in this section or elsewhere in this specification. For instance, a cell may be in the shape of a square, a diamond, an oblong, an oval, and/or a parallelepiped.

The joints 4206 are configured to allow the intervening members 4204 to collapse. The joints 4206 can be configured to allow the intervening members to collapse in any manner as described in this section or elsewhere in this specification in relation to other embodiments. For example, the joints 4206 may be configured to allow or preferentially cause a first row of intervening members 4204 to collapse in one direction, while allowing or preferentially causing an adjacent row to collapse in another direction.

The elongate strips 4202 may comprise alternating flexing segments 4212 and supporting segments 4214. In a preferred embodiment, the flexing segments 4212 may be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 15A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material).

The elongate strips 4202 may be manufactured from a female mold that may further encompass the entire stabilizing structure 4200. The supporting segments 4214 can be inserted into the female mold, followed by an injection of a flexible polymer such as silicone and/or polyurethane to encase the supporting segments 4214 within the flexible polymer frame. The supporting segments 4214 can be inserted into the mold in any desired manner or quantity, allowing for many potential variations of the stabilizing device.

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure 4200. In such embodiments, the elongate strips 4202 may form pockets that are open from one side (e.g., from the top) to allow insertion and removal of the supporting segments 4214.

Figure 15D:
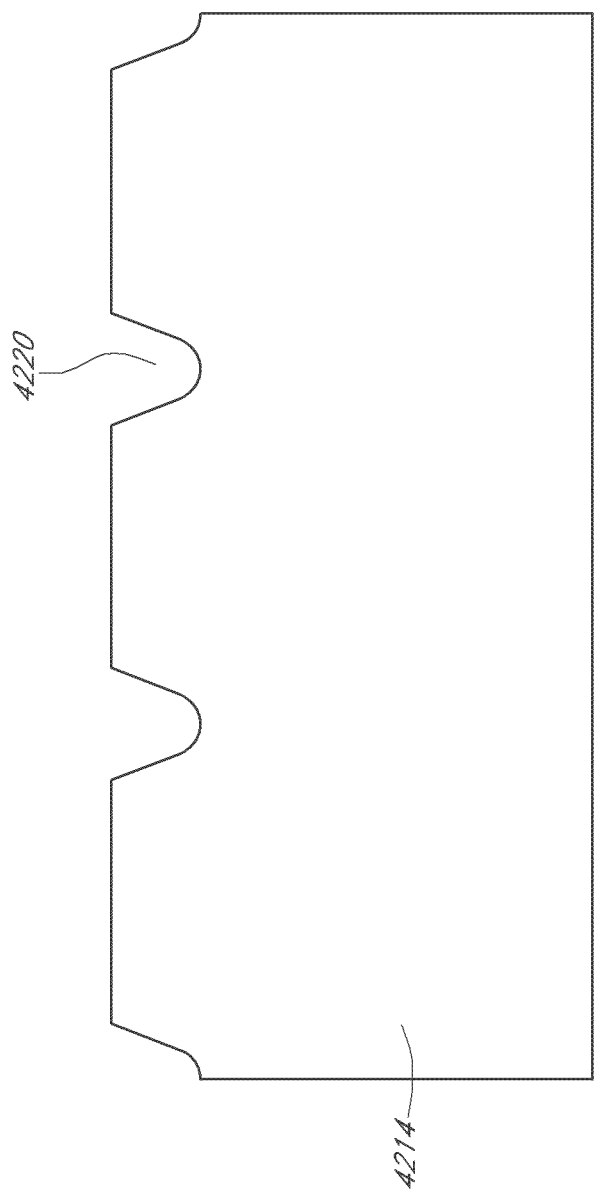

FIGS. 15C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch, or the notches could be located semi-randomly on the top and bottom of the stabilizing structure. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 15C-D or any other similar shape.

Figure 15E:
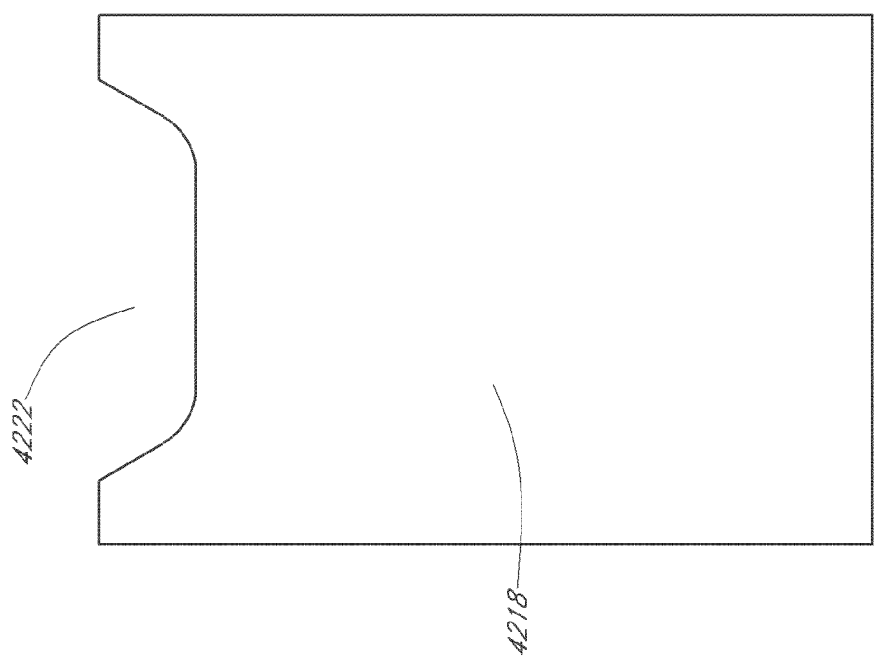
Figure 15F:
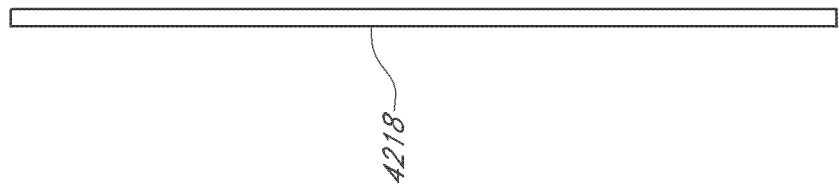

The intervening members 4204 in some embodiments may comprise a first material 4216 with an embedded insert 4218 made of a more rigid material. One embodiment of the embedded insert is illustrated in FIGS. 15E-F. In certain embodiments, the insert 4218 is placed within a female mold and a flexible polymer such as silicone and/or polyurethane is injected around the insert to entomb the insert 4218 within a flexible polymer frame. The inserts 4218 can be inserted into the mold in any desired manner or quantity, allowing for many potential variations of the stabilizing device. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 15E illustrates a front view of insert 4218, while FIG. 15F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 15A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 15C-D, the sections may be detached along perforations or lines in the elongate strips corresponding to the notches 4220.

In some embodiments, the inserts 4218 may be entombed within first material 4216 in a variable number of intervening members 4204 to control the shape and collapse of the stabilizing structure 4200. In other embodiments, the inserts 4218 may be inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the stabilizing structure in a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 15A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

Figure 15G:
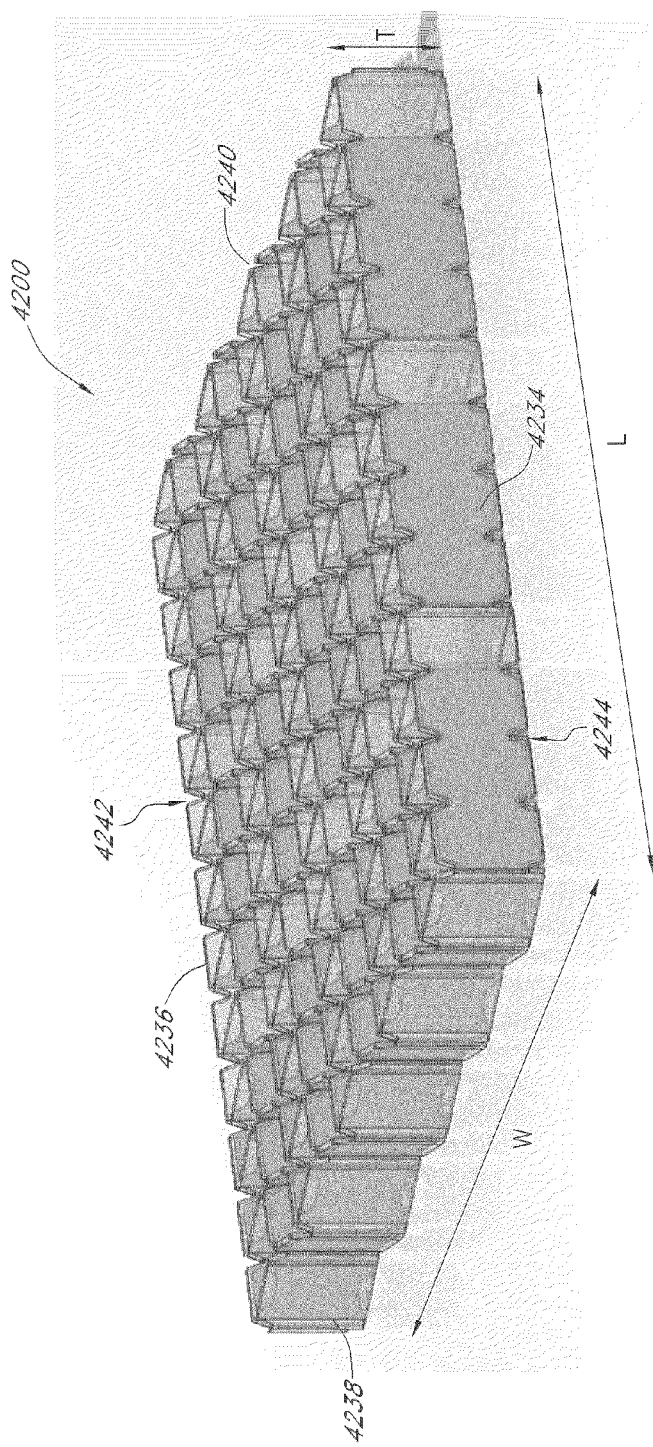
FIGS. 15G-15I illustrate multiple views of another embodiment of a stabilizing structure.
Figure 15H:
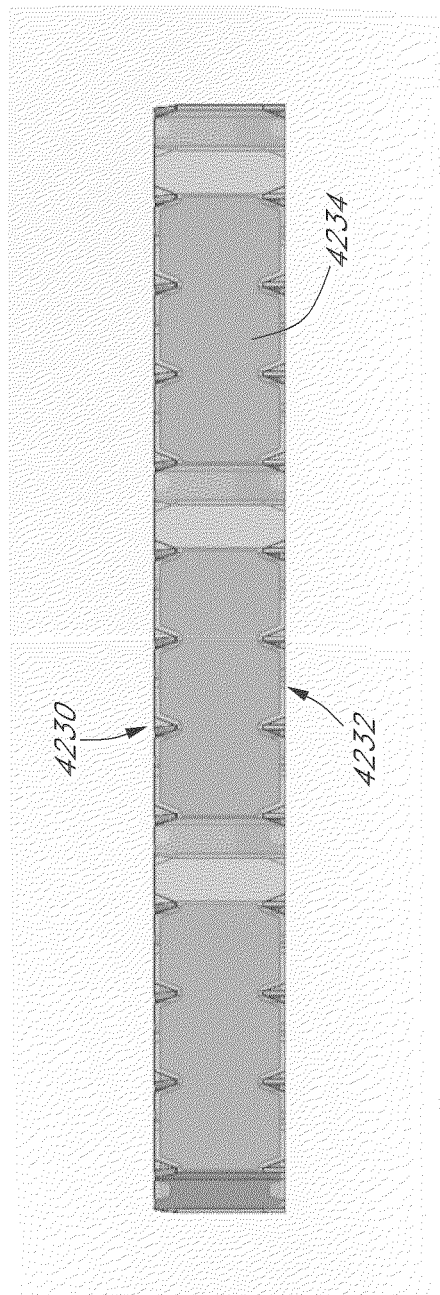
Figure 15I:
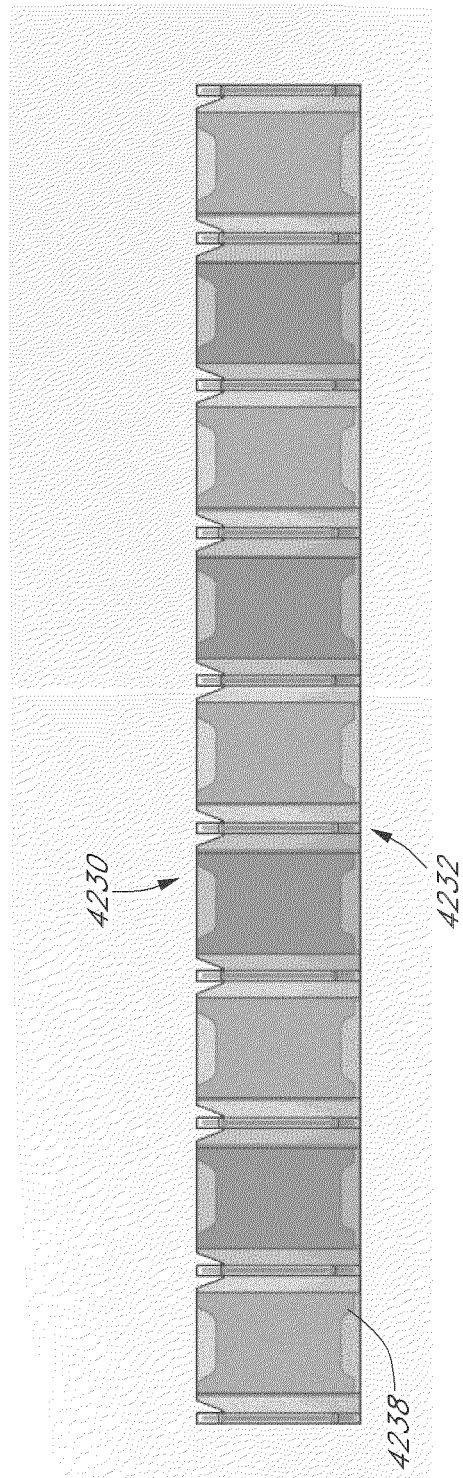

FIGS. 15G-15I illustrate another embodiment of a stabilizing structure 4200 similar to the stabilizing structure described above with respect to FIGS. 15A-15F. In this and other embodiments, the stabilizing structure may have a length L and a width W that extend parallel to a horizontal plane, and a thickness T that may extend vertically and perpendicular to the horizontal plane. As illustrated, the length L and the width W may be greater than the thickness T so that the stabilizing structure forms a generally planar or flat body having an upper surface 4230 and a lower surface 4232 that may be parallel to each other. The thickness T of the structure may be constant between the upper and lower surfaces, or it may vary. The stabilizing structure of FIGS. 15G-15I may further comprise notches 4242 and 4244 in both the upper surface 4230 and lower surface 4232, respectively. These notches may extend through the elongate strips 4202 as well as through supporting segments 4214.

The stabilizing structure of FIG. 15G may define an outer perimeter that is general rectangular in shape, though other shapes are contemplated. In one embodiment, the stabilizing structure has a first side 4234 and a second side 4236 opposite the first side. FIG. 15H illustrates a side view of first side 4234. These sides 4234 and 4236 may be straight in shape and be parallel to each other. These sides also need not be parallel, and can have other shapes such as curved. The stabilizing structure may also have a third side 4238 and a fourth side 4240 opposite the third side. FIG. 15I illustrates a side view of third side 4238. The third and fourth sides may have a zig-zag shape as shown, but may also have other shapes such as straight and curved.

Applicable to all stabilizing structures or wound closure devices described in this section or elsewhere in the specification, a soft polymer could be molded over the entire stabilizing structure 4200 to soften the feel of the device, thereby protecting the surrounding organs and/or other tissues. In other embodiments, the soft polymer could be molded only over the bottom portion of the stabilizing device 4200, while in some embodiments the softer polymer can be molded over the top and/or the sides of the device. In some embodiments, the soft polymer could be molded over particular edges of the stabilizing structure 4200, such as those on the bottom, sides, and/or top. In certain embodiments, the soft polymer could be molded over any side or combination of sides of the stabilizing structure 4200. The soft polymer may act like a softened rim surrounding the hard edges of the stabilizing structure 4200.

Figure 16:
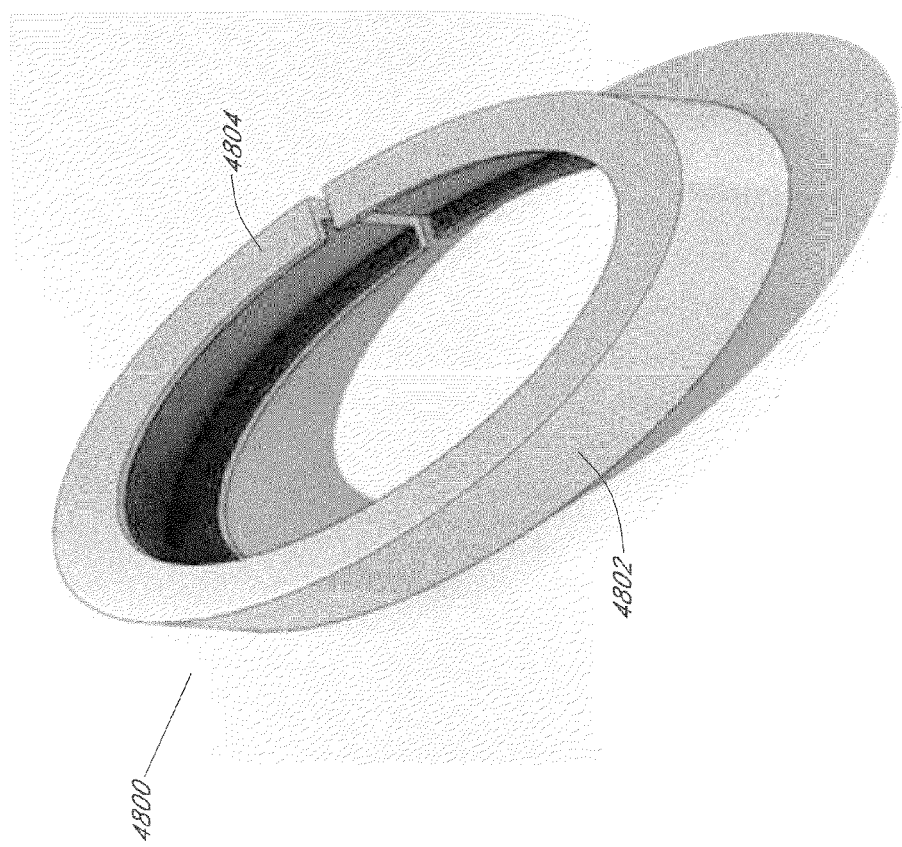
FIG. 16 illustrates an embodiment of a ring that can surround a stabilizing structure.

FIG. 16 illustrates an embodiment of an anchoring layer 4800 that may surround the stabilizing structures as described in this section or elsewhere in this specification. The ring 4800 can comprise a layer of tissue anchors 4802 configured to grip the surrounding edges of a wound. For example, the tissue anchors can be hooks, barbs, prongs, or other structures that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

Figure 17:
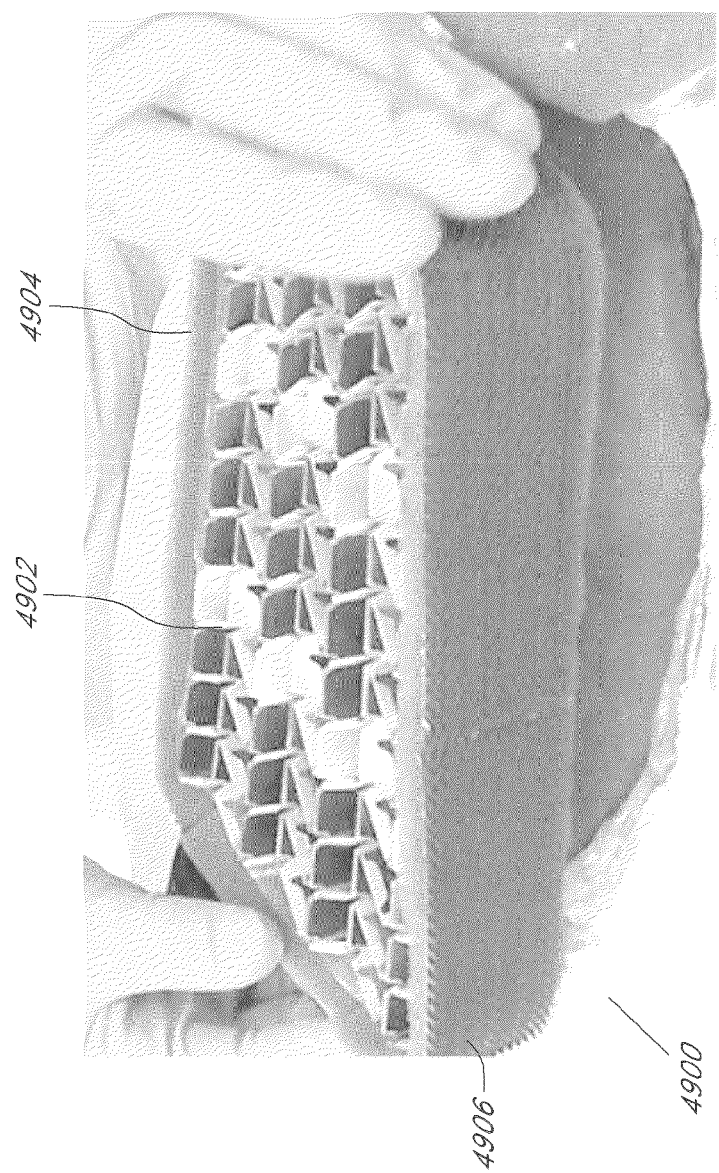
FIG. 17 illustrates an embodiment of a stabilizing structure with surrounding anchoring and foam layers.

FIG. 17 is a photograph of a wound closure device 4900 comprising a stabilizing structure 4902 such as those described in this section or elsewhere in this specification, a foam layer 4904 such as those described in this section or elsewhere in this specification, and an anchoring layer 4906 comprising tissue anchors similar to the ring depicted in FIG. 16. In some embodiments, the wound closure device 4900 may be placed in a wound and sealed with a drape. Similar to the embodiments illustrated in FIGS. 15A-F, the stabilizing structure 4902 can collapse in any manner described in this section or elsewhere in this specification.

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 18A-D are photographs of a wound closure device 5000 according to another embodiment. The wound closure device 5000 comprises a stabilizing structure 5002 which may be similar to the structures described in FIGS. 15A-I, or may comprise any of the stabilizing structures described elsewhere in this specification. The stabilizing structure 5002 is surrounded by a porous layer 5004 such as a layer of foam, and the porous layer is surrounded by an anchoring layer 5006 comprising tissue anchors such as those anchors produced by Velcro industries, various barbs and/or various hooks. In some embodiments, the tissue anchors are similar to the rings depicted in FIGS. 16-17. In certain embodiments, the porous layer may be in the form of a ribbon. The stabilizing structure 5002, porous layer 5004 and anchoring layer 5006 may be provided as separate components to be attached by the practitioner in use, or they may be pre-attached to each other.

Similar to the embodiments illustrated in FIGS. 15A-I, the stabilizing structure 5002 can collapse in any manner described elsewhere in this specification, for example, horizontally. When the wound closure device 5000 is implanted, the surrounding tissues can be pressed against the tissue anchors to embed them within the tissue and anchor the device. In some embodiments, the wound closure device 5000 may be placed in a wound and sealed with a drape. Although the embodiments further described in this section comprise an anchor layer that surrounds a porous layer, other embodiments may omit the porous layer, such that the anchoring layer directly surrounds or is attached to the stabilizing structure.

In some embodiments, the anchoring layer 5006 comprises an elongate strip of material comprising a plurality of tissue anchors extending from a base layer 5007, wherein the tissue anchors can have different shapes and sizes as described elsewhere in the specification. The tissue anchors may extend from a first planar side of the elongate strip, and the second planar side of the elongate strip may comprise an adhesive covered by an adhesive backing layer. The structure of the anchors can have various forms depending on the tissue they are intended to bind. Longer anchors can be used for loosely bound tissues such as fat or connective tissue, while shorter anchors can be used for denser tissues such as muscle. In other embodiments, depending upon the shape of the anchor, shorter anchors may be more desirable for softer, fatty tissue, while longer anchors are utilized for denser tissues. Anchors with more rigid stems can be utilized to penetrate denser tissues. In some embodiments, anchors can have bilateral prongs that tend to collapse upon insertion in tissue and yet expand when pulled in an opposite direction such that a certain pulling force can be applied to tissue. The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms.

The anchors may have various lengths for optimal penetration of the surrounding tissue. For example, the length of the anchors may be at most about 0.01 mm, at most about 0.1 mm, at most about 0.2 mm, at most about 0.5 mm, at most about 1 mm, at most about 2 mm, at most about 3 mm, at most about 5 mm, at most about 10 mm, at most about 20 mm, at most about 30 mm, at most about 40 mm, at most about 50 mm, at most about 75 mm, at most about 100 mm, or more than 100 mm.

Figure 18A:
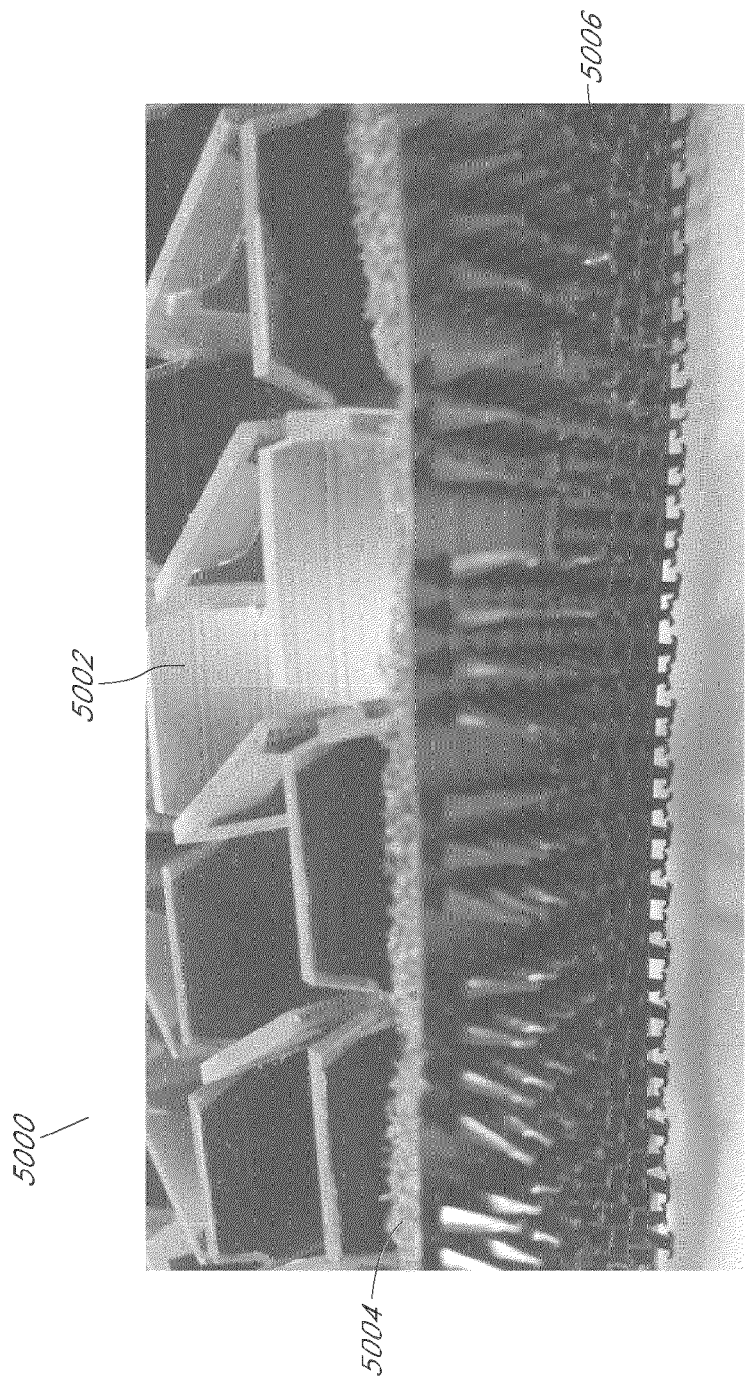
FIGS. 18A-D illustrate another embodiment of a stabilizing structure with surrounding anchoring and foam layers.
Figure 18B:
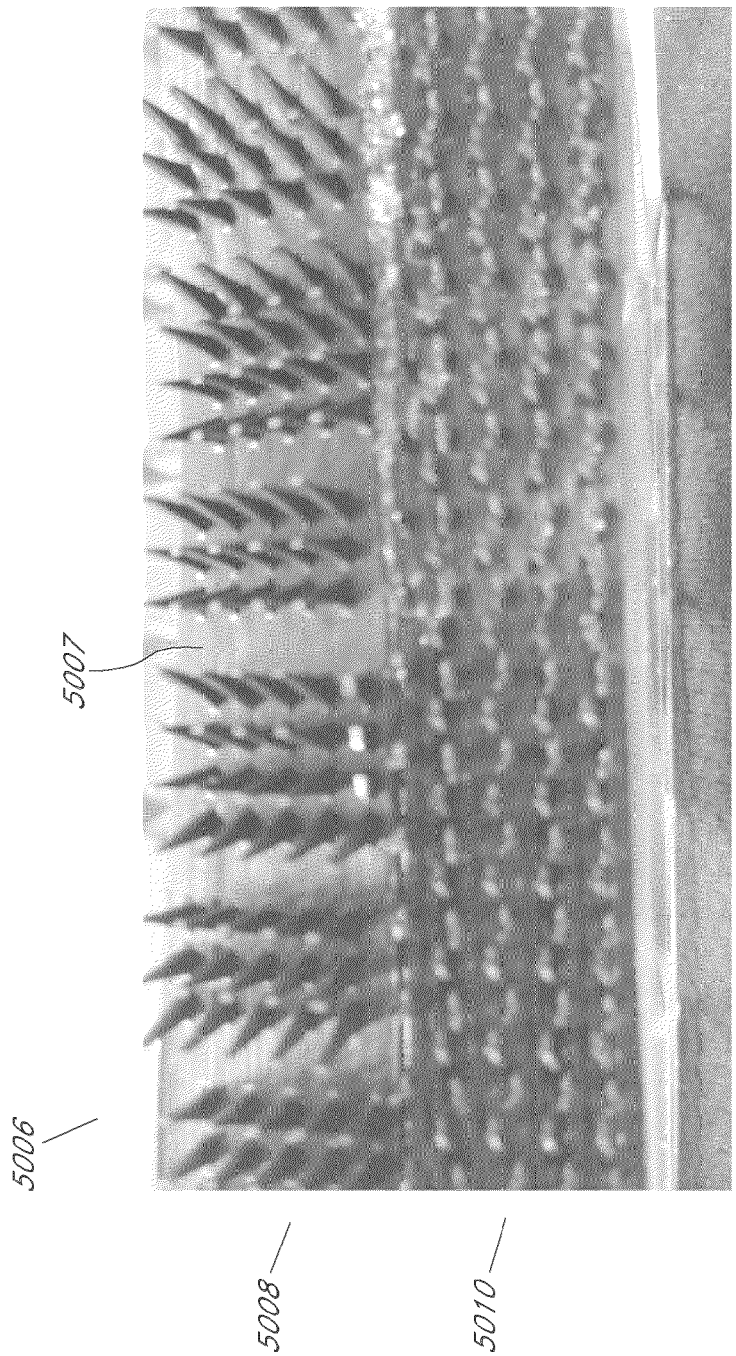

FIG. 18B is a photograph of a closer view of the anchoring layer 5006 of the wound closure device 5002 depicted in FIG. 18A. The anchoring layer may consist of a first band of longer anchors 5008 configured to surround the porous layer 5004 and stabilizing structure 5002, and a second band of shorter anchors 5010 configured to surround the porous layer 5004 and stabilizing structure 5002. As illustrated, the first band 5008 may be disposed above the second band 5010. In some embodiments, there may be additional alternating series of bands vertically relative to each other. In further embodiments, the different bands may have different anchor lengths and shapes, as disclosed herein this section and elsewhere in the specification. For example, instead of 2 types of bands with 2 types of anchors, there may be 3 types of band with 3 types of anchors or 4 types of bands with 4 types of anchors and so on. Preferably, the anchors are selected for the appropriate tissue types. For example, returning to FIG. 18B, the first band 5008 may comprise longer anchors, desirable for penetration into the denser fascia, and thus may be positioned towards the bottom of the device. Similarly, the second band 5010 comprises shorter double hooks, desirable for penetration into denser tissue. Other suitable tissue anchors, as described elsewhere in this specification, include the hook and loop configuration of Velcro, barbs, hooks, spikes, pegs, arrowheads, or any suitable shape. Further examples of surfaces include textured surfaces, such as roughened sandpaper-like surfaces, or nano-textured surfaces that may facilitate tissue adhesion.

In some embodiments, the use of surface anchors can be used in combination with a surgical adhesive, providing a much stronger bond between tissue layers than the adhesive alone, and providing temporary adhesion while the adhesive sets. In some embodiments, the surgical adhesive can be added to the anchors themselves. In certain embodiments, the surgical adhesive may simply be applied between the anchors to coat at least a portion of the anchoring layer. In further embodiments, the anchors may be replaced with a surgical adhesive, and the surgical adhesive may act to anchor the device to the surrounding wound.

In certain embodiments, the anchors may be constructed from a variety of materials, including any materials disclosed elsewhere in the specification, such as: synthetic or natural polymers, metals, ceramics, or other suitable materials. The anchors may be constructed from biodegradable materials such as biodegradable synthetic or natural polymers. Non-limiting examples of biodegradable synthetic polymers include: polyesters such as polylactic acid or polyglycolic acid, polyanhydrides, and linear polymers with biodegradable linkages. Further, the anchors may be constructed of biodegradable biological materials, such as autografts, allografts, and/or xenografts.

Figure 18C:
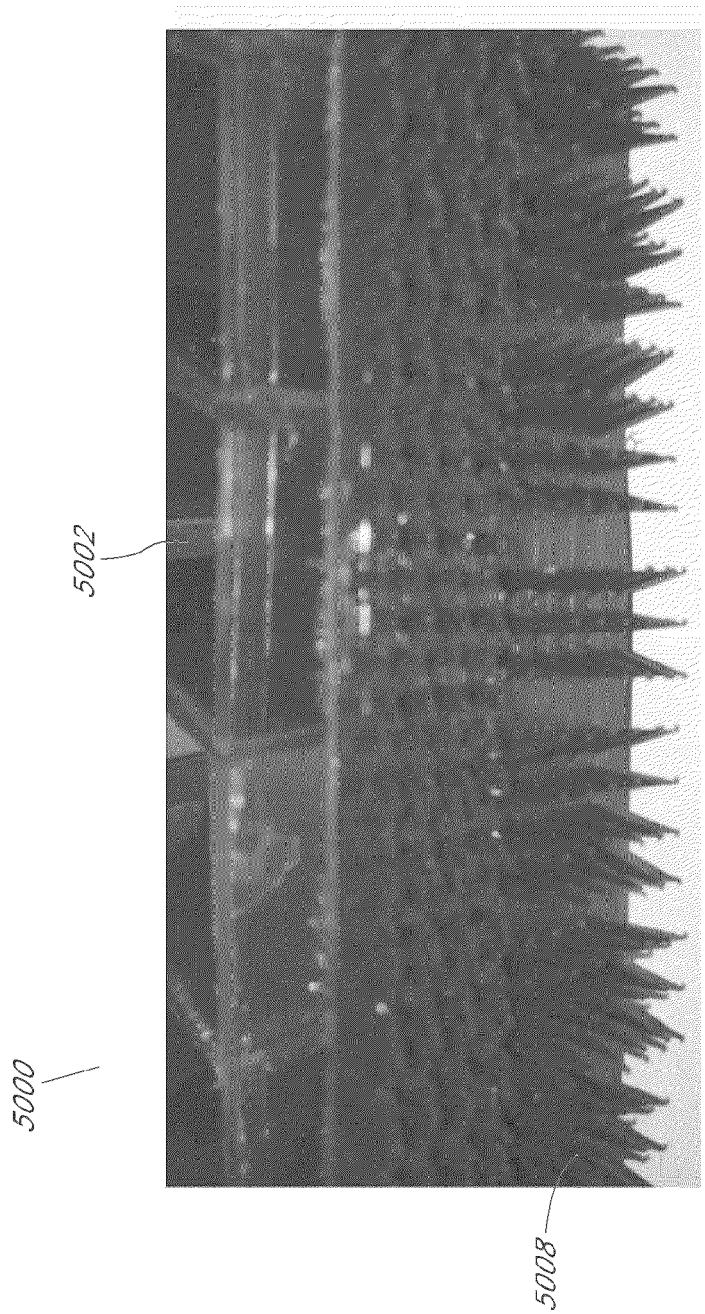
Figure 18D:
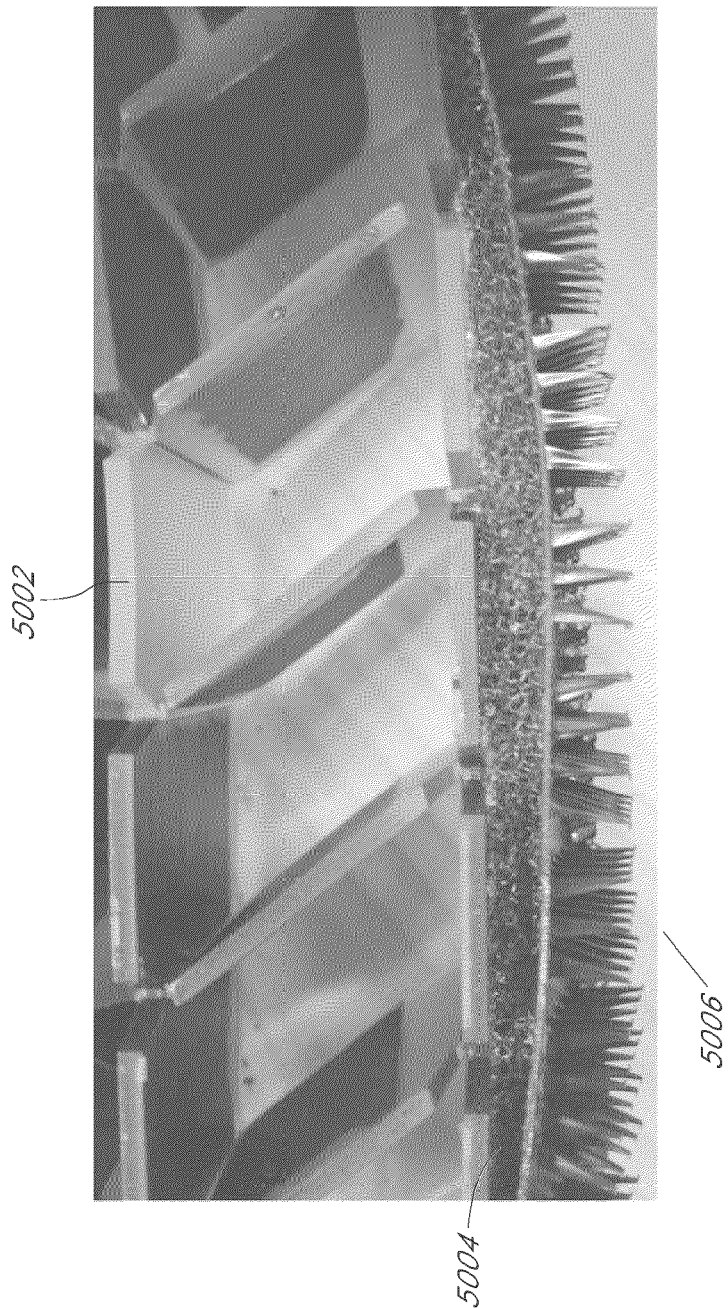

FIG. 18C is a photograph of an embodiment of a wound closure device 5000, similar to the wound closure devices of FIGS. 18A-B. However, in this orientation the first band 5008 of anchors is towards the bottom of the device, while the second band of anchors 5010 is towards the top. As described above, the bands of anchors may be arrayed in any desired manner. FIG. 18D is a top view of an embodiment of a wound closure device 5000, similar to the wound closure devices of FIGS. 18A-C.

Considering the anchoring layer of FIGS. 18A-D, the shape of the anchoring layer is not limited to the ring shape of FIGS. 17-18D. In some embodiments, the anchoring layer is wrapped around the entirety of the stabilizing device, i.e. the top, bottom, and sides. In other embodiments, the anchoring layer is only around a portion of the perimeter of the stabilizing structure. In certain embodiments, the anchoring layer is only attached to discrete portions of the stabilizing structure as needed. In some embodiments, the anchoring layer covers at most about 5%, at most about 10%, at most about 20%, at most about 30%, at most about 50%, at most about 75%, and at most about 100% of the outside of the stabilizing structure.

In some embodiments, the bands of different tissue anchors can be organized in a vertical direction, while in other embodiments, they may be organized in a horizontal direction. They may also be organized in either the horizontal and vertical directions when considered in the xy plane, i.e. facing downward into the wound.

In certain embodiments, the different types of anchors may be interspersed with one another, rather than organized into discrete bands of specific types of anchors. For example, the longer anchors may be surrounded by smaller anchors and vice-versa. In some embodiments, the anchors may be organized randomly across the anchoring layer or in other suitable patterns.

In particular embodiments, the anchoring layer may be disposed on the inner faces of the stabilizing structure. For example, the anchoring layer may cover at most about 5%, at most about 10%, at most about 20%, at most about 30%, at most about 50%, at most about 75%, and at most about 100% of the interior surfaces of the stabilizing structure.

In further embodiments, the entire anchoring layer may be comprised of only one type of anchor, for example the entirety of the anchoring layer may be comprised of the longer hooks 5008 or the shorter hooks 5010 as depicted in FIG. 18B. Some embodiments may call for the anchors to be color coded. For example, the anchors on the bottom may be made to be one color while the anchors on the top may be another so as to identify the proper orientation of the stabilizing structure in the wound.

Wound Closure and Treatment Methods of FIGS. 19-25G

FIGS. 19-23D are photographs and illustrations depicting embodiments of a method for the treatment of a wound that utilizes a wound closure device comprising a stabilizing structure as described herein this section and elsewhere in the specification. To better illustrate a non-limiting embodiment of the method, numbers have been added to each step in FIGS. 23A-D to allow the reader to more easily follow these steps of the method. However, the steps can be performed in any order, and any numbering system is for clarity only. Further, in some embodiments, different steps of this method may be excluded. In other embodiments, additional steps may be added to the method based on methods described herein this section and elsewhere in the specification. The porous layers and structures described in this section may be of any material or structure described elsewhere in the specification, such as foam.

Figure 19:
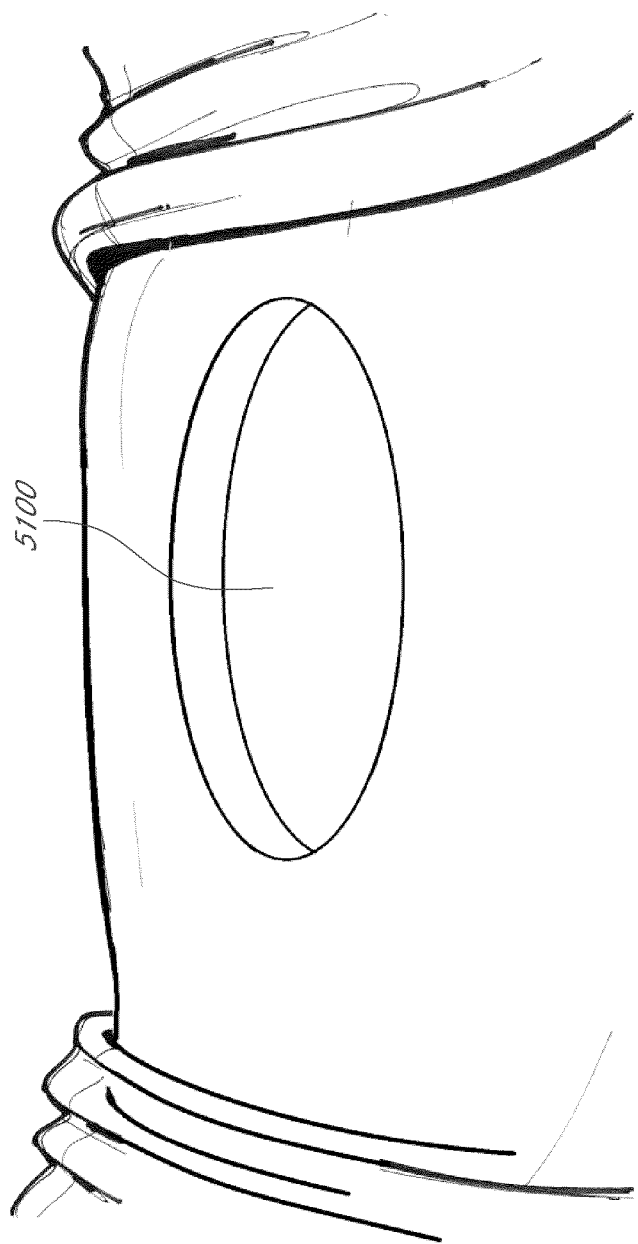
FIG. 19 illustrates an embodiment of an open abdominal wound.

FIG. 19 depicts an embodiment of an open wound 5100 prior to treatment with a wound closure device as will be described in much greater detail below. The open wound of FIG. 19 is similar to the wounds described elsewhere in the specification, particularly as relates to FIG. 14. In some instances, as described elsewhere in the specification, such a wound may be produced via a surgical incision or other means.

Figure 20:
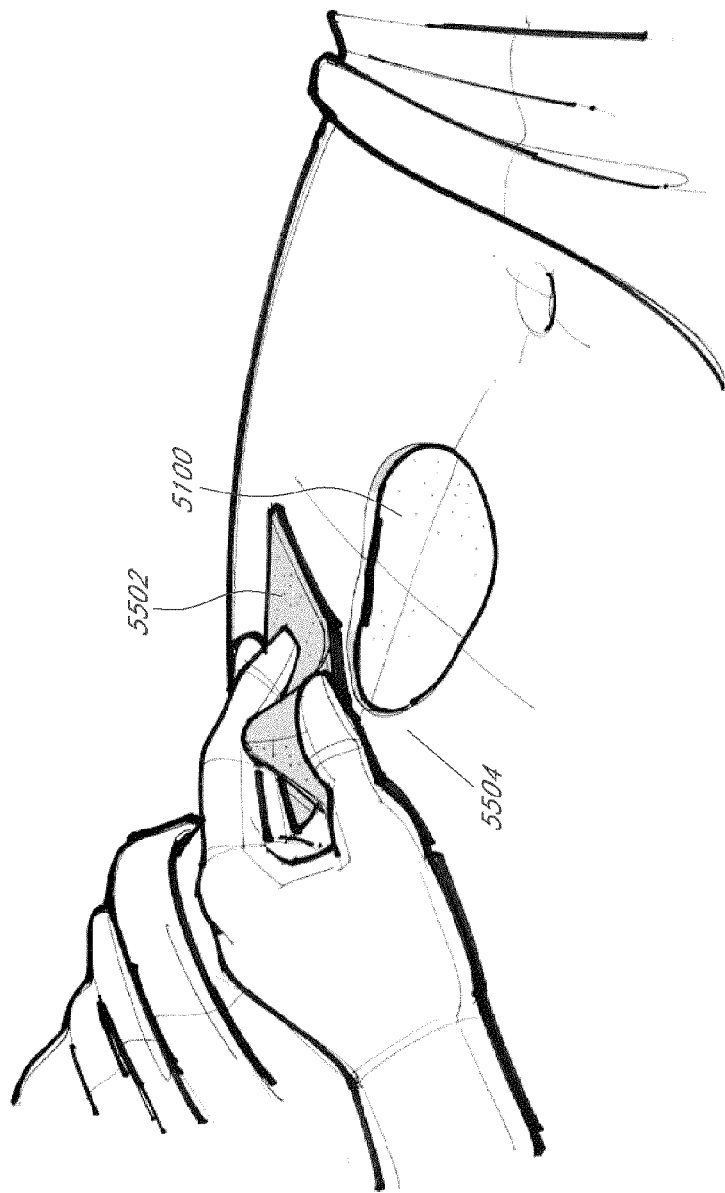
FIG. 20 illustrates an embodiment of a step in a method of treating a wound.

FIG. 20 depicts an embodiment of an initial step in a method for the treatment of an open wound 5100 with a wound closure device. Before treatment, the wound may be cleaned with a pad 5502 and the skin 5504 prepared for application of a wound closure device, such as those described in relation to FIGS. 15A-18D and FIGS. 23A-23C.

Figure 21:
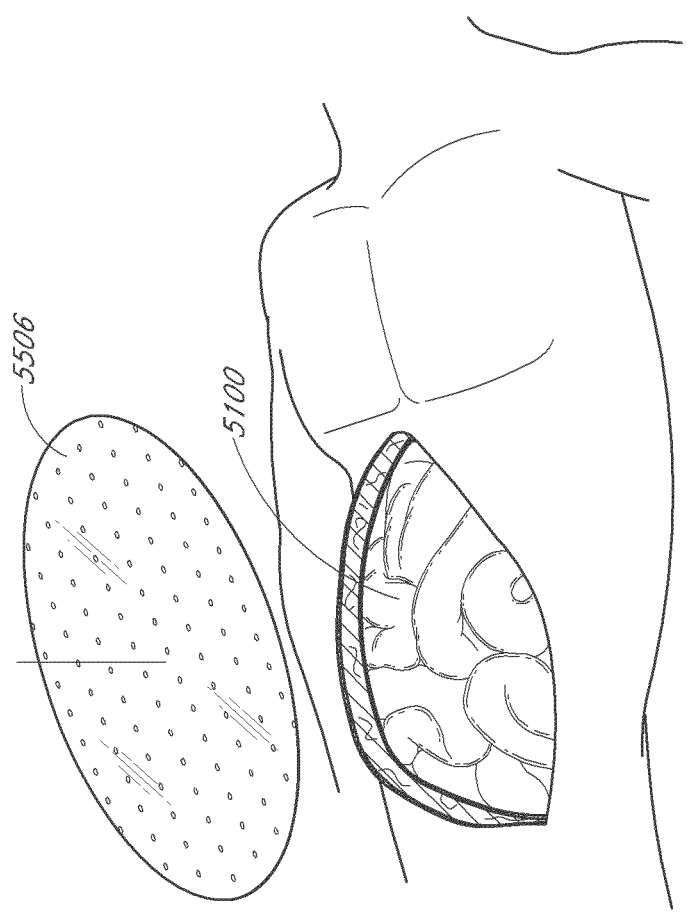
FIG. 21 illustrates an embodiment of a step in a method of treating a wound.

FIG. 21 depicts an embodiment of an early step in a method for the treatment of an open wound 5100. In some embodiments, a tissue protection layer 5506 may be placed over the wound to protect the underlying tissues from the rigors of negative pressure wound therapy or other potential harms. Accordingly, certain embodiments provide for a tissue protection layer 5506 which may be cut to size to be placed over the wound site 5100. The tissue protection layer 5506 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 5100 and tucked over the peritoneal gutter. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer 5506 can be provided with openings, such as holes, slits, or channels, to allow the removal of fluids from the wound site 5100 or the transmittal of negative pressure to the wound site 5100. In further embodiments, the tissue protection layer may be used over non-abdominal wounds on other areas of the body, such as the leg, arm, shoulder, or back.

Figure 22A:
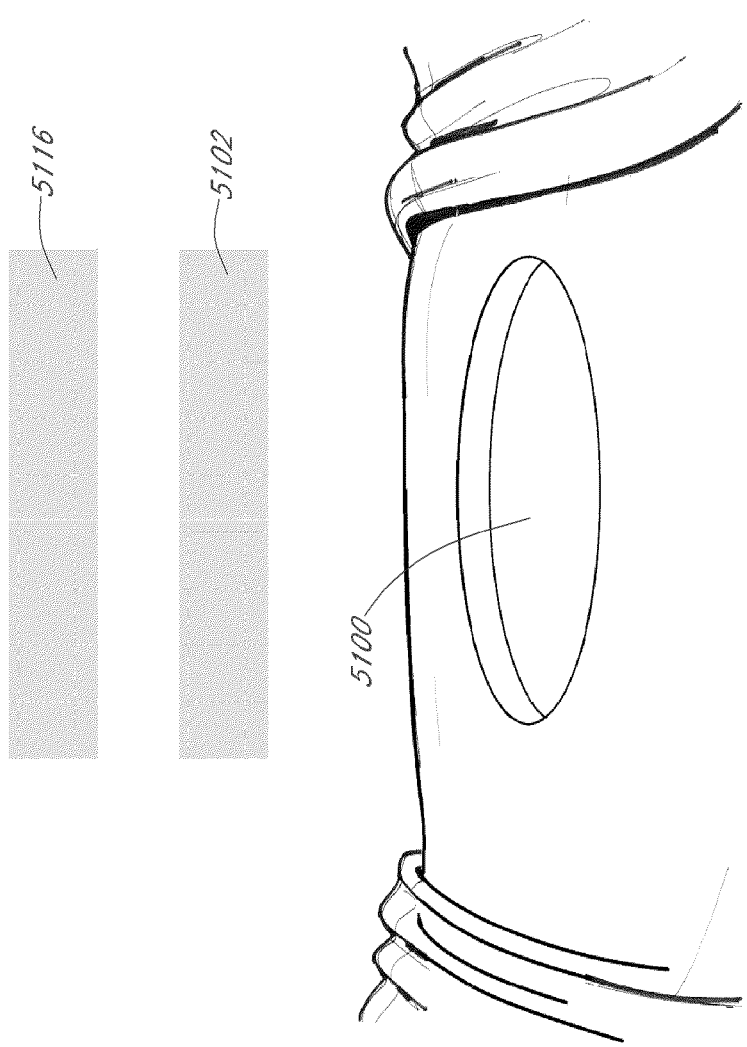
FIGS. 22A-C illustrate an embodiment of steps of a method of treating a wound.
Figure 22B:
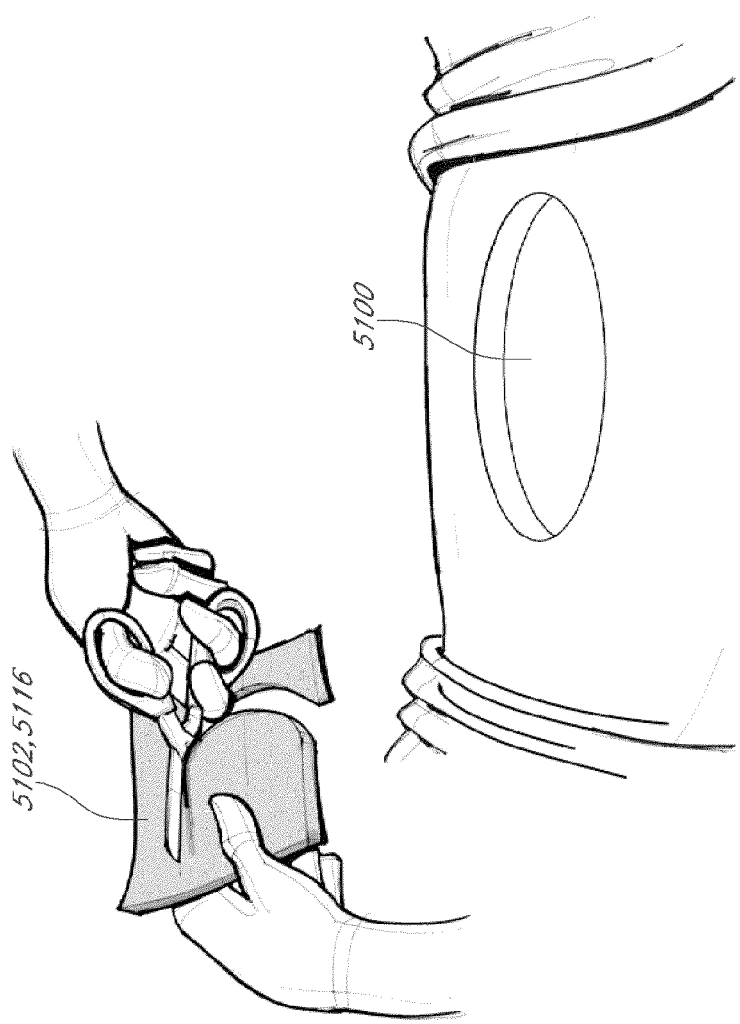
Figure 22C:
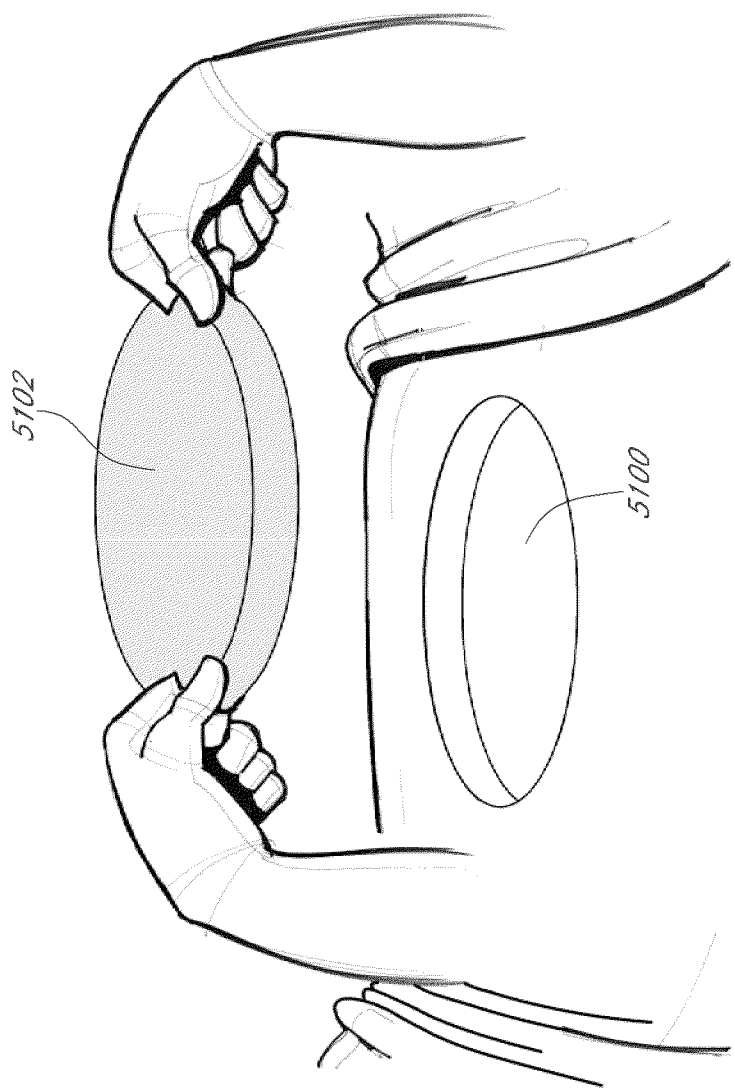

FIGS. 22A-C illustrate embodiments of possible initial steps in a method for the treatment of an open wound. However, as described above, the steps need not be performed in this order and may be performed in any order. In FIG. 22A, two pieces of a porous material such as foam, a bottom piece 5102 and a top piece 5116 are selected so as to approximate the size of the wound 5100. In some embodiments, the top piece and the bottom piece are of identical thickness. However, in certain embodiments, and vice-versa, top piece 5116 may be at least twice as thick, at least four times as thick, at least 10 times as thick or more than ten times as thick as bottom piece 5102. FIG. 22B illustrates an embodiment of additional steps in a method for the treatment of an open wound. Bottom piece 5102 may be shaped via cutting or other suitable means to the shape of the wound and subsequently placed into the wound 5100, as shown in FIG. 22C and depicted further below in FIG. 23A.

Figure 23A:
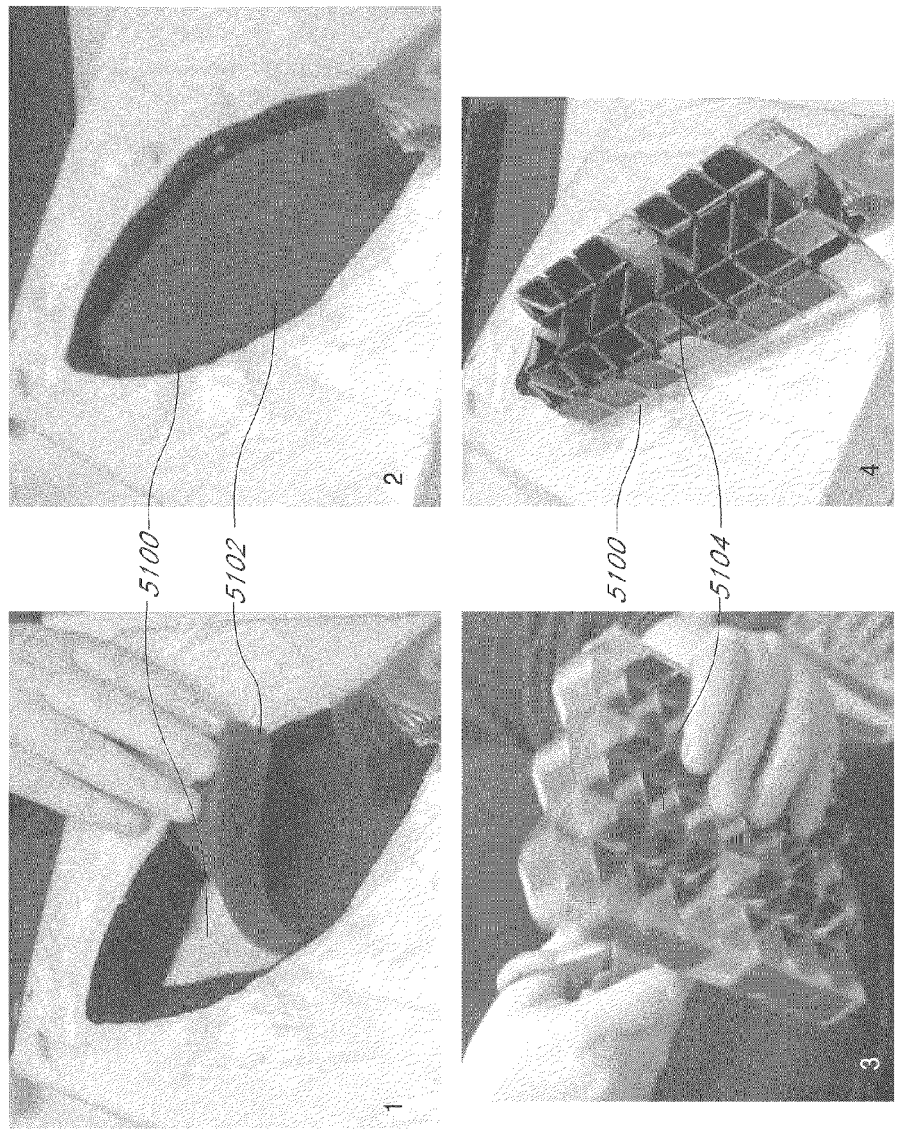
FIGS. 23A-C illustrate an embodiment of steps of a method of treating a wound.

Beginning with steps 1 and 2 of FIG. 23A, after shaping, a foam layer 5102 (for example, a 15 mm layer of foam) is placed in the wound bed 5100. In steps 3-4, a stabilizing structure 5104 similar to the stabilizing structures disclosed in FIGS. 15A-I or any other stabilizing structure described elsewhere in the specification, is shaped to the size of the wound via cutting or other suitable means. In certain embodiments, the matrix may be shaped in such a manner as to ensure that the matrix has flat, longitudinal sides. As displayed in step 4, the stabilizing structure 5104 may be placed in the wound to determine the accuracy of the shaping step. Preferably, when using a stabilizing structure of FIGS. 15A-I, the stabilizing structure is placed such that grooves or notches as described elsewhere in the specification are facing downward. However, in some embodiments, grooves or notches may be present on both the top and the bottom of the stabilizing structure. In steps 5-6 of FIG. 23B, a foam layer 5106, in the shape of a ribbon, is attached to the outer edge of the stabilizing structure 5104 via an adhesive backing tape or other suitable means. The foam layer 5106 may be used to partially or completely surround the perimeter of the stabilizing structure 5104. Excess ribbon can simply be removed from the backing tape and discarded. To allow the backing layer to properly adhere to the stabilizing structure, the foam layer may be held in place for an excess of 30 seconds.

Figure 23B:
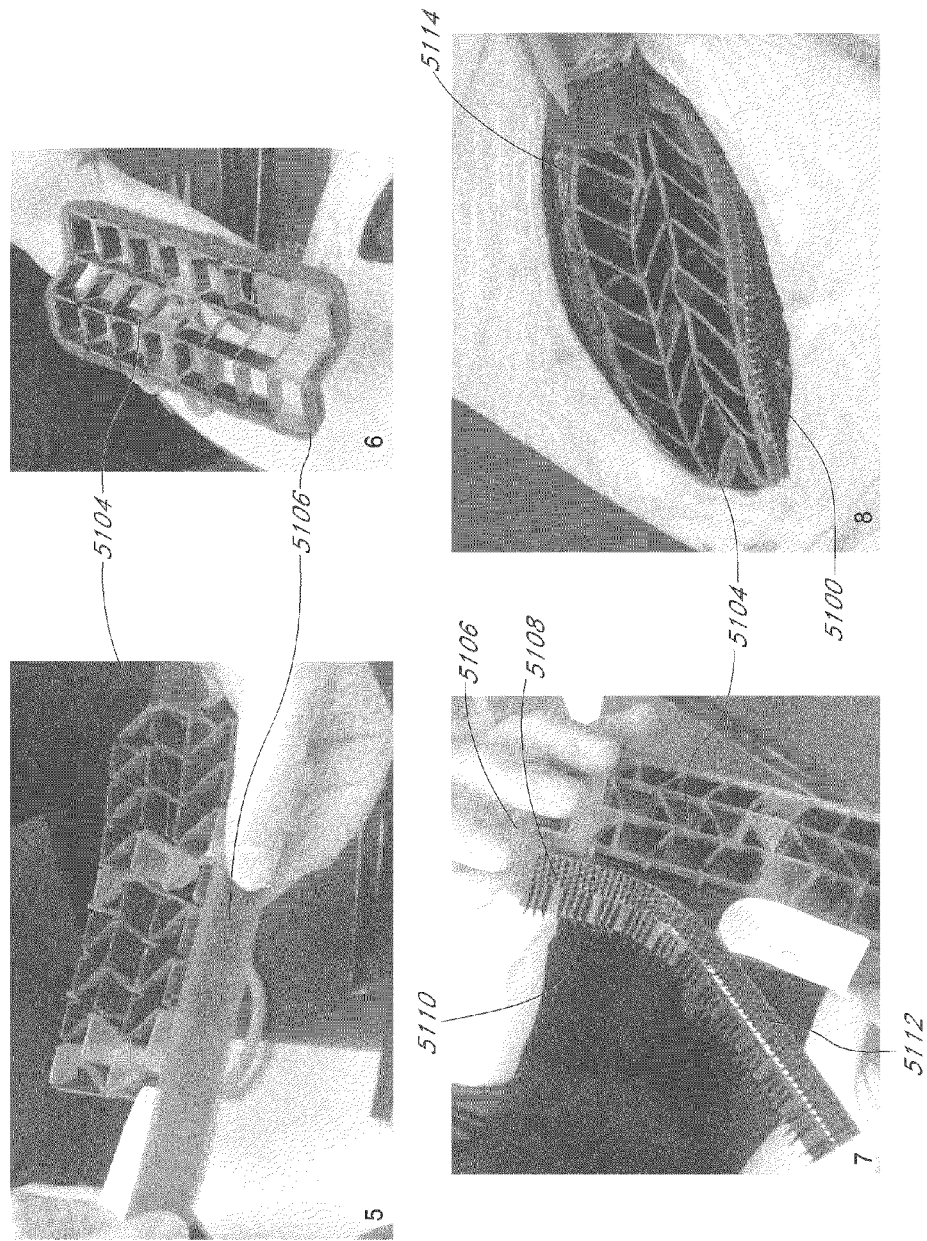

Step 7 of FIG. 23B shows the next step of an embodiment of the method, wherein an anchoring layer 5108 comprising a first band of longer anchors 5110 and a second band of shorter anchors 5112 is attached to the foam layer 5106. The anchoring layer 5108 may be shaped to the size of the perimeter of the stabilizing structure 5104 and adhered to the foam layer 5106 via the removal of an adhesive backing layer covering an adhesive surface on a side of the elongate layer opposite the anchors. The anchoring layer may partially or completely surround the foam layer. To allow the anchoring layer to properly adhere to the stabilizing structure, the anchoring layer may be held in place for a period of time, for example in excess of 30 seconds. Once the anchoring layer has been applied to the foam layer 5106 and stabilizing structure 5104, the entire wound closure device 5114 may be placed into the wound 5100, as displayed in step 8 of FIG. 23B. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 5114 may be placed such that the longitudinal sides of the matrix align with the longitudinal axis of the wound 5100.

In some embodiments, it may be preferable to orient the shorter second anchors 5112 towards the top of the wound and the longer first anchors 5110 towards the bottom of the wound so that the shorter anchors 5112 may engage the fatty tissue of the wound. However, in other embodiments, depending on the shape of the anchors, it may be desirable to orient the combination in the opposite orientation such that the longer anchors 5110 engage the fatty tissue. The anchors may also have the same length. In certain embodiments, the anchors may be color coded, to direct a use to a particular orientation of the stabilizing structure. The anchors also need not cover the entire outer perimeter of the stabilizing structure. In some embodiments, anchors are provided only on the first side 4234 and second side 4236 of the stabilizing structure (for an embodiment such as illustrated in FIG. 15G).

Figure 23C:
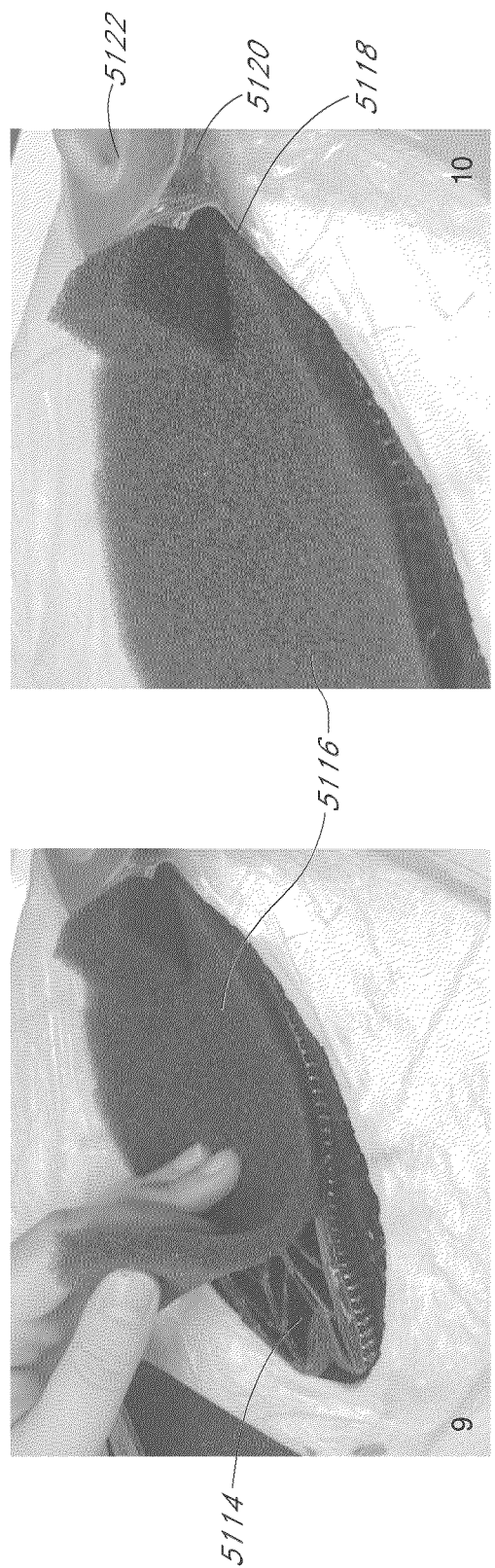

FIG. 23C contains photographs of step 9 and 10 of a method of wound closure and treatment. In step 9, another foam layer 5116 (for example, a 10 mm layer of foam) is placed on top of the wound closure device 5114. As displayed in step 10, a bridging portion of foam 5118 may be placed in intimate contact with the foam layer 5116 at the edge of the wound. The bridging portion of foam 5118 may extend over intact skin, with a piece of drape 5120 placed between it and the intact skin. Further, a suction port 5122 may be connected to the bridging portion 5118 with a section of drape 5120 between. In alternative embodiments, the bridging portion 5118 and suction port 5122 may be placed on the wound during a different step, for example during steps 1 and 2 as depicted in FIG. 23A.

Figure 24:
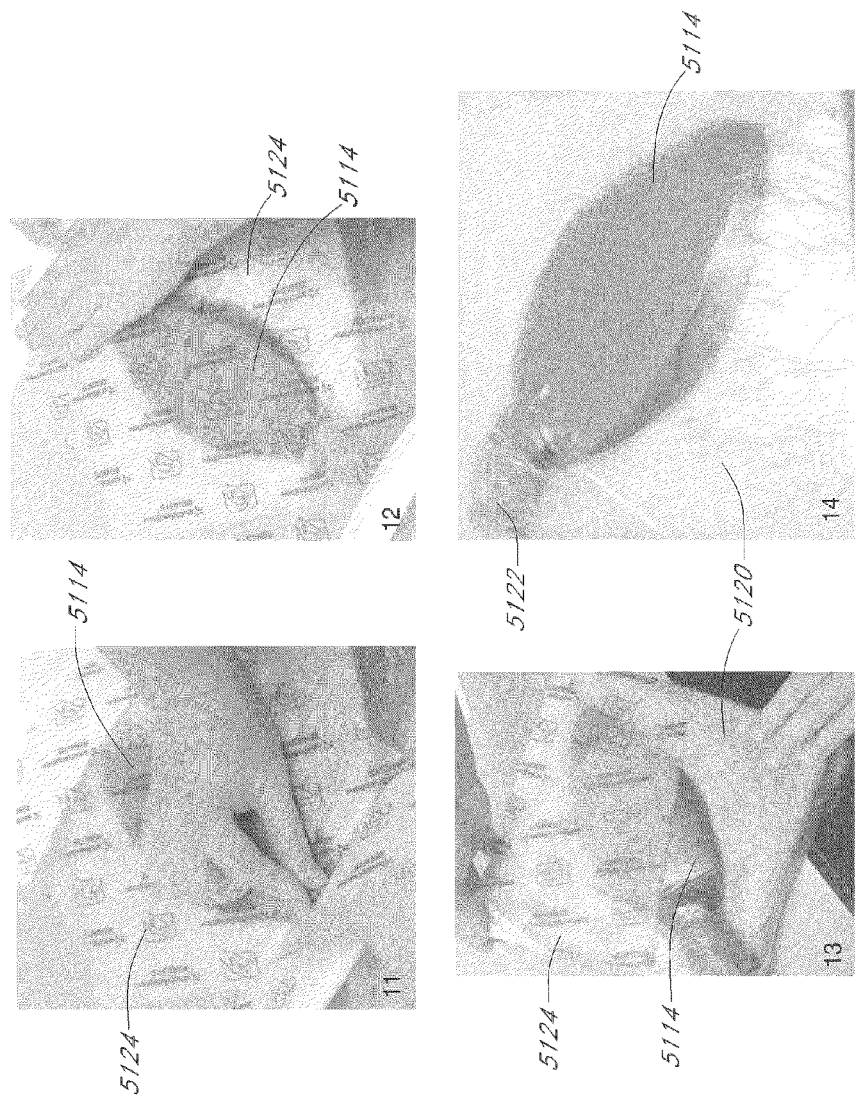
FIG. 24 illustrates an embodiment of steps of a method of treating a wound.

In FIG. 24, as shown by steps 11-14, the device may be covered by one or more drapes 5120. A hole may be made in the drape covering the bridging portion of foam, and a suction port 5122 may be placed over the hole. A protective layer 5124 on the top surface of the one or more drapes may be removed after the drapes 5120 are applied. Once the drapes 5120 are applied and the port is in place, negative pressure may be applied to the wound through the drape from a vacuum source. The negative pressure can cause the stabilizing structure to collapse horizontally as described elsewhere in this specification. The tissue anchors adhered to the stabilizing structure through the porous layer engage tissue of the wound and may facilitate closure of the wound.

Figure 25A:
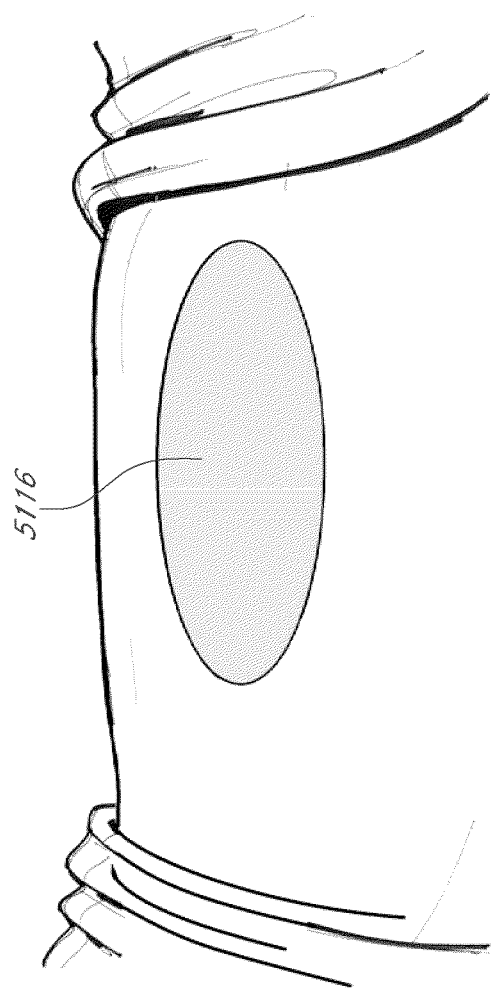
FIGS. 25A-G illustrate an embodiment of steps of a method of treating a wound.
Figure 25B:
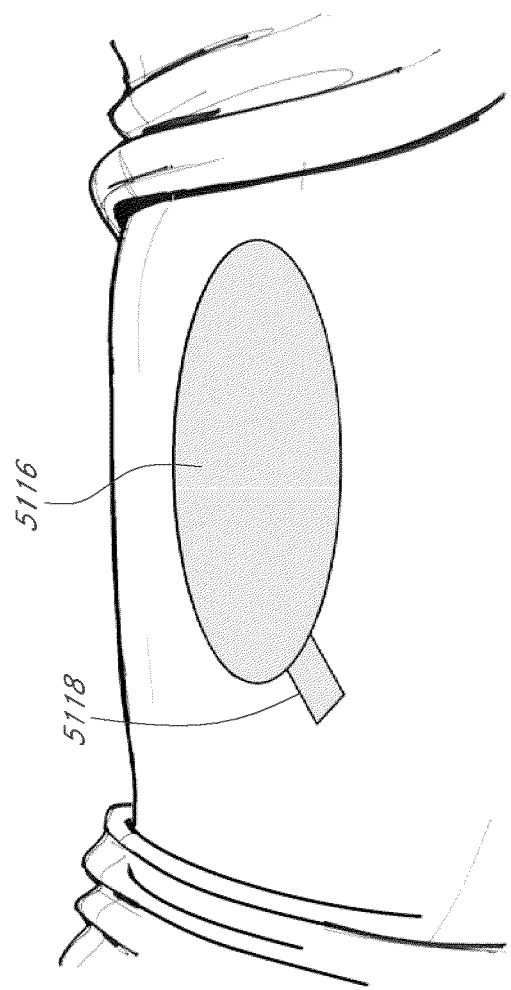
Figure 25C:
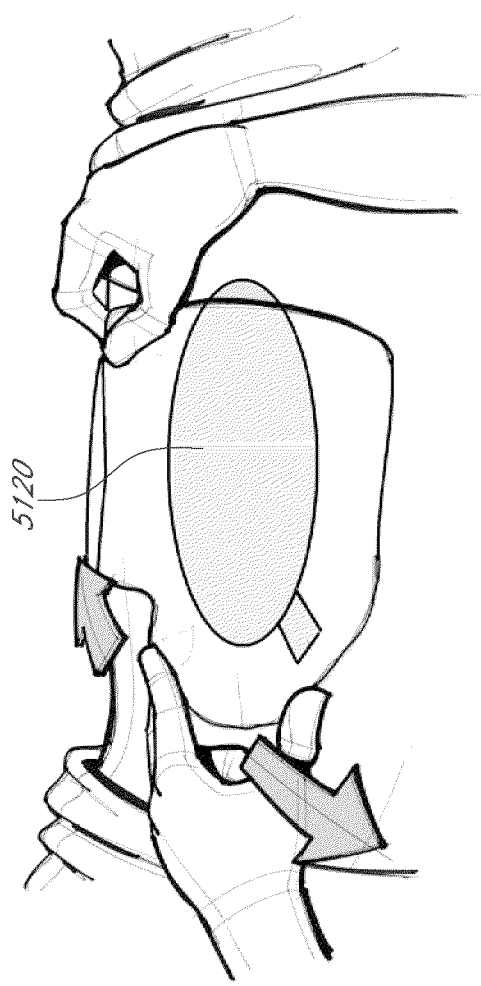
Figure 25D:
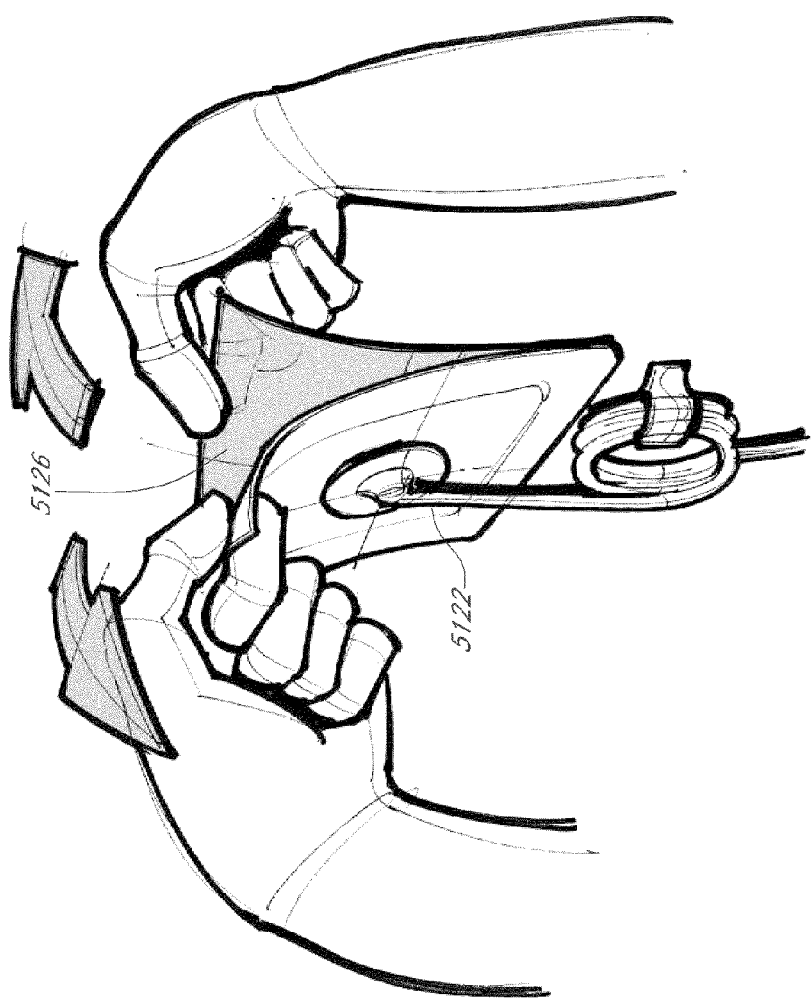
Figure 25E:
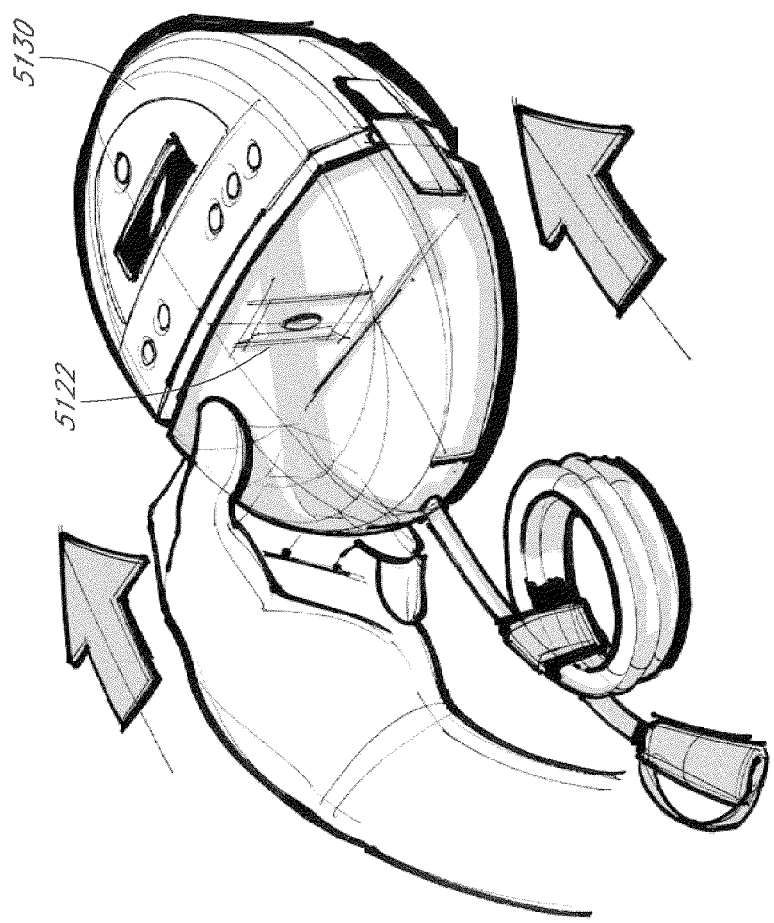
Figure 25F:
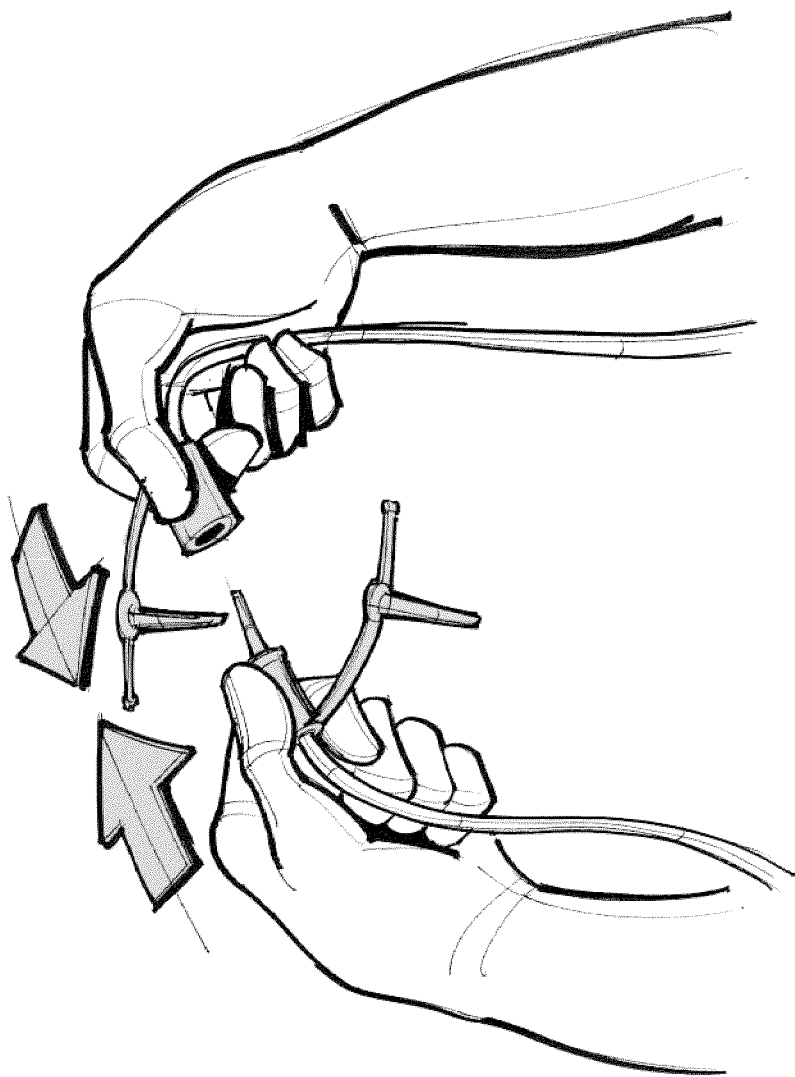
Figure 25G:
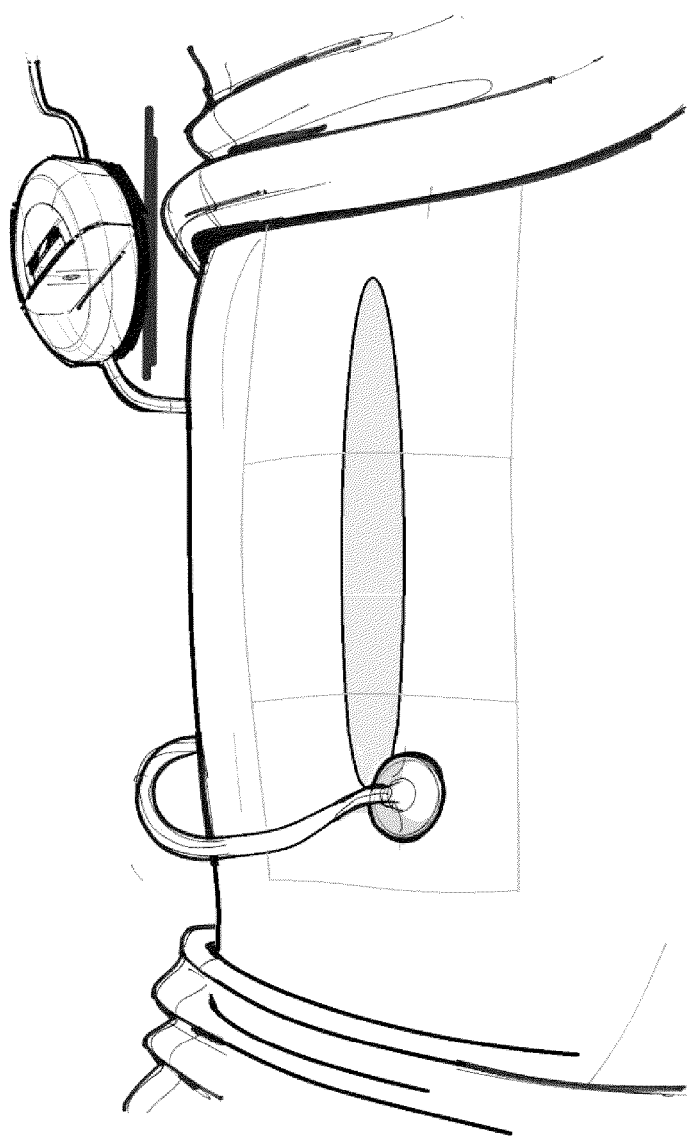

FIGS. 25A-25C provide further illustrations of an upper foam layer 5116 being placed in a wound, followed by placing a bridging portion 5118 and placing one or more drapes or wound covers 5120. FIGS. 25D-25G illustrate an embodiment of several steps in a method for the treatment and closure of a wound. As illustrated in FIG. 25D, a suction port 5122 is separated from a release liner 5126 and later applied to a wound as depicted in FIGS. 23A-24. FIG. 25E illustrates a canister 5128 being inserted into a negative pressure wound therapy device 5130 in preparation for the collection of wound exudate. FIG. 25F illustrates the snap connection between the tubing connected to the suction port and the tubing connected to the negative pressure wound therapy device 5130. Once the connection has been made, negative pressure wound treatment may begin as depicted in FIG. 25G.

Further details regarding the wound closure devices, stabilizing structures, related apparatuses and methods of use that may be combined with or incorporated into any of the embodiments described herein are found in International Application No. PCT/US2013/050698, filed Jul. 16, 2013, the entirety of which is hereby incorporated by reference.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future. For example, in addition to any claims presented herein, the following embodiments are also intended to be encompassed within the scope of the present disclosure.

1. An apparatus for wound treatment, comprising:
   a wound filler configured to collapse horizontally within a wound;
   a securing material configured to surround the wound filler, the securing material comprising:
      an elongate layer configured to be placed in contact with the wound; and a lip extending outwardly from elongate layer, wherein the lip is capable of being positioned beneath the fascia of a patient;

wherein the elongate layer and the lip are integrated as a single piece and form a generally L-shaped cross-section; and a wound cover configured to be placed over a wound.

2. The apparatus of Embodiment 1, wherein an inner surface of the layer is configured to be attached to the wound filler.

3. The apparatus of Embodiment 2, wherein the inner surface has means for attaching the inner surface of the layer to the wound filler.

4. The apparatus of Embodiment 3, wherein the means for attaching the inner surface of the layer to the wound filler comprise an attachment mechanism selected from the group consisting of a barb, an adhesive, Velcro, hooks of Velcro, mushroom shaped hooks of Velcro, a hooked shape, a staggered hook, a staggered barb, and any combination thereof.

5. The apparatus of any one of Embodiments 1-4 the preceding claims, wherein an outer surface of the layer is configured to be attached to a wound surface.

6. The apparatus of Embodiment 5, wherein the outer surface has means for attaching the outer surface of the layer to the wound surface.

7. The apparatus of Embodiment 6, wherein the means for attaching the outer surface of the layer to the wound surface is selected from the group consisting of a barb, an adhesive, Velcro, hooks of Velcro, mushroom shaped hooks of Velcro, a hooked shape, a staggered hook, a staggered barb, and any combination thereof.

8. The apparatus of any one of Embodiments 1-7, wherein the lip has means for attaching the lip to the fascia.

9. The apparatus of Embodiment 8, wherein the means for attaching the lip to the fascia comprise an attachment mechanism selected from the group consisting of a barb, an adhesive, Velcro, hooks of Velcro, mushroom shaped hooks of Velcro, a hooked shape, a staggered hook, a staggered barb, and any combination thereof.

10. The apparatus of Embodiment 9, wherein the means for attaching the lip to the fascia comprise a lateral attachment mechanism, the lateral attachment mechanism extending outwardly from a front surface of the lip.

11. The apparatus of any one of Embodiments 1-10, further comprising a plurality of fingers extending outwardly from the lip.

12. The apparatus of any one of Embodiments 1-11, further comprising an organ protection layer configured to be positioned over a wound beneath the wound filler.

13. The apparatus of any one of Embodiments 1-12, further comprising one or more foam layers configured to be positioned above and/or below the wound filler.

14. The apparatus of any one of Embodiments 1-13, further comprising a connection for connecting the wound cover to a source of negative pressure.

15. The apparatus of any one of Embodiments 1-15, further comprising a negative pressure source configured to be connected to the wound cover to provide negative pressure to the wound.

16. A method of treating a wound using the apparatus of any one of Embodiments 1-15, comprising applying negative pressure to the wound through the wound cover positioned over the wound with the wound filler positioned within the wound, wherein the wound filler is surrounded by the elongate layer and the lip is positioned beneath the fascia; and wherein the wound filler collapses horizontally under negative pressure.

What is claimed is:

1. An apparatus for wound treatment, comprising:
an elongate layer of material configured to be placed in contact with a wound, the elongate layer capable of being formed into an annular shape; and
a lip integral with the elongate layer and extending outwardly from the elongate layer when the elongate layer is arranged in an annular shape;
wherein the lip is configured to be positioned beneath the fascia of a patient; and
wherein a portion of the elongate layer extends above a plane on a top surface of the lip when the elongate layer is formed into the annular shape.

2. The apparatus of claim 1, wherein the elongate layer is made of foam.

3. The apparatus of claim 1, wherein the lip is made of foam.

4. The apparatus of claim 1, wherein the elongate layer has an inner surface and an outer surface and a thickness therebetween, wherein the thickness of the layer is less than a height of the inner and outer surfaces.

5. The apparatus of claim 1, further comprising a wound filler, wherein the elongate layer surrounds the wound filler.

6. The apparatus of claim 5, wherein the wound filler comprises a material configured to compress horizontally as negative pressure is applied and cause wound edges to draw closer together and configured to be relatively rigid to prevent vertical collapse of a wound cover.

7. The apparatus of claim 5, wherein the wound filler comprises foam.

8. The apparatus of any one of claim 5, further comprising an organ protection layer configured to be positioned over a wound beneath the wound filler.

9. The apparatus of any one of claim 5, further comprising one or more foam layers configured to be positioned above and/or below the wound filler.

10. The apparatus of claim 1, further comprising a wound cover configured to be placed over a wound.

11. The apparatus of claim 10, further comprising a connection for connecting the wound cover to a source of negative pressure.

12. The apparatus of claim 10, further comprising a negative pressure source configured to be connected to the wound cover to provide negative pressure to a wound.

13. The apparatus of claim 1, wherein an inner surface of the elongate layer is configured to be attached to a wound filler.

14. The apparatus of claim 13, wherein the inner surface has means for attaching the inner surface of the elongate layer to the wound filler.

15. The apparatus of claim 14, wherein the means for attaching the inner surface of the elongate layer to the wound filler comprises an attachment mechanism selected from the group consisting of a barb, an adhesive, a hook-and-loop fastener, hooks of a hook-and-loop fastener, mushroom shaped hooks of a hook-and-loop fastener, and any combination thereof.

16. The apparatus of claim 1, wherein an outer surface of the elongate layer is configured to be attached to a wound surface.

17. The apparatus of claim 16, wherein the outer surface has means for attaching the outer surface of the elongate layer to the wound surface.

18. The apparatus of claim 17, wherein the means for attaching the outer surface of the elongate layer to the wound surface is selected from the group consisting of a barb, an adhesive, tissue grabbers, glue, suturing, mesh, and any combination thereof.

19. The apparatus of claim 1, wherein the lip has means for attaching the lip to the fascia.

20. The apparatus of claim 19, wherein the means for attaching the lip to the fascia comprise an attachment mechanism selected from the group consisting of a barb, an adhesive, tissue grabbers, glue, suturing, mesh, and any combination thereof.

21. The apparatus of claim 19, wherein an outer surface of the elongate layer has means for attaching the outer surface of the elongate layer to the wound surface that is different from the means for attaching the lip to the fascia.

22. The apparatus of claim 1, further comprising a plurality of fingers extending outwardly from the lip.

23. The apparatus of claim 22, wherein the fingers are covered by a slitted organ protection layer.

24. The apparatus of claim 22, wherein the fingers comprise a foam material different from the material of the elongate layer.

25. The apparatus of claim 24, wherein the foam material for the fingers comprises foam having a porosity between 200 ppi and 60 ppi.

26. The apparatus of claim 1, wherein the elongate layer and the lip form a generally L-shaped cross-section.

27. The apparatus of claim 1, wherein the elongate layer has a first end and a second end and means for attaching the first and second ends together.

28. A method of treating a wound using the apparatus of claim 1 comprising applying negative pressure to the wound through a wound cover positioned over the wound and a wound filler positioned within the wound, wherein the wound filler is surrounded by the elongate layer of material and the lip is positioned beneath the fascia.

29. The method of claim 28, wherein the wound is an abdominal wound.

30. The method of claim 28, further comprising positioning an organ protection layer over the wound and then positioning the wound filler within the wound.

* * * * *

UNITED STATES PATENT AND TRADEMARK OFFICE
CERTIFICATE OF CORRECTION

PATENT NO. : 10,124,098 B2
APPLICATION NO. : 14/774689
DATED : November 13, 2018
INVENTOR(S) : Raymond M. Dunn et al.

It is certified that error appears in the above-identified patent and that said Letters Patent is hereby corrected as shown below:

In the Specification

In Column 6, Line 34, change "mmHg" to --mmHg.--

In Column 10, Line 40, change "FIG." to --FIGS.--

In Column 10, Line 49, change "FIG." to --FIGS.--

In Column 10, Line 53, change "FIG." to --FIGS.--

In Column 11, Line 60, change "mm)" to --mm).--

In Column 11, Line 65, change "mm)" to --mm).--

In Column 15, Line 10, change "FIG." to --FIGS.--

In Column 15, Line 19, change "FIG." to --FIGS.--

In Column 15, Line 47, change "FIG." to --FIGS.--

In Column 15, Line 56, change "mm)" to --mm).--

In Column 16, Line 57, change "FIG." to --FIGS.--

In Column 19, Line 18, change "FIG." to --FIGS.--

Signed and Sealed this
Twenty-sixth Day of March, 2019

Andrei Iancu
*Director of the United States Patent and Trademark Office*

In the Claims

In Column 42, Line 35, Claim 8, change "of any one of" to --of--

In Column 42, Line 38, Claim 9, change "of any one of" to --of--